(12) United States Patent
Antonov et al.

(10) Patent No.: US 7,517,992 B2
(45) Date of Patent: Apr. 14, 2009

(54) NON-NUCLEOSIDE REVERSE TRANSCRIPTASE INHIBITORS

(75) Inventors: Dmitry Antonov, Huddinge (SE); Christian Sund, Huddinge (SE); Stefan Lindström, Huddinge (SE); Christer Sahlberg, Huddinge (SE)

(73) Assignee: Medivir AB, Huddinge (SE)

( * ) Notice: Subject to any disclaimer, the term of this patent is extended or adjusted under 35 U.S.C. 154(b) by 552 days.

(21) Appl. No.: 10/526,598

(22) PCT Filed: Sep. 5, 2003

(86) PCT No.: PCT/EP03/09872

§ 371 (c)(1),
(2), (4) Date: Jul. 7, 2005

(87) PCT Pub. No.: WO2004/021969

PCT Pub. Date: Mar. 18, 2004

(65) Prior Publication Data

US 2006/0167055 A1    Jul. 27, 2006

(30) Foreign Application Priority Data

Sep. 5, 2002  (EP) .................................. 02019997

(51) Int. Cl.
*C07D 401/12*   (2006.01)
*A61K 31/444*   (2006.01)

(52) U.S. Cl. ...................... 546/256; 514/333
(58) Field of Classification Search ........................ None
See application file for complete search history.

(56) References Cited

U.S. PATENT DOCUMENTS

| | | | |
|---|---|---|---|
| 6,610,714 B2 * | 8/2003 | Sahlberg et al. | ............ 514/353 |
| 6,716,850 B2 * | 4/2004 | Lindstrom et al. | ..... 514/255.05 |
| 2008/0070951 A1 * | 3/2008 | Sund et al. | ................ 514/337 |

FOREIGN PATENT DOCUMENTS

| | | |
|---|---|---|
| WO | WO 00/47561 A | 8/2000 |
| WO | WO 00/47561 A1 | 8/2000 |
| WO | WO 03/020705 A | 3/2002 |
| WO | WO 02/070516 A | 9/2002 |
| WO | WO 02/070516 A2 | 9/2002 |
| WO | WO 03/020705 A1 | 3/2003 |

OTHER PUBLICATIONS

2006 Chemical Abstracts Catalog, published 2006 by Chemical Abstracts Service, p. 52.*
Merriam-Webster's Collegiate Dictionary, Tenth Edition, published 1998 by Merriam-Webster, Incorporated, pp. 924 and 935.*
"Urea-PETT Compounds as a New Class of HIV-1 Reverse Transcriptase Inhibitors. 3. Synthesis and Further Structure-Activity Relationship Studies of PETT Analogues" by Marita Hogberg et al., Journal of Medicinal Chemistry, vol. 42, No. 20, 1999, pp. 4150-4160.
Hoegberg, M et al., "Urea-PETT compounds as a new class of HIV-1 . . . ," Journal of Medicinal Chemistry, 1999, vol. 42, No. 20, pp. 4150-4160.

* cited by examiner

*Primary Examiner*—Shaojia Anna Jiang
*Assistant Examiner*—Eric S Olson
(74) *Attorney, Agent, or Firm*—Birch Stewart Kolasch & Birch, LLP

(57) ABSTRACT

A compound of the formula (Y): where; $R_1$ is O, S; $R_2$ is a nitrogen-containing heterocycle; $R_3$ is H, $C_1$-$C_3$ alkyl; X is —$(CR_8R_8')_n$-D-$(CR_8R_8')_m$—; D is a bond, —$NR_9$—, —O—, —S—, —S(=O)— or —S(=O)_2$—; n and m are independently 0, 1 or 2, $R_8$ and $R_8'$ are independently H, $C_1$-$C_3$ alkyl, halo$C_1$-$C_3$alkyl, hydroxy, or $R_8$ and $R_8'$ together with their adjacent C atom is —C(=O)—; $R_9$ is independently H, $C_1$-$C_3$ alkyl; E is $CH_2$—, —CHOH—, —C(=O)—, —$NR_9$—, —O—, —S—, —S(=O)_2$—; n and m are independently 0, 1 or 2; p and q are independently 0, 1 or 2, where $p+q \leq 2$; $R_{10}$ is an optionally substituted carbocycle or heterocycle; $R_{11}$ is independently H, $C_1$-$C_3$ alkyl, halo substituted $C_1$-$C_3$alkyl, hydroxy; have utility as HIV antivirals.

15 Claims, No Drawings

NON-NUCLEOSIDE REVERSE TRANSCRIPTASE INHIBITORS

This application is a national phase under 35 U.S.C § 371 of PCT International Application No. PCT/EP2003/009872 which has an International filing date of Sep. 5, 2003, which designated the United States of America.

TECHNICAL FIELD

This invention relates to non-nucleoside reverse transcriptase inhibitors active against HIV-1 and having an improved resistance and pharmacokinetic profile. The invention further relates to novel intermediates in the synthesis of such-compounds and the use of the compounds in antiviral methods and compositions.

BACKGROUND OF THE INVENTION

Our co-pending, but as of the priority date, unpublished PCT applications nos PCT/EP02/02328 & PCT/EP02/02346 claim novel NNRTIs of the formula I/II

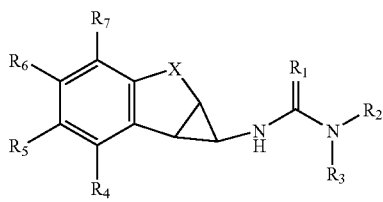

where:

$R_1$ is O, S;

$R_2$ is an optionally substituted, nitrogen-containing heterocycle, wherein the nitrogen is located at the 2 position relative to the (thio)urea bond;

$R_2$ is an optionally substituted, nitrogen-containing heterocycle, wherein the nitrogen is located at the 2 position relative to the (thio)urea bond;

$R_3$ is H, $C_1$-$C_3$ alkyl, $R_4$-$R_7$ are independently selected from H, $C_1$-$C_6$ alkyl, $C_2$-$C_6$ alkenyl, $C_2$-$C_6$ alkynyl, halo$C_1$-$C_6$ alkyl, $C_1$-$C_6$ alkanoyl, halo$C_1$-$C_6$ alkanoyl, $C_1$-$C_6$ alkoxy, halo$C_1$-$C_6$ alkoxy, $C_1$-$C_6$ alkyloxy$C_1$-$C_6$ alkyl, halo$C_1$-$C_6$ alkyloxy$C_1$-$C_6$ alkyl, hydroxy$C_1$-$C_6$ alkyl, amino$C_1$-$C_8$ alkyl, carboxy$C_1$-$C_6$ alkyl, cyano$C_1$-$C_6$ alkyl, amino, carboxy, carbamoyl, cyano, halo, hydroxy, keto and the like;

X is —$(CH_2)_n$-D-$(CH_2)_m$— or X is —$(CRaRb)_c$—

D is —$NR_8$—, —O—, —S—, —S(=O) or —$S(=O)_2$—

$R_8$ is H, $C_1$-$C_3$ alkyl $R_a$ and $R_b$ are independently H, $C_1$-$C_3$ alkyl, OH or $R_a$ and $R_b$ together are =O n and m are independently 0 or 1;

c is 1, 2 or 3 and pharmaceutically acceptable salts and prodrugs thereof.

Although the urea and thiourea NNRTIs disclosed in the above documents are exquisitely active against reverse transcriptase, especially that of HIV-1, the nature of the HIV virus with its extreme lack of replicative fidelity and consequent tendency to rapid resistance development prompts a demand for further antiretroviral agents with enhanced antiviral performance against problematic drug escape mutants, notably at the RT 100, 103 and/or 181 positions.

BRIEF DESCRIPTION OF THE INVENTION

In accordance with a first aspect of the invention there are provided compounds of the formula Y:

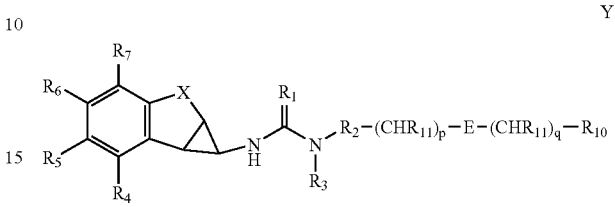

where;

$R_1$ is O, S;

$R_2$ is a nitrogen-containing heterocycle, wherein a nitrogen is located at the 2 position relative to the (thio)urea bond;

$R_3$ is H, $C_1$-$C_3$ alkyl, $R_4$-$R_7$ are independently selected from H, $C_1$-$C_6$ alkyl, $C_2$-$C_6$ alkenyl, $C_2$-$C_6$ alkynyl, halo$C_1$-$C_6$ alkyl, $C_1$-$C_6$ alkanoyl, halo$C_1$-$C_6$ alkanoyl, $C_1$-$C_6$ alkoxy, halo$C_1$-$C_6$ alkoxy, $C_1$-$C_6$ alkyloxy$C_1$-$C_6$ alkyl, halo$C_1$-$C_6$ alkyloxy$C_1$-$C_6$ alkyl, hydroxy$C_1$-$C_6$ alkyl, amino$C_1$-$C_6$ alkyl, carboxy$C_1$-$C_6$ alkyl, cyano$C_1$-$C_6$ alkyl, amino, carboxy, carbamoyl, cyano, halo, hydroxy, keto;

X is —$(CR_8R_8')_n$-D-$(CR_8R_8')_m$—;

D is a bond, —$NR_9$—, —O—, —S—, —S(=O)— or —$S(=O)_2$—;

n and m are independently 0, 1 or 2, provided that they are not both 0 when D is a bond;

$R_8$ and $R_8'$ are independently H, $C_1$-$C_3$ alkyl, halo$C_1$-$C_3$alkyl, hydroxy, or $R_8$ and $R_8'$ together with their adjacent C atom is —C(=O)—

$R_9$ is independently H, $C_1$-$C_3$ alkyl;

E is —$CH_2$—, —CHOH—, —C=O—, —$NR_9$—, —O—, —S—, —$S(=O)_2$—;

p and q are independently 0, 1 or 2, where p+q 2;

$R_{10}$ is an optionally substituted, saturated or unsaturated 5-7 membered carbocyclic ring or an optionally substituted, saturated or unsaturated 5-7 membered heterocyclic ring containing 1 to 3 hetero atoms selected from O, N and S;

$R_{11}$ is independently H, $C_1$-$C_3$ alkyl, halo substituted $C_1$-$C_3$alkyl, hydroxy;

with the proviso that —$(CHR_{11})_p$-E-$(CHR_{11})_q$—$R_{10}$ is not unsubstituted phenoxy;

and pharmaceutically acceptable salts and prodrugs therof.

The currently preferred value for $R_1$ is O, that is a urea derivative, although $R_1$ as S (ie a thiourea derivative) is also highly potent.

Representative values for $R_2$ include thiazolyl, pyridyl, pyrimidyl, pyrazinyl, pyridazinyl, pyrrolyl, imidazolyl, indolyl, triazolyl, tetrazolyl, piperidyl, piperazinyl and fused rings such as benzothiazolyl, benzopyridyl, benzodiazolyl, benzimidazolyl, quinolyl, purinyl and the like, any of which can be optionally substituted, in addition to the —$(CHR_9)_p$-E-$(CHR_9)_q$—$R_{10}$ substituent, for example with $C_1$-$C_6$ alkyl, $C_1$-$C_6$ alkoxy, $C_2$-$C_6$ alkenyl, $C_2$-$C_8$ alkynyl, $C_2$-$C_8$ alkenoxy, $C_1$-$C_6$ alkoxy$C_1$-$C_6$ alkyl, $C_1$-$C_6$ alkanoyl, halo$C_1$-$C_6$ alkyl, $C_1$-$C_4$ alkanoyloxy, $C_1$-$C_4$ alkylthio, amino (including $C_1$-$C_3$ alkyl-substituted amino), carboxy, carbamoyl, cyano, halo, hydroxy, aminomethyl, carboxymethyl, hydroxymethyl, nitro, —SO₂Q or —C(=O)Q, where Q is $C_1$-$C_6$ alkyl, halo-substituted $C_1$-$C_6$ alkyl and the like.

Preferred $R_2$ values include pyrid-2-yl and thiazol-2-yl.

Heteroatoms in $R_2$ can be derivatised, such as with $C_1$-$C_6$ alkyl, oxo and the like, but are preferably underivatised. The —(CHR₉)$_p$-E-(CHR₉)$_q$—R₁₀ substituent to $R_2$ may be ortho or meta relative to the bond to the (thio)urea function but is preferably para.

Conveniently, p and q are 0 and E represents a thioether, secondary amine or especially an ether function. A further convenient —CHR₁₁-E-CHR₁₁— group is methylene, ethylene or propylene, optionally substituted with one to 3 halo or 1 hydroxy or keto groups. A still further convenient configuration for —CHR₁₁-E-CHR₁₁— is oxymethyl or oxyethyl.

Representative $R_{10}$ groups include phenyl, cycloalkyl, cycloalkenyl, pyridyl, furyl, thiazolyl, pyrimidyl, pyrazinyl, pyridazinyl, pyrrolyl, imidazolyl, indolyl, triazolyl, tetrazolyl, piperidyl, piperazinyl and morpholino.

The optional substituents to $R_{10}$ include one to three substituents including halo (such as fluoro), cyano, morpholinomethyl, morpholinoketo and the like.

Favoured $R_{10}$ groups include 2-fluorophenyl, 3-fluorophenyl, 4-fluorophenyl, 3,4-difluorophenyl, 2,3-difluorophenyl, 3,5-difluorophenyl, 2,3,4-triflourophenyl, 2-cyanophenyl, 3-cyanophenyl, 4-cyanophenyl, 4-cyano-3-fluorophenyl, 3-cyano-5-fluorophenyl, pyrid-2-yl, pyrid-3-yl, pyrid-4-yl, 5-fluorpyrid-3-yl, piperazinyl, morpholinyl and piperidyl.

Convenient —(CHR₁₁)-E-(CHR₁₁)R₁₀ values thus include pyrid-3-yloxy, pyrid-4-yloxy, fluoro- or cyano-substituted pyrid-3-yloxy, fluoro- or cyano-substituted pyrid4-yloxy, 4-fluoro-3-N-morpholinornethylphenoxy, 3-N-morpholinornethylphenoxy, 4-fluoro-3-N-morpholino-keto-phenoxy, 4-fluorophenoxy, 3-fluorophenoxy, 3,4-difluorophenoxy, 4-cyanoph enoxy, 3-cyanophenoxy, 4-cyano-3-fluorophenoxy, 3-cyano-4-fluorophenoxy, 3-cyano-5-fluorophenoxy and the like.

The currently preferred value for $R_3$ is H.

Preferably $R_4$ is hydrogen, halo or hydroxy, especially fluoro.

Preferably $R_5$ is halo, $C_{1-3}$ alkylcarbonyl, $C_{1-3}$alkyloxy or H, especially fluoro and most preferably H.

Preferably $R_6$ is hydrogen, halo, $C_1$-$C_3$alkyloxy, $C_{1-3}$alkylcarbonyl, cyano or ethynyl, especially methoxy or fluoro and most preferably H.

Preferably $R_7$ is hydrogen, halo, $C_{1-3}$alkyloxy, or $C_{1-3}$alkylcarbonyl, most preferably fluoro.

Preferably $R_5$ and $R_6$ are H and $R_4$ and $R_7$ are halo, most preferably both are fluoro.

The compounds of formula I may be administered as a racemic mixture, but preferably the cyclopropyl moiety intermediate the (thio)urea function, X and the phenyl ring (denoted Y below) is at least 75% such as around 90% enantiomerically pure with respect to the conformation:

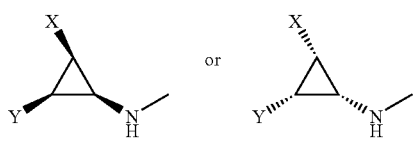

Prefered optical isomers of the compounds of formula I show a negative optical rotation value. Such isomers, for example when X is —O—CH₂—, tend to elute less rapidly from a chiral chromatagram, for example chiral AGP 150×10 mm, 5 μm; Crom Tech LTD Colomn, flow rate 4 ml/min, mobile phase 89 vol % 10 mM HbAc/NH₄OAc in acetonitrile. On the basis of preliminary x-ray crystallography analysis a presently favoured absolute configuration appears to be:

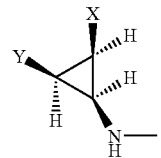

The currently preferred value for D is —O—. Convenient values for n and m include 1:0 and 1:1. Preferred values of n:m include 0:2 and especially 0:1, that is a chroman derivative. Conveniently each R8 and R8' is H. Alternatively, in the case where n is 0 and m is 1, R8 is advantageously H and R8' is OH.

Particularly preferred compounds have stereochemistry corresponding to (1S,1aR,7bR)-1,1a,2,7b-tetrahydro-cyclopropa[c]chromen-1-yl. For the sake of clarity, it is noted that the structure:

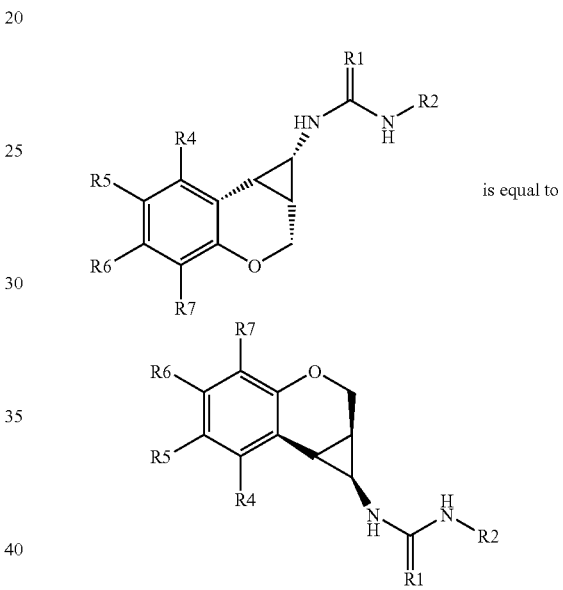

The expression $C_1$-$C_n$ alkyl, where n is 3, 6, 7 etc or lower alkyl includes such groups as methyl, ethyl, n-propyl, isopropyl, n-butyl, s-butyl, t-butyl, n-pentyl, n-hexyl, 3-methyl pentyl and the like. The term halo refers to chloro, bromo, fluoro and iodo, especially fluoro. $C_1$-$C_n$ alkoxy refers to groups such as methoxy, ethoxy, propoxy, t-butoxy and the line. $C_2$-$C_n$ alkenyl refers to groups such as vinyl, 1-propen-2-yl, 1-buten-4-yl, 1-penten-5-yl, 1-buten-1-yl and the like. $C_1$-$C_n$ alkylthio includes methylthio, ethylthio, t-butylthio and the like. $C_1$-$C_n$ alkanoyloxy includes acetoxy, propionoxy, formyloxy, butyryloxy and the like. $C_2$-$C_n$ alkenoxy includes ethenyloxy, propenyloxy, iso-butoxyethenyl and the like. Halo$C_1$-$C_n$ alkyl (including complex substituents comprising this moiety such as halo$C_1$-$C_n$ alkyloxy) includes alkyls as defined herein substituted 1 to 3 times by a halogen including trifluoromethyl, 2-dichloroethyl, 3,3-difluoropropyl and the like. The term amine includes groups such as NH₂, NHMe, N(Me)₂ which may optionally be substituted with halogen, $C_1$-$C_7$ acyloxy, $C_1$-$C_6$ alkyl, $C_1$-$C_6$ alkoxy, nitro, carboxy, carbamoyl, carbamoyloxy, cyano, methylsulphonylamino and the like. Carboxy, carboxymethyl and carbamoyl include the corresponding pharmaceutically acceptable $C_1$-$C_6$ alkyl and aryl esters.

Prodrugs of the compounds of formula I are those compounds which following administration to a patient release a compound of the formula I in vivo. Typical prodrugs are pharmaceutically acceptable ethers and especially esters (including phosphate esters) when any of $R_4$-$R_7$ represent an hydroxy function, pharmaceutically acceptable amides or carbamates when any of the $R_2$ substituent or $R_4$-$R_7$ represent an amine function or pharmaceutically acceptable esters when the $R_2$ substituent or $R_4$-$R_7$ represent a carboxy function. Pharmaceutically acceptable esters include alkyl esters, including aceylm, ethanoyl, butyryl, t-butyryl, and pivaloyl, phosphate esters and sulphonic esters (ie those derived from $RSO_2OH$, where R is lower alkyl or aryl). harmaceutically acceptable esters include lower alkyl ethers and the ethers disclosed in WO00/47561, especially methoxyaminoacyl and ethoxyaminoacyl.

The compounds of formula I can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride. hydrobromide, hydroiodide, sulphate, bisulphate, hemisulphate, thiocyanate, persulphate, phosphoric and sulphonic acids.

Hydroxy protecting group as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). Hydroxy protecting groups comprise substituted methyl ethers, for example, methoxymethyl, benzyloxymethyl, 2-methoxyethoxymethyl, 2-(trimethylsilyl)ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyidimethylsilyl and t-butyidiphenylsilyl; and esters prepared by reacting the hydroxyl group with a carboxylic acid, for example, acetate, propionate, benzoate and the like.

Similarly, N-protecting group as used herein refers to those conventional N-protecting groups disclosed in Greene, "Protective Groups in Organic Synthesis", John Wiley & Sons New York 1981.

The invention further provides pharmaceutical compositions comprising the compounds of the invention and pharmaceutically acceptable carriers or diluents therefor. Additional aspects of the invention provide methods for the inhibition of HIV comprising administering a compound of the formula I to a subject afflicted with or exposed to HIV-1. The HIV-1 may comprise a drug escape mutant, such as HIV strain comprising the mutations at the 100, 103 and/or 181 mutations, especially K103N.

The invention also extends to the use of the compounds of formula I in therapy, such as in the preparation of a medicament for the treatment of HIV infections.

In treating conditions caused by HIV, the compounds of formula I are preferably administered in an amount to achieve a plasma level of around 100 to 5000 nM, such as 300 to 2000 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500-750 mg, in one to four dosage units per day. As with all pharmaceuticals, dosage rates will vary with the size and metabolic condition of the patient as well as the severity of the infection and may need to be adjusted or concomitant medications.

In keeping with the usual practice with HIV inhibitors it is advantageous to co-administer one to three additional antivirals to provide synergistic responses and to ensure complementary resistance patterns. Such additional antivirals may include AZT, ddI, ddC, D4T, 3TC, DAPD, alovudine, abacavir, adefovir, adefovir dipivoxil, bis-POC-PMPA, GW420 867X, foscamet, hydroxyurea, Hoechst-Bayer HBY 097, efavirenz, trovirdine, capravirine, nevirapine, delaviridihe, tipranavir, emtricitabine, PFA, H2G (omaciclovir), MIV-606 (valomaciolovir stearate), TMC-126, TMC-125, TMC-120, efavirenz, DMP-450, loviride, ritonavir, (including kaletra), lopinavir, saquinavir, lasinavir, indinavir, amprenavir, amprenavir phosphate, nelfinavir and the like, typically at molar ratios reflecting their respective activities and bioavailabilities. Generally such ratio will be of the order of 25:1 to 1:25, relative to the compound of formula I, but may be lower, for instance in the case of cytochrome antagonists such as ritonavir.

Compounds of the invention are typically prepared as follows:

Scheme 1

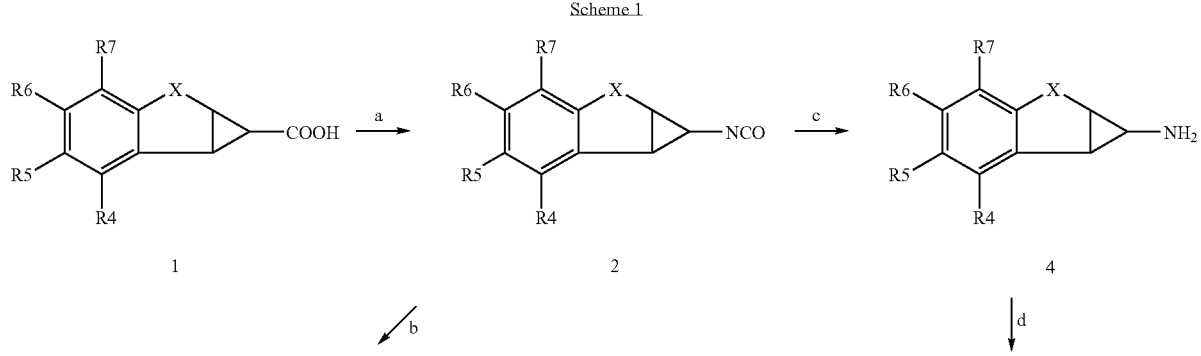

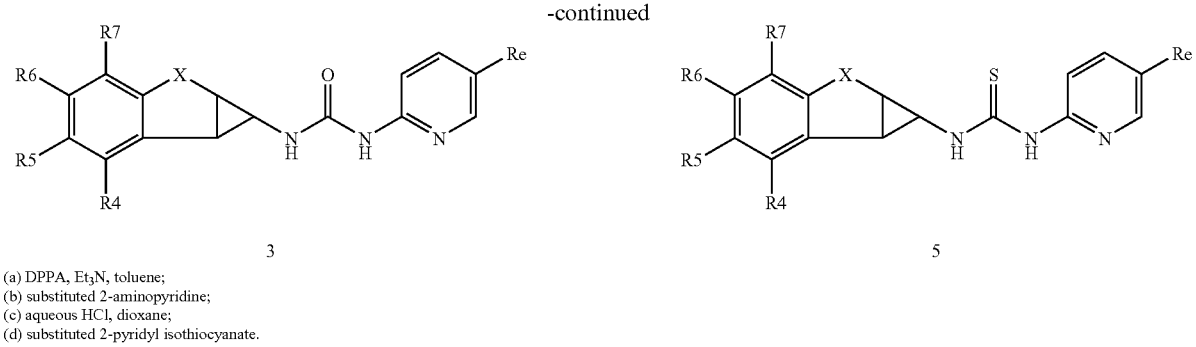

(a) DPPA, Et₃N, toluene;
(b) substituted 2-aminopyridine;
(c) aqueous HCl, dioxane;
(d) substituted 2-pyridyl isothiocyanate.

Compounds of the general formula (I), wherein $R_1$ is O (urea) or S (thiourea), $R_2$ is, for instance, a 5-substituted pyrid-2-yl (Re is the $(CHR_{11})_p$-E-$(CHR_{11})_q$—$R_{10}$ moiety), and $R_3$ is H, are prepared by methods shown in Scheme 1. The cyclopropanecarboxylic acid 1-Scheme-1 is converted to the acyl azide and heated to 120° C. to induce Curtius rearrangement and provide the isocyanate 2-Scheme-1. The urea 3-Scheme-1 is obtained by-coupling of the isocyanate with the relevantly substituted 2-aminopyridine. Hydrolysis of the isocyanate as in step (c) which results in the cyclopropylamine 4-Scheme-1, followed by reaction with a 2-pyridyl isothiocyanate provides the thiourea 5-Scheme-1. The isothiocyanate may be prepared from the optionally ring substituted 2-aminopyridine by known methods, such as treatment with thiophosgene or thiocarbonyidiimidazole. $R_3$ variants of formula I are prepared correspondingly using the appropriately amine-substituted amino-$R_2$, ie 2-(N-methylamino)pyridine for $R_3$ as methyl. Many 2-aminopyridines are commercially available and others are described in literature, for example those shown in Scheme 2. $R_1$=S compounds can alternatively be prepared from the isothiocyanate corresponding to 2-Scheme 2 or from amine 3-Scheme 2 and amino-$R_2$ in conjunction with an RC(=S)R' both as described in WO 9303022. Although Scheme 1 has been illustrated with a substituted pyridyl it is readily apparent that corresponding couplings can be used for other $R_2$ variants such as (—$CHR_{11}$)$_p$-E-$(CHR_{11})_q$—$R_{10}$)-substituted thiazolyl, pyrazinyl, benzothiazolyl, pyrimidinyl etc.

Scheme 2

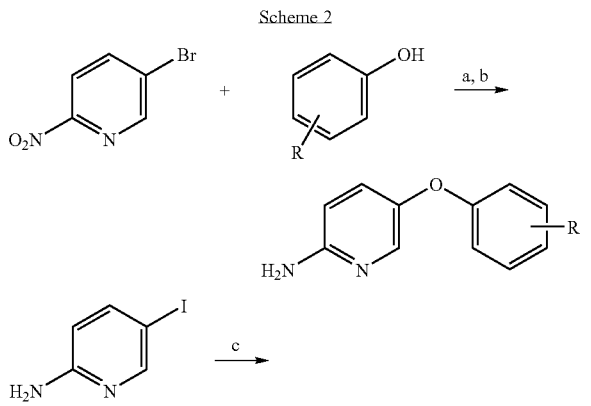

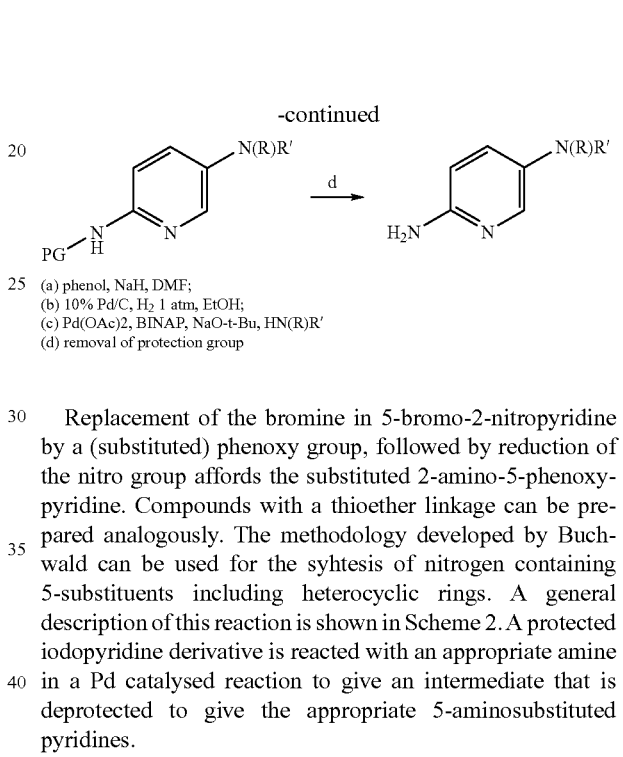

(a) phenol, NaH, DMF;
(b) 10% Pd/C, H₂ 1 atm, EtOH;
(c) Pd(OAc)2, BINAP, NaO-t-Bu, HN(R)R'
(d) removal of protection group Replacement of the bromine in 5-bromo-2-nitropyridine by a (substituted) phenoxy group, followed by reduction of the nitro group affords the substituted 2-amino-5-phenoxypyridine. Compounds with a thioether linkage can be prepared analogously. The methodology developed by Buchwald can be used for the syhtesis of nitrogen containing 5-substituents including heterocyclic rings. A general description of this reaction is shown in Scheme 2. A protected iodopyridine derivative is reacted with an appropriate amine in a Pd catalysed reaction to give an intermediate that is deprotected to give the appropriate 5-aminosubstituted pyridines.

Scheme 3

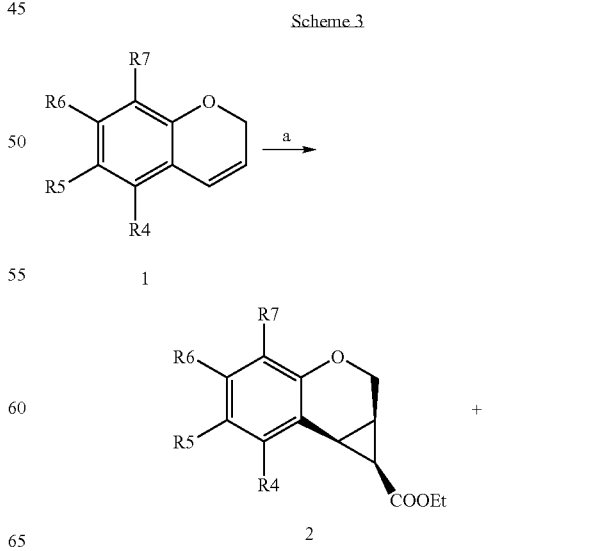

-continued

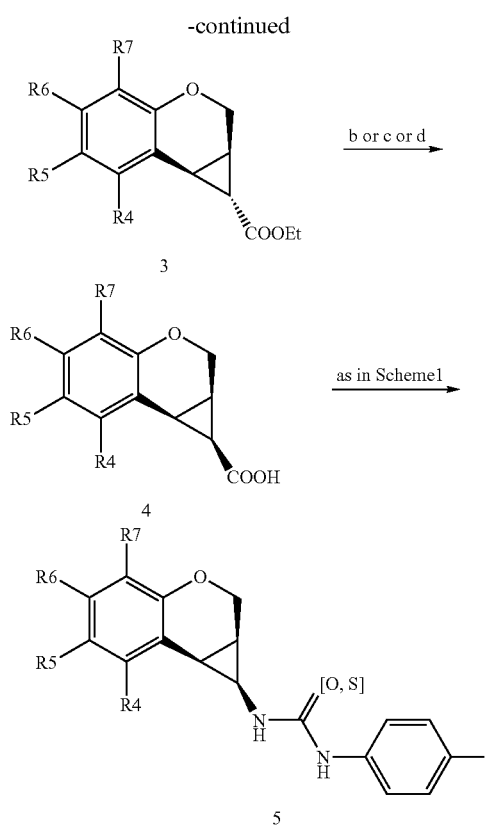

(a) ethyl diazoacetate, catalyst, CH₂Cl₂;
(b) chromatography and then reflux with LiOH, H₂O, MeOH;
(c) reflux with LiOH, H₂O, MeOH and then chromatography;
(d) rt, NaOH, H₂O, MeOH and then reflux with LiOH, H₂O, MeOH Compounds of the general formula (I), wherein R1 is O (urea) or S (thiourea), R2 is, for example, a 5-substituted pyrid-2-yl, R3 is H, X is -D-CH₂, and wherein the cyclopropyl moiety has the relative configuration

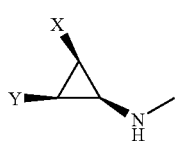

are prepared by methods shown in Scheme 3. Cyclopropanation of the double bond in the chromene 1-Scheme-3 with ethyl diazoacetate is catalyzed by cuprous or rhodium(II) salts such as CuI, (CuOTf)₂-benzene, and Rh₂(OAc)₄ in solvents such as dichloromethane, 1,2-dichloroethane, or chloroform. The reaction provides a diastereomeric mixture of the cyclopropanecarboxylic acid ethyl esters 2-Scheme-3, with the all cis relative configuration, and its trans isomer 3-Scheme-3. Separation by column chromatography of the cis and trans diastereomers may be accomplished at this stage, followed by hydrolysis of the isolated 2-Scheme-3, such as by refluxing in aqueous methanolic LiOH, to yield a racemic mixture of the all cis cyclopropanecarboxylic acid 4-Scheme-3, as described in step (b). Alternatively, the diastereomeric mixture of ethyl esters may be subjected to hydrolysis, and separation conducted on the mixture of cyclopropanecarboxylic acids to provide the isolated all cis isomer, as in step (c). Step (d) involves isolation of the cis ethyl ester 2-Scheme-3 which may also be done by selective hydrolysis of the trans 3-Scheme-3 at lower temperatures, such as treatment with aqueous methanolic NaOH at ambient temperature. The isolated cis ethyl ester may then be hydrolyzed in the usual manner to the cyclopropanecarboxylic acid 4-Scheme-3. The cyclopropanecarboxylic acid is subjected to the methods outlined in Scheme 1 to obtain the urea or thiourea 5-Scheme-3. The chromenes 1-Scheme-3 are prepared by methods shown in Schemes 4, 5, and 6.

Although this scheme 3 has been illustrated with a D=O variant it will be apparent that corresponding manipulations will be available to the D=S, S=O; S(=O)₂ and D=NR₈ variants. When R₈ is H, the nitrogen is typically protected with a conventional secondary amine protecting group, such as those described in Greene & Wuts Protective Groups in Organic Synthesis 2$^{nd}$ ed, Wiley NY 1991).

Scheme 4

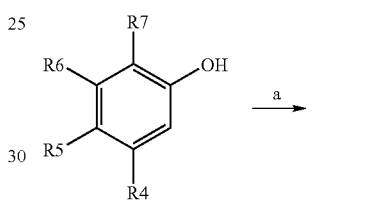

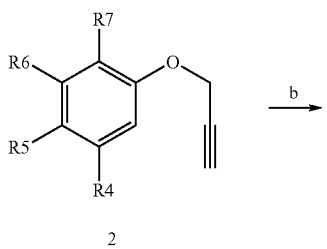

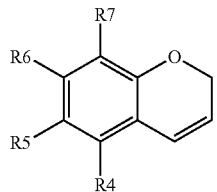

(a) 3-bromopropyne, K₂CO₃, acetone;
(b) N,N-diethylaniline or PEG-200, 225° C.

Scheme 4 describes the preparation of chromenes, including many from commercially available disubstituted phenols, such as those wherein the substitution pattern in the benzene ring is as follows: R4 and R7 are halo; R4 and R6 are halo; R5 and R7 are halo; R4 is halo and R7 is $C_{1-3}$ alkylcarbonyl; and R4 is hydroxy while R5 is $C_{1-3}$ alkylcarbonyl. Reaction of the available disubstituted phenol 1-Scheme-4 with 3-bromopropyne in the presence of a base, such as $K_2CO_3$ in acetone or NaH in DMF, results in nucleophilic substitution of the halide to provide the ether 2-Scheme-4. Ring closure may be accomplished by heating the ether in N,N-dimethylaniline or polyethylene glycol to yield the chromene 3-Scheme-4.

-continued

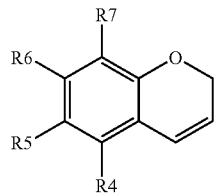

(a) NaBH$_4$, EtOH;
(b) p-toluenesulfonic acid, toluene, reflux;

Scheme 5 describes the preparation of chromenes used as starting material in Scheme 3, from the appropriately substituted chromanones, which are readily accessed from commercially available chromanones, for example those wherein one of the positions in $R_4$ to $R_7$ is substituted with halo or $C_{1-3}$ alkoxy. Conversion of the carbonyl group in 4-chromanone 1a-Scheme-5 and to the correponding alcohol by a suitable reducing agent such sodium borohydride in ethanol provides 2-Scheme-5. Refluxing the alcohol with small amounts of acid, such as p-TsOH in toluene, causes dehydration of 2-Scheme-5 to the desired chromene 1-Scheme-3. Corresponding manipulations will be available for other D variants. For example the corresponding 2H-1-benzothiopyran is readily prepared from commercially available (substituted) thiochroman-4-ones by reaction with a reductant such as a metal hydride for example lithium aluminium hydride in an organic solvent such as ether, followed by dehydration such as refluxing with an acid for example potassium acid sulphate or the like.

Scheme 5

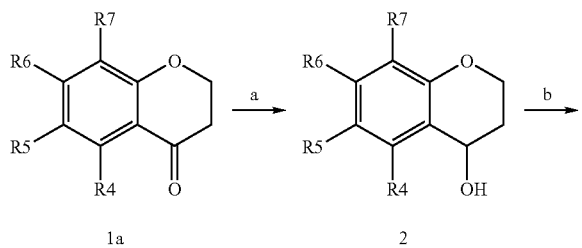

Scheme 6

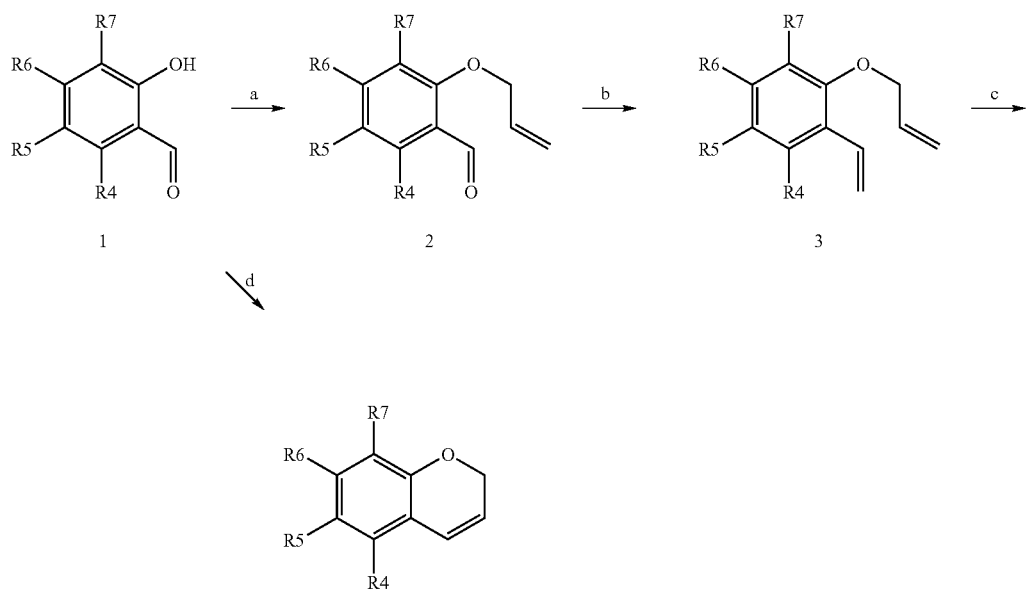

(a) allyl bromide, K$_2$CO$_3$, acetone;
(b) Ph$_3$PCH$_3$Br, NaH, THF;
(c) Cl$_2$[Pcy$_3$]$_2$Ru CHPh, CH$_2$Cl$_2$
(d) Ph$_3$P$^+$CH═CH$_2$ Br$^-$, DBU Chromenes, for use as starting material in Scheme 3, are prepared from substituted o-hydroxybenzaldehydes as shown by methods outlined in Scheme 6. Reaction of 1-Scheme-6 with allyl bromide in the presence of a base such as $K_2CO_3$ in acetone, results in nucleophilic substitution of the halide to provide the ether 2-Scheme-6. Witting reaction transforms the aldehydic group into the olefin and provides 3-Scheme-6. The pair of terminal double bonds may undergo metathesis intramolecularly by treatment with a catalyst such as the ruthenium complex Grubb's catalyst in step (c) to produce the chromene. Alternatively 1-Scheme-6 can be cyclised directly as shown in step d) in the legend above.

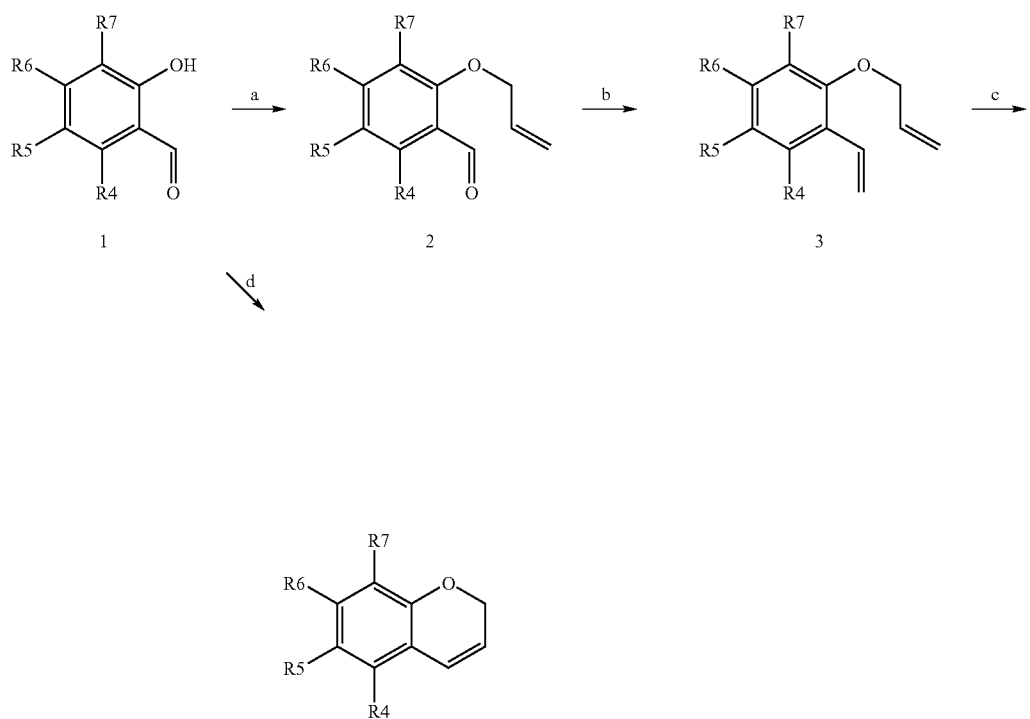

Scheme 6

(a) allyl bromide, $K_2CO_3$, acetone;
(b) $Ph_3PCH_3Br$, NaH, THF;
(c) $Cl_2[Pcy_3]_2Ru$ CHPh, $CH_2Cl_2$
(d) $Ph_3P^+CH=CH_2$ $Br^-$, DBU Chromenes, for use as starting material in Scheme 3, are prepared from substituted o-hydroxybenzaldehydes as shown by methods outlined in Scheme 6. Reaction of 1-Scheme-6 with allyl bromide in the presence of a base, such as $K_2CO_3$ in acetone, results in nucleophilic substitution of the halide to provide the ether 2-Scheme-6. Witting reaction transforms the aldehydic group into the olefin and provides 3-Scheme-6. The pair of terminal double bonds may undergo metathesis intramolecularly by treatment with a catalyst such as the ruthenium complex Grubb's catalyst in step (c) to produce the chromene. Alternatively 1-Scheme-6 can be cyclised directly as shown in step d) in the legend above.

Scheme 7

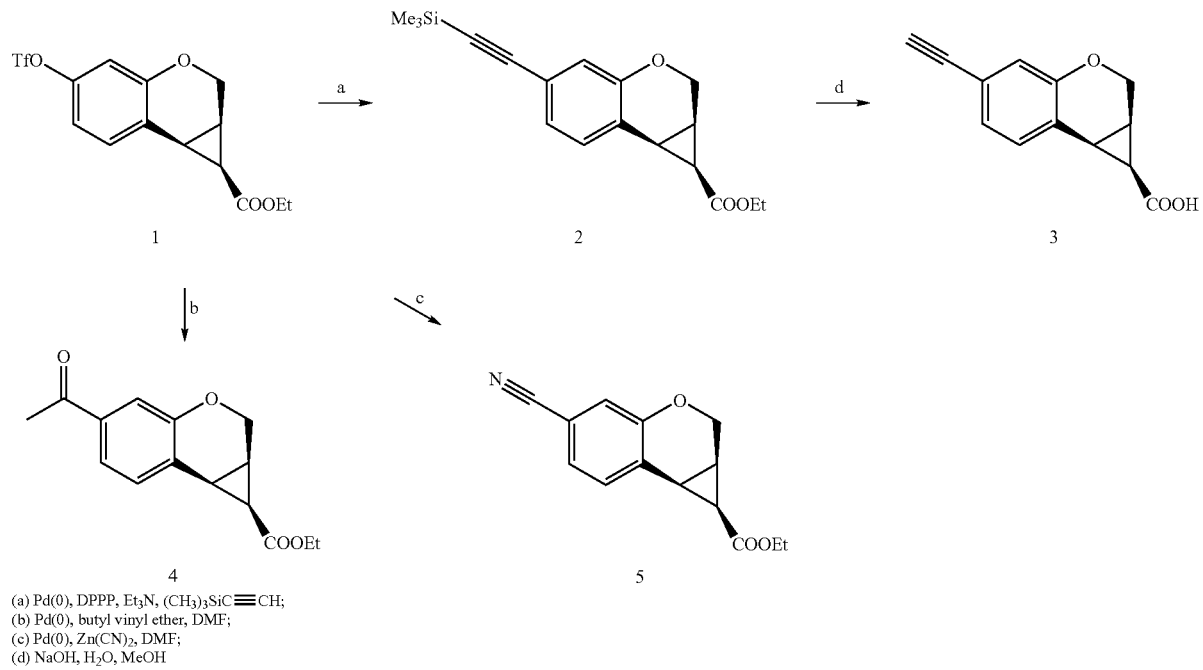

(a) Pd(0), DPPP, Et₃N, (CH₃)₃SiC≡CH;
(b) Pd(0), butyl vinyl ether, DMF;
(c) Pd(0), Zn(CN)₂, DMF;
(d) NaOH, H₂O, MeOH Pd(0) catalyzed coupling of the triflate 1-Scheme-7 leads to the replacement of the trifluoromethanesulfonyloxy group and the introduction of other substitutents at $R_6$. Thus, Scheme 7 provides the preparation of synthesis intermediates for use in scheme 3 to give the urea or thiourea 5-Scheme-3 wherein $R_6$ is cyano, ethynyl, or $C_{1-3}$ alkylcarbonyl.

Scheme 8

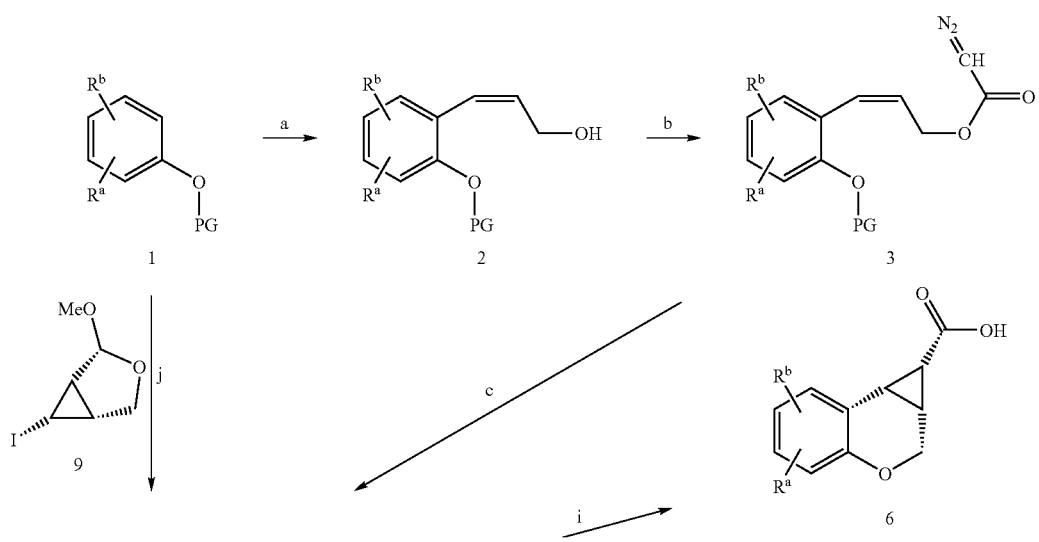

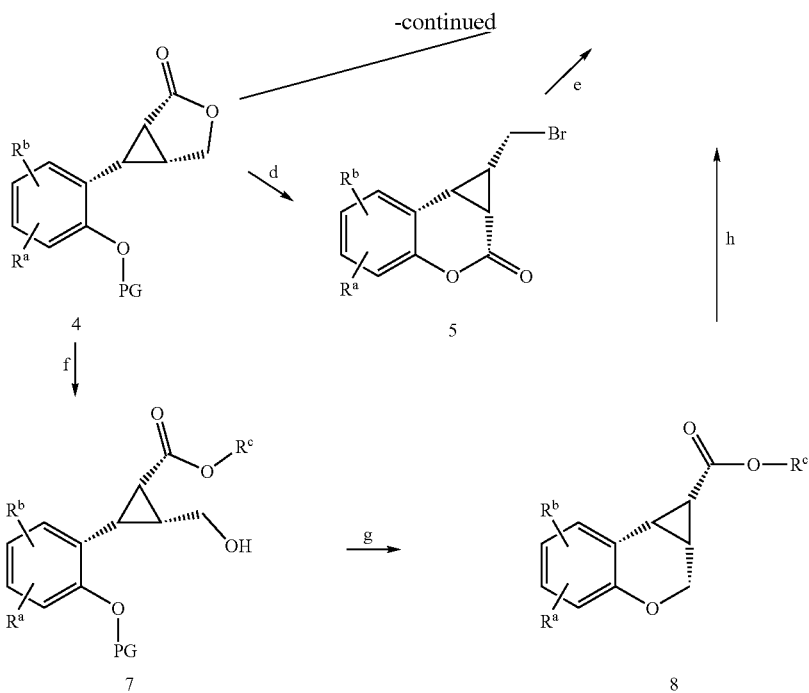

(a) BuLi/ZnCl$_2$, THF; Pd(OAc)$_2$, BrCH═CHCOOEt; DIBAL
(b) TsNHN═CHCOCl; PhNMe$_2$, NEt$_3$, CH$_2$Cl$_2$
(c) Rh$_2$(5-R-MEPY)$_4$, abs degassed dichloromethane
(d) 30% HBr, AcOH
(e) NaOH, H$_2$O
(f) NaOH; CO$_2$; I-PrI/DMSO
(g) IPrOH, HCl; DEAD, PPh$_3$, THF
(h) NaOH, MeOH:H$_2$O
(i) 1. BBr$_3$, CH$_2$Cl$_2$ 2. CH$_3$CN 3. NaOH, water
(j) 1. BuLi/ZnCl$_2$, THF; Pd(OAc) 2. cpd 9-Scheme-8 3. Jones reagent (chromic acid, sulfuric acid in acetone)

Convenient routes to compounds wherein X is —CH$_2$—O— are depicted in Scheme 8, where R$^a$ and R$^b$ are optional substituents R$_4$-R$_7$, which are suitably protected with conventional protecting groups as necessary and R$^c$ is a lower alkyl ester. Optionally substituted phenol 1-Scheme-8 which is hydroxy-protected with a protecting group such as methyl, MOM and the like is reacted with a base such as BuLi or the like in a solvent such as THF or the like and transformed to zinc salt by adding-zinc chloride or the like. A catalyst such as Pd(OAc)$_2$ or the like is added along with an activated acrvlate such as lower alkyl-cis-3-haloacrylate, for example BrCH═CHCOOEt or the like. The reaction mixture is cooled and a reducing agent such as DIBAL or the like is added portionwise and quenched to yield 2-Scheme-8. A hydrazone such as the p-toluenesulfonylhydrazone of glyoxylic acid chloride or the like and a base such as N,N-dimethylaniline or the like is added in a solvent such as CH$_2$Cl$_2$ or the like followed by the addition of another base such as Et$_3$N or the like to yield 3-Scheme-8. The reaction product is dissolved in a solvent-such as dichloromethane or the like which is preferably degassed. A chiral Doyle's catalyst such as Rh$_2$(5-R-MEPy)$_4$ (U.S. Pat. No. 5,175,311, available from Aldrich or Johnson Matthey), or the like is added to yield 4-Scheme-8 in a high enantiomeric excess such as greater than 80, preferably greater than 90% ee. Preferably, this compound is first reacted with BBr$_3$ in dichloromethane followed by the addition of acetonitrile the reaction mixture and finally sodiumhydroxide is added to give 6-Scheme-8. Alternatively, this product (4-Scheme-8) is ring-opened with an electrophile preferably HBr or the like under in conjunction with an acid such as AcOH or the like. Under acid conditions a spontaneous ring closure takes place to form chromenone 5-Scheme-8. When subjected to basic conditions such as NaOH or the like, the chromenone rearranges to form the chromencyclopropylcarboxylic acid 6-Scheme-8. Alternatively, 4-Scheme-8, for instance when the phenolic protecting group is MOM, can be subjected to basic conditions such as NaOH, carbon dioxide and a lower alkyl halide such as iPrI in a solvent such as DMSO to open the lactone and yield the alkyl ester 7-Scheme-8. Displacement of the hydroxy protecting group and ring closure with the free hydroxymethyl moiety occurs in acidic conditions such as iPrOH/HCl or the like followed by DEAD; PPH$_3$ in an organic solvent such as THF or the like. Alternatively, in a convergent approach, compound 1-Scheme-8 is reacted with BuLi and transformed to a zinc salt. This salt reacted with the cyclopropyliodide, 9-Scheme-8, in a palladium-catalyzed reaction to give after reaction with Jone's reagent compound 4-Scheme-8. This carboxylic acid is in turn converted to the isocyanate as shown in Scheme 1 and subsequently to the heteroarylurea or heteroaryithiourea of the Formula I.

EINBETTEN

R$_3$ variants of formula I are prepared correspondingly using the appropriately amine-substituted amino-R$_2$, is 5-substitued-2-(N-methylamino)pyridihe derivatives for R$_3$ as methyl. Although Scheme 1 has been iilustrated with a substituted pyrdyi it is readily apparent that corresponding couplings can be used for other $R_2$ variants such as substituted thiazolyl, pyrazinyl, benzothiazolyl, pyrimidinyl, etc.

EINBETTENEINEBETTENEINBETTEN

Compounds wherein X is an optionally substituted alkylene are conveniently prepared by scheme 9:

Scheme 9

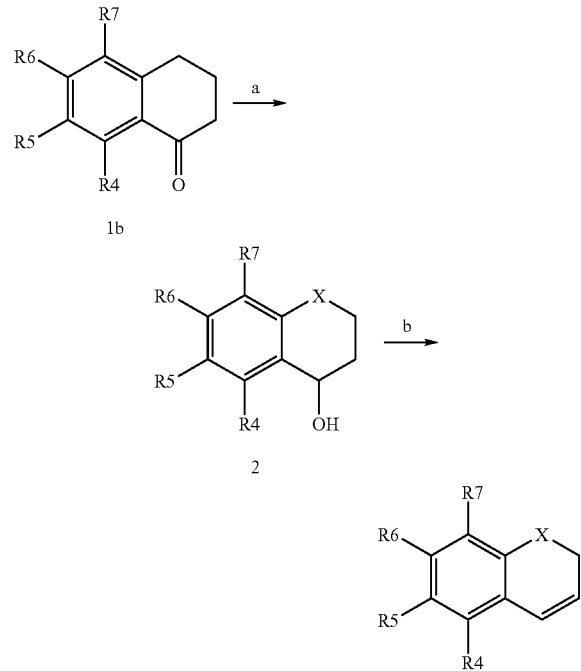

(a) $NaBH_4$, EtOH;
(b) p-toluenesulfonic acid, toluene, reflux;

Scheme 9 describes the preparation of tetralins, indanes and homologues, used as starting material in the schemes above from known monosubstituted tetralones etc, wherein positions $R_4$ to $R_7$ is/are substituted, for example with halo or $C_{1-3}$ alkoxy. Conversion of the carbonyl group in 1-tetralone 1b-Scheme-9 to the corresponding alcohol by a suitable reducing agent such sodium borohydride in ethanol provides 2-Scheme-9. Refluxing the alcohol with small amounts of acid, such as p-TsOH in toluene, causes dehydration of 2-Scheme-9 to the desired tetralin 1-Scheme-9. Corrresponding reactions are applicable to n=1 or 3.

Favoured compounds of formula I include
(−)-cis-1-(5-(pyrid-3-yloxy)-pyridin-2-yl)-3-(4,7-difluoro-1,1a,2,7b-tetrahydro-cyclopropa[c]chromene-1-yl)-urea,
(−)-cis-1-(5-(2-fluoropyrid-3-yloxy)-pyridin-2-yl)-3-(4,7-difluoro-1,1a,2,7b-tetrahydro-cyclopropa[c]chromene-1-yl)-urea,
(−)-cis-1-(5-(2-cyano-pyrid-3-yloxy)-pyridin-2-yl)-3-(4,7-difluoro-1,1a,2,7b-tetrahydro-cyclopropa[c]chromene-1-yl)-urea,
(−)-cis-1-(5-(4-fluoropyrid-3-yloxy)-pyridin-2-yl)-3-(4,7-difluoro-1,1a,2,7b-tetrahydro-cycopropa[c]chromene-1-yl)-urea,
(−)-cis-1-(5-(4-cyano-pyrid-3-yloxy)-pyridin-2-yl)-3-(4,7-difluoro-1,1a,2,7b-tetrahydro-cyclopropa[c]chromene-1-yl)-urea,
(−)-cis-1-(5-(5-fluoro-pyrid-3-yloxy)-pyridin-2-yl)-3-(4,7-difluoro-1,1a,2,7b-tetrahydro-cyclopropa[c]chromene-1-yl)-urea,
(−)-cis-1-(5-(5-cyano-pyrid-3-yloxy)-pyridin-2-yl)-3-(4,7-difluoro-1,1a,2,7b-tetrahydro-cryclopopa[c]chromene-1-yl)-urea,
(−)-cis-1-(5-(pyrid-3-yloxy)-pyridin-2-yl)-3-(4,7-difluoro-1,1a,2,7b-tetrahydro-cyclopropa[c]chromene-1-yl)-urea,
(−)-cis-1-(5-(2-fluoropyrid-3-yloxy)-pyridin-2-yl3-(4,7-difluoro-1,1a,2,7b-tetrahydro-cyclopropa[c]chromene-1-yl)-urea,
(−)-cis-1-(5-(2-cyanopyrid-3-yloxy)-pyridin-2-yl)-3-(4,7-difluoro-1,1a,2,7b-tetrahydro-cyclopropa[c]chromene-1-yl)-urea,
(−)-cis-1-(5-(4-fluoropyrid-3-yloxy)-pyridin-2-yl)-3-(4,7-difluoro-1,1a,2,7b-tetrahydro-cyclopropa[c]chromene-1-yl)-urea,
(−)-cis-1-(5-(4-cyanopyrid-3-yloxy)-pyridin-2-yl)-3-(4,7-difluoro-1,1a,2,7b-tetrahydro-cyclopropa[c]chromene-1-yl)urea.
(−)-cis-1-(5-(5-fluoropyrid-3-yloxy)-pyridin-2-yl)-3-(4,7-difluoro-1,1a,2,7b-tetrahydro-cyclopropa[c]chromene-1-yl)-urea,
(−)-cis-1-(5-(5-cyanopyrid-3-yloxy)-pyridin-2-yl)-3-(4,7-difluoro-1,1a,2,7b-tetrahydro-cyclopropa[c]chromene-1-yl)-urea,
(−)-cis-1-(5-(pyridin-4-yloxy)-pyridin-2-yl)-3-(4,7-difluoro-1,1a,2,7b-tetrahydro-cyclopropa[c]chromene-1-yl)-urea,
(−)-cis-1-(5-(3-fluoropyrid-4-yloxy)pyridin-2-yl)-3-(4,7-difluoro-1,1a,2,7b-tetrahydro-cyclopropa[c]chromene-1-yl)-urea,
(−)-cis-1-(5-(3-cyano-pyrid-4-yloxy)-pyridin-2-yl)-3-(4,7-difluoro-1,1a,2,7b-tetrahydro-cyclopropa[c]chromnene-1-yl)-urea,
(−)-cis-1-(5-(2-fluoropyrid-4-yloxy)-pyridin-2-yl)-3-(4,7-difluoro-1,1a,2,7b-tetrahydro-cyclopropa[c]chromene-1-yl)-urea,
(−)-cis-1-(5-(2-cyanopyrid-4-yloxy)-pyridin-2-yl)-3-(4,7-difluoro-1,1a,2,7b-tetrahydro-cyclopropa[c]chromene-1-yl)-urea,
(−)-cis-1-(5-(pyrid-4-yloxy)-pyridin-2-yl)-3-(4,7-difluoro-1,1a,2,7b-tetrahydro-cyclopropa[c]chromene-1-yl)-urea,
(−)-cis-1-(5-(3-fluoropyrid-4-yloxy)-pyridin-2-yl)-3-(4,7-difluoro-1,1a,2,7b-tetrahydro-cyclopropa[c]chromene-1-yl)-urea,
(−)-cis-1-(5-(3-cyanopyrid-4-yloxy)-pyridin-2-yl)-3-(4,7-difluoro-1,1a,2,7b-tetrahydro-cyclopropa[c]chromene-1-yl)-urea,
(−)-cis-1-(5-(2-fluoropyrid-4-yloxy)-pyridin-2-yl)-3-(4,7-difluoro-1,1a,2,7b-tetrahydro-cryclopropa[c]chromene-1-yl)-urea,
(−)-cis-1-(5-(2-cyanopyrid-4-yloxy)-pyridin-2-yl)-3-(4,7-difluoro-1,1a,2,7b-tetrahydro-cyclopropa[c]chromene-1-yl)-urea,
(−)-cis-1-(5-(2-cyanophenoxy)-pyridin-2-yl)-3-(4,7-difluoro-1,1a,2,7b-tetrahydro-cyclopropa[c]chromene-1-yl)-urea,
(−)-cis-1-(5-(3-cyanophenoxy)-pyridin-2-yl)-3-(4,7-difluoro-1,1a,2,7b-tetrahydro-cyclopropa[c]chromene-1-yl)-urea,
(−)-cis-1-(5-(4-cyanophenoxy)-pyridin-2-yl)-3-(4,7-difluoro-1,1a,2,7b-tetrahydro-cyclopropa[c]chromene-1-yl)-urea.
(−)-cis-1-(5-(2-fluorophenoxy)-pyridin-2-yl)-3-(4,7-difluoro-1,1a,2,7b-tetrahydro-cyclopropa[c]chromene-1-yl)-urea, (−)-cis-1-(5-(3-fluorophenoxy)-pyridin-2-yl)-3-(4,7-difluoro-1,1a,2,7b-tetrahydro-cyclopropa[c]chromene-1-yl)-urea,
(−)-cis-1-(5-(4-fluorophenoxy)-pyridin-2-yl)-3-(4,7-difluoro-1,1a,2,7b-tetrahydro-cyclopropa[c]chromene-1-yl)-urea,
(−)-cis-1-(5-(2,4-fluorophenoxy)-pyridin-2-yl)-3-(4,7-difluoro-1,1a,2,7b-tetrahydro-cyclopropa[c]chromene-1-yl)-urea,
(−)-cis-1-(5-(2,3-difluorophenoxy)-pyridin-2-yl)-3-(4,7-difluoro-1,1a,2,7b-tetrahydro-cyclopropa[c]chromene-1-yl)-urea,
(−)-cis-1-(5-(2,5-difluorophenoxy)-pyridin-2-yl)-3-(4,7-difluoro-1,1a,2,7b-tetrahydro-cyclopropa[c]chromene1-yl)-urea,
(−)-cis-1-(5-(2,6-difluorophenoxy)-pyridin-2-yl)-3-(4,7-difluoro-1,1a,2,7b-tetrahydro-cyclopropa[c]chromene-1-yl)-urea,
(−)-cis-1-(5-(3,5-difluorophenoxy)-pyridin-2-yl)-3-(4,7-difluoro-1,1a,2,7b-tetrahydro-cyclopropa[c]chromene-1-yl)-urea,
(−)-cis-1-(5-(3,4-difluorophenoxy)-pyridin-2-yl)-3-(4,7-difluoro-1,1a,2,7b-tetrahydro-cyclopropa[c]chromene-1-yl)-urea,
(−)-cis-1-(5-(2-fluoro-3-cyanophenoxy)-pyridin-2-yl)-3-(4,7-difluoro-1,1a,2,7b-tetrahydro-cyclopropa[c]chromene-1-yl)-urea,
(−)-cis-1-(5-(3-fluoro-2-cyanophenoxy)-pyridin-2-yl)-3-(4,7-difluoro-1,1a,2,7b-tetrahydro-cyclopropa[c]chromene-1-yl)-urea,
(−)-cis-1-(5-(3-fluoro-4-cyanophenoxy)-pyridin-2-yl)-3-(4,7-difluoro-1,1a,2,7b-tetrahydro-cyclopropa[c]chromene-1-yl)-urea,
(−)-cis-1-(5-(4-fluoro-3-cyanophenoxy)-pyridin-2-yl)-3-(4,7-diflubro-1,1a,2,7b-tetrahydro-cyclopropa[c]chromene-1-yl)-urea,
(−)-cis-1-(5-(3-fluoro-5-cyanophenoxy)-pyridin-2-yl)-3-(4,7-difluoro-1,1a,2,7b-tetrahydro-cyclopropa[c]chromene-1-yl)-urea,
(−)-cis-1-(5-(5-fluoro-3-cyanophenoxy)-pyridin-2-yl)-3-(4,7-difluoro-1,1a,2,7b-tetrahydro-cyclopropa[c]chromene-1-yl)-urea,
(−)-cis-1-(5-(4-fluoro-2-cyanophenoxy)-pyridin-2-yl)-3-(4,7-difluoro-1.1a,2,7b-tetrahydro-cyclopropa[c]chromene-1-yl)-urea,
(−)-cis-1-(5-(2-fluoro-4-cyanophenoxy)-pyridin-2-yl)-3-(4,7-difluoro-1,1a,2,7b-tetrahydro-cyclopropa[c]chromene-1-yl)-urea,
(−)-cis-1-(5-(5-fluoro-2-cyanophenoxy)-pyridin-2-yl)-3-(4,7-difluoro-1,1a,2,7b-tetrahydro-cyclopropa[c]chromene-1-yl)-urea,
(−)-cis-1-(5-(2-fluoro-5-cyanophenoxy)-pyridin-2-yl)-3-(4,7-difluoro-1,1a,2,7b-tetrahydro-cyclopropa[c]chromene-1-yl)-urea,
(−)-cis-1-(5-(6-fluoro-2-cyanophenoxy)-pyridin-2-yl)-3-(4,7-difluoro-1,1a,2,7b-tetrahydro-cyclopropa[c]chromen-1-yl)-urea,
(−)-cis-1-(5-(2-fluoro-6-cyanophenoxy)-pyridin-2-yl)-3-(4,7-difluoro-1,1a,2,7b-tetrahydro-cyclopropa[c]chromene-1-yl)-urea, and the corresponding thioureas of each of these compounds;
and pharmaceutically acceptable salts thereof, especially enantiomerically enriched, for example greater than 80% by weight, preferably >90%, such as >97% ee or pure preparations comprising the (−) enantiomer.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formualtions include those suitable for rectal nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

DETAILED DESCRIPTION

Various aspects of the invention will now be illustrated by way of example only with reference to the following non-limiting examples.

EXAMPLE 1

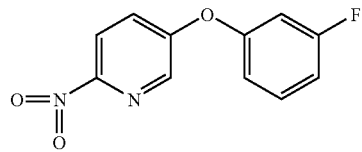

5-(3-flurophenoxy)-2-nitropyridine

Sodium hydride (60% dispersion in mineral oil, 0.11 g, 2.7 mmol) was mixed with 3-5 ml of dry dimethylformamide and 3-fluorophenol (0.244 ml, 2.7 mmol) was added to the stirred suspension. When the gas evolution was ceased the reaction mixture was heated at stirring at 60° C. and 5-bromo-2-nitropyridine (0.5 g, 2.5 mmol) was added to the reaction mixture in one portion. The reaction-mixture was stirred at 60° C. for about 12 hours. The reaction mixture was then mixed with 50 ml of water and extracted into methylene chloride (3×20 ml). Organic extract was washed with water and brine, dried over magnesium sulfate and concentrated by rotary evaporation. The resulting mixture was purified by column chromatography on silica (30 g, EtOAc/hexane 1:3) to give 190 mg (33% yield) of desired product.

¹H-NMR (CDCl₃): 8.31 (d, 1H), 8.24 (d, 1H), 7.38 (dd, 1H), 7.08-7.20 (m, 4H).

EXAMPLE 2

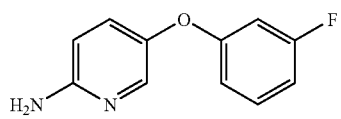

5-(3-fluorophenoxy)-2-pyridinamine 5-(3-fluorophenoxy)-2-nitropyridine was mixed with 15-20 ml of ethanol and bubbled with argon. About 20 mg of Pd/C was added to the reaction mixture and hydrogen gas was applied at normal pressure and ambient temperature for 3-12 h. The reaction was monitored by TLC. After the reaction was complete, the reaction mixture was bubbled with argon, filtered through Celite and the solution obtained was concentrated by rotary evaporation to give 165 mg of desired aminopyridine (quantitative yield).

¹H-NMR (CDCl₃): 7.92 (d, ~1H), 7.22 (m, 2H), 6.73 (m, 2H), 6.62 (d tr, 1H), 6.54 (d, 1H), 6.82 (dd, 2H), 6.64 (d, 1H), 4.42 (br s, 2H).

EXAMPLE 3

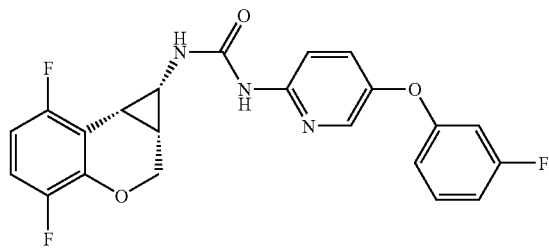

N-[(1S,1aR,7bR)-4,7-difluoro-1,1a,2,7b-tetrahydro-cyclopropa[c]chromen-1-yl]-N'-[5-(3-fluorophenoxy)-2-pyridinyl]urea (1S,1aR,7bS)-4,7-difluoro-1,1a,2,7b-tetrahydrocyclopropa[c]chromene-1-carboxylic acid (50 mg, 0.22 mmol, ~95% ee) was mixed with toluene (1,5 ml), triethylamine (1.1 eq), 5-(3-fluorophenoxy)-2-aminopyridine (1.1 eq), DPPA (1.1 eq) and bubbled with argon for about 5 min. The reaction mixture was then heated at stirring at 110° C. for 3 h under in a closed vial. The reaction mixture was concentrated by mtary evaporation and purified by column chromatography on silica (30 g, ethylacetate/hexane 1:1). Desired product was obtained as beige-white powder (60 mg, yield 64%).

¹H-NMR (CDCl₃): 9.57 (br s, 1H), 9.47 (br s, 1H), 7.61 (d, 1H), 7.28 (m, 2H), 6.89 (d, 1H), 6.79 (m, 2H), 6.70 (dd, 1H), 6.64 (d tr, 1H), 6.56 (tr d, 1H), 4.45 (dd, 1H), 4.33 (dd, 1H), 3.80 (q, 1H), 2.59 (br tr, 1H), 1.92-1.99 (m, 1H). LC-MS: M⁺428, M⁻4.26.

EXAMPLE 4

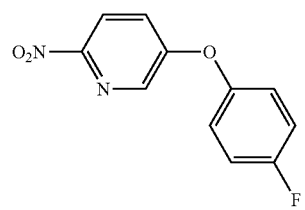

5-(4-fluorophenoxy)-2-nitropyridine 5-(4-Fluorophenoxy)-2-nitropyridine was synthesized analogously to Example 1 from 4-fluorophenol (0.3 g, 2.7 mmol) to give 310 mg of product (54% yield).

¹H-NMR (CDCl₃): 8.31 (d, ~1H), 8.24 (d, 1H), 7.39 (dd, 1H), 7.08-7.22 (m, 4H).

EXAMPLE 5

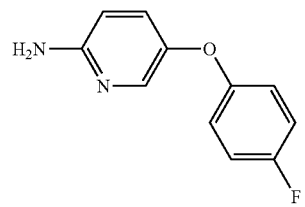

5-(4-fluorophenoxy)-2-pyridinamine 5-(4-Fluorophenoxy)-2-pyridinamine was synthesized analogously to Example 2 from 5-(4-fluorophenoxy)-2-nitropyridine to give 270 mg of product as beige powder.

¹H-NMR (CDCl₃): 7.88 (d, 1H), 7.17 (dd, 2H), 6.99 (m, 2H), 6.89 (m, 2H), 6.52 (d, 1H), 4.42 (br s, 2H).

EXAMPLE 6

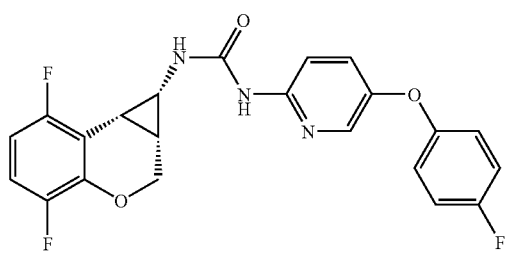

N-[(1S,1aR,7bR)-4,7-difluoro-1,1a,2,7b-tetrahydro-cyclopropa[c]chromen-1-yl]-N'-[5-(4-fluorophenoxy)-2-pyridinyl]urea N-[(1S,1aR,7bR)-4,7-difluoro-1,1a,2,7b-tetrahydrocyclopropa[c]chromen-1-yl]N'-[5-(4-fluorophenoxy)-2-pyridinyl]urea was synthesized analogously to Example 3 from 5-(4-fluorophenoxy)-2-pyridinamine (50 mg, 0.24 mmol) to give 20 mg of pure product as white powder (21% yield).

$^1$H-NMR (CDCl$_3$): 9.40 (br s, 1H), 9.05 (br s, 1H), 7.52 (d, 1H), 7.23 (dd, 1H), 7.00-7.08 (m, 2H), 6.86-6.94 (m, 2H), 6.73-6.82 (m, 2H), 6.56 (d tr, 1H), 6.56 (tr d, 1H), 4.44 (dd, 1H), 4.33 (dd, 1H), 3.78 (q, 1H), 2.59 (br tr, 1H), 1.92-1.99 (m, 1H). LC-MS: M$^+$428, M$^-$426.

EXAMPLE 7

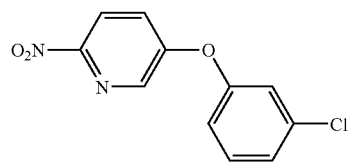

5-(3-chlorophenoxy)-2-nitropyridine 5-(3-Chlorophenoxy)-2-nitropyridine was synthesized analogously to Example 1 from 3-chlorophenol (0.35 g, 2.7 mmol) to give 280 mg of product (45% yield).

$^1$H-NMR (CDCl$_3$): 8.36 (d, 1H), 8.27 (d, 1H), 7.46 (dd, 1H), 7.40 (app dd, 1H), 7.29 (ddd, 1H), 7.02 (ddd, 1H), 7.14 (app dd, 1H).

EXAMPLE 8

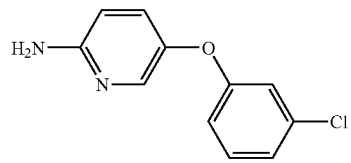

5-(3-chlorophenoxy)-2-pyridinamine 5-(3-Chlorophenoxy)-2-pyridinamine was synthesized analogously to Example 2 from 5-(3-chlorophenoxy)-2-nitropyridine to give 80 mg of white powder after purification by column chromatography on silica (30 g, EtOAc). Yield 32%.

$^1$H-NMR (CDCl$_3$): 7.90 (app dd, 1H), 7.25-7.31 (m, 1H), 7.15-7.22 (m, 2H), 6.98-7.05 (m, 1H), 6.89-6.95 (m, 1H), 6.50 (dd, 1H), 4.42 (br s, 2H).

EXAMPLE 9

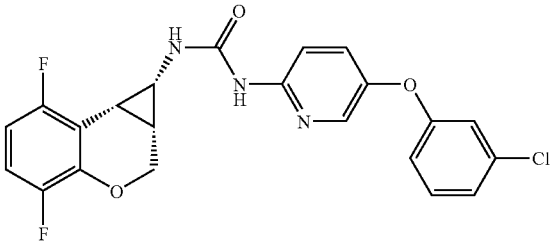

N-[(1S,1aR,7bR)-4,7-difluoro-1,1a,2,7b-tetrahydro-cyclopropa[c]chromen-1-yl]-N'-[5-(3-chlorophenoxy)-2-pyridinyl]urea N-[(1S,1aR,7bR)-4,7-difluoro-1,1a,2,7b-tetrahydrocyclopropa[c]chromen-1-yl]-N'-[5-(3-chlorophenoxy)-2-pyridinyl]urea was synthesized analogously to Example 3 from 5-(3-chlorophenoxy)-2-pyridinamine (54 mg, 0.24 mmol) to give 28 mg of pure product as white powder (28% yield).

$^1$H-NMR (CDCl$_3$): 9.46 (br s, 1H), 9.34 (br s, 1H), 7.59 (d, 1H), 7.23-7.29 (m, ~2H), 7.09 (m, 1H), 6.91 (m, 1H), 6.86 (d, 1H), 6.75-6.84 (m, 2H), 6.56 (d tr, 1H), 4.46 (dd, 1H). 4.33 (dd, 1H), 3.80 (app. q, 1H), 2.59 (br tr, 1H), 1.96 (m, 1H). LC-MS: M$^+$410, M$^-$408.

EXAMPLE 10

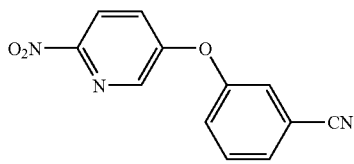

3-[(6-nitro-3-pyridinyl)oxy]benzonitrile 5-(3-Cyanophenoxy)-2-nitropyridine was synthesized analogously to Example 1 from 3-hydroxybenzonitrile (0.32 g, 2.7 mmol) to give solid material after the reaction mixture was mixed with water, which was collected by filtration and washed with ether to give 188 mg of yellow crystals (32% yield).

¹H-NMR (CDCl₃): 8.39 (d, 1H), 8.30 (d, 1H), 7.60 (app. dd, 2H), 7.50 (dd, 1H), 7.42 (m, 1H), 7.35-7.40 (m, 1H).

EXAMPLE 11

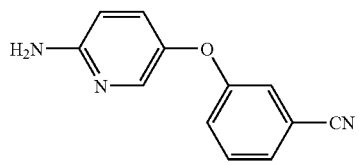

3-[(6-amino-3-pyridinyl)oxy]benzonitrile

3-[(6-amino-3-pyridinyl)oxy]benzonitrile was synthesized analogously to Example 2 from 3-[(6-nitro-3-pyridinyl)oxy]benzonitrile to give 31 mg of beige powder after purification by column chromatography on silica (30 g, EtOAc). Yield 19%.

¹H-NMR (CDCl₃): 7.90 (d, 1H), 7.36-7.41 (m, 1H), 7.32 (d tr, 1H), 7.14-7.22 (m, ~3H), 6.56 (d, 1H), 4.65 (br s, 2H).

EXAMPLE 12

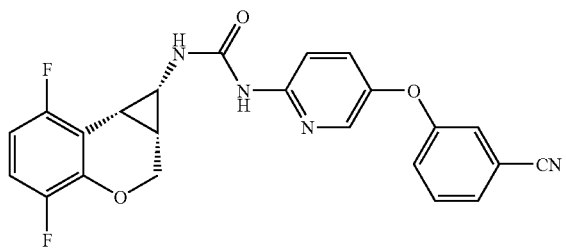

N-[(1S,1aR,7bR)-4,7-difluoro-1,1a,2,7b-tetrahydro-cyclopropa[c]chromen-1-yl]-N'-[5-(3-cyanophenoxy)-2-pyridinyl]urea N-[(1S,1aR,7bR)-4,7-difluoro-1,1a,2,7b-tetrahydrocyclopropa[c]chromen-1-yl]-N'-[5-(3-chlorophenoxy)-2-pyridinyl]urea was synthesized analogously to Example 3 from 3-[(6-amino-3-pyridinyl)oxy]benzonitrile (33 mg, 0.15 mmol). Solid material formed in the reaction mixture was collected by filtration and washed With ethanol to give 15 mg of pure product as slightly beige powder (25% yield).

¹H-NMR (CDCl₃): 9.35 (br s, 1H), 7.65 (br s, 1H), 7.61 (d, 1H), 7.38-7.48 (m, 2H), 7.27 (dd, 1H), 7.16-7.20 (m 2H), 6.78-6.86 (m, 1H), 6.71 (d, 1H), 6.59 (d tr, 1H), 4.48 (dd, 1H), 4.33 (dd, 1H), 3.82 (q, 1H), 2.62 (br tr, 1H), 1.98 (m, 1H). LC-MS: M⁺435, M⁻433.

EXAMPLE 13

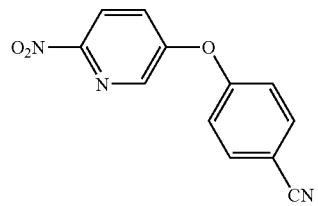

4-[(6-nitro-3-pyridinyl)oxy]benzonitrile 5-(3-Cyanophenoxy)-2-nitropyridine was synthesized analogously to Example 1 from 3-hydroxybenzonitrile (0.7 g, 2.7 mmol) to give 555 mg of product (46% yield).

¹H-NMR (CDCl₃): 8.40 (d, 1H), 8.32 (d, 1H), 7.77 (d, 2H), 7.56 (dd, 1H), 7.20 (app d, 2H). Lc-MS: M⁻300 (+CH₃COO⁻).

EXAMPLE 14

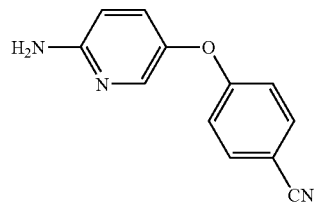

4-[(6-amino-3-pyridinyl)oxy]benzonitrile 5-(3-Chlorophenoxy)-2-pyridinamine was synthesized analogously to Example 2 from 4-[(6-nitro-3-pyridinyl)oxy]benzonitrile (40 mg) to give 31 mg of brown oil.

¹H-NMR (CDCl₃): 7.92 (d, 1H), 7.58 (app d, 2H), 7.21 (dd, 1H), 6.97 (app d, 2H), 6.58 (d, 1H), 4.56 (br s, 2H).

EXAMPLE 16

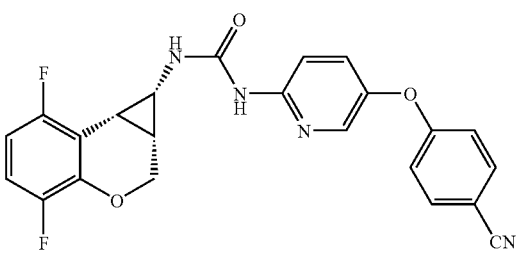

N-[(1S,1aR,7bR)-4,7-difluoro-1,1a,2,7b-tetrahydro-cyclopropa[c]chromen-1-yl]-N'-[5-(4-cyanophenoxy)-2-pyridinyl]urea N-[(1S,1aR,7bR)-4,7-difluoro-1,1a,2,7b-tetrahydrocyclopropa[c]chromen-1-yl]-N'-[5-(3-chlorophenoxy)-2-pyridinyl]urea was synthesized analogously to Example 3 from 3-[(6-amino-3-pyridinyl)oxy]benzonitrile (54 mg, 0.24 mmol) to give 18 mg (yield 31%) of product as white powder after additional purification by preparative HPLC (XTerra MS C18 19×100 mm column, water/acetonitrile with 0.05% trifluoroacetic acid).

$^1$H-NMR (CDCl$_3$): 9.41 (br s, 1H), 9.30 (br s, 1H), 7.66 (d, 1H), 7.63 (app d, 2H), 7.30 (dd, 1H), 6.96 (app d, 2H), 6.89 (d, 1H), 6.75-6.83 (m, 1H), 6.57 (tr d, 1H), 4.48 (dd, 1H), 4.32 (dd, 1H), 3.81 (q, 1H), 2.62 (br tr, 1H), 1.98 (m, 1H).

EXAMPLE 17

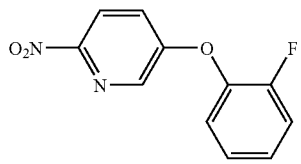

5-(2-fluorophenoxy)-2-nitropnridine 5-(4-Fluorophenoxy)-2-nitropyridine was synthesized analogously to Example 1 from 4-fluorophenol (0.3 g, 2.7 mmol) to give 326 mg of product (57% yield).

$^1$H-NMR (CDCl$_3$): 8.34 (d, 1H), 8.25 (d, 1H), 7.38 (ddd, 1H), 7.22-7.34 (m, 4H).

EXAMPLE 17A

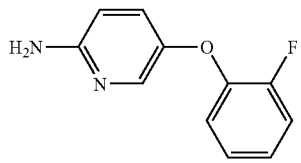

5-(2-fluorophenoxy)-2-pyridinamine 5-(4-Fluorophenoxy)-2-pyridinamine was synthesized analogously to Example 2 from 5-(4-fluorophenoxy)-2-nitropyridine (326 mg) to give 200 mg (70% yield) of product as white crystals after purification by column chromatography on silica (25 g, EtOAc/hexane 1:1).

$^1$H-NMR (CDCl$_3$): 7.90 (d, 1H), 7.10-7.20 (m, 2H), 7.00-7.06 (m, 2H), 6.88-6.95 (m, 1H), 6.50 (d, 1H), 4.55 (br s, ~2H).

EXAMPLE 18

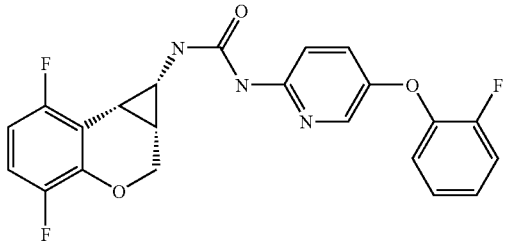

N-[(1S,1aR,7bR)-4,7-difluoro-1,1a,2,7b-tetrahydro-cyclopropa[c]chromen-1-yl]-N'-[5-(2-fluorophenoxy)-2-pyridinyl]urea N-[(1S,1aR,7bR)-4,7-difluoro-1,1a,2,7b-tetrahydrocyclopropa[c]chromen-1-yl]-N'-[5-(4-flurophenoxy)-2-pyridinyl]urea was synthesized analogously to Example 3 from 5-(4-fluorophenoxy)-2-pyridinamine (50 mg, 0.24 mmol) to give 60 mg of pure product as white powder (64% yield).

$^1$H-NMR (CDCl$_3$): 9.40 (br s, ~1H), 9.39 (br s, ~1H), 7.53 (d, 1H), 7.07-7.26 (m, 4H), 6.93-7.00 (m, 1H), 6.84 (d, 1H), 6.74 (app d tr, 1H), 6.53 (tr d, 1H), 4.43 (dd, 1H), 4.33 (dd, 1H), 3.78 (app q, 1H), 2.57 (br tr, 1H), 1.90-1.97 (m, 1H). LC-MS: M$^+$428, M$^-$426.

EXAMPLE 19

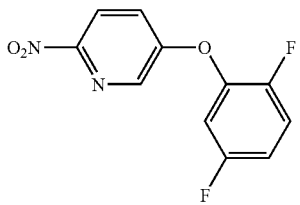

5-(2,5-diflurophenoxy)-2-nitropyridine 5-(4-Fluorophenoxy)-2-nitropyridine was synthesized analogously to Example 1 from 2,5-difluorophenol (0.35 g, 2.7 mmol) to give 400 mg of product (64% yield).

¹H-NMR (CDCl₃): 8.35 (brd, 1H), 8.28 (d, 1H), 7.44 (dd, 1H), 7.24-7.28 (m, 1H), 6.96-7.06 (m, 2H).

EXAMPLE 20

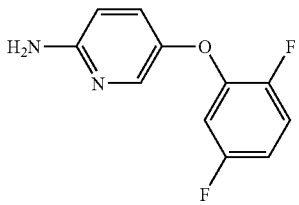

5-(2,5-difluorophenoxy)-2-pyridinamine 5-(4-Fluorophenoxy)-2-pyridinamine was synthesized analogously to Example 2 from 5-(2,5-difluorophenoxy)-2-nitropyridine to give 370 mg of product as beige powder.

¹H-NMR (CDCl₃): 7.92 (d, 1H), 7.21 (dd, 1H), 7.06-7.14 (m, 1H), 6.67-6.74 (m, 1H), 6.56-6.52 (m, 1H), 6.53 (d, 1H), 4.44 (br s, 2H).

EXAMPLE 21

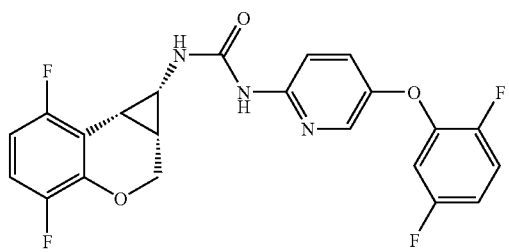

N-[(1S,1aR,7bR)-4,7-difluoro-1,1a,2,7b-tetrahydro-cyclopropa[c]chromen-1-yl]-N'-[5-(2,5-difluorophenoxy)-2-pyridinyl]urea N-[(1S,1aR,7bR)-4,7-difluoro-1,1a,2,7b-tetrahydrocyclopropa[c]chromen-1-yl]-N'-[5-(2,5-difluorophenoxy)-2-pyridinyl]urea was synthesized analogously to Example 3 from 5-(2,5-difluorophenoxy)-2-pyridinamine (55 mg, 0.24 mmol) to give 40 mg of pure product as white powder (41% yield).

¹H-NMR (CDCl₃): 9.50 (br s, 1H), 9.45 (br s, 1H), 7.61 (d, 1H), 7.28 (dd, ~1H), 7.10-7.18 m, 1H), 6.86 (d, 1H), 6.75-6.84 (m, 2H), 6.61-6.66 (m, 1H), 6.56 (tr d, 1H), 4.46 (dd, 1H), 4.32 (dd, 1H), 3.82 (q, 1H), 2.59 (br tr, 1H), 1.93-1.99 (m, 1H). LCMS: M⁺446, M⁻444.

EXAMPLE 22

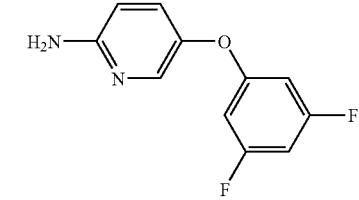

5-(3,5-difluorophenoxy)-2-nitropyridine 5-(3,5-Difluorophenoxy)-2-nitropyridine was synthesized analogously to Example 1 from 3,5-difluorophenol (0.35 g, 2.7 mmol) to give 210 mg of product (34% yield).

¹H-NMR (CDCl₃): 8.38 (d, 1H), 8.30 (d, 1H), 7.55 (dd, 1H), 7.76 (tr tr, 1H), 7.63-6.70 (m, 2H).

EXAMPLE 23

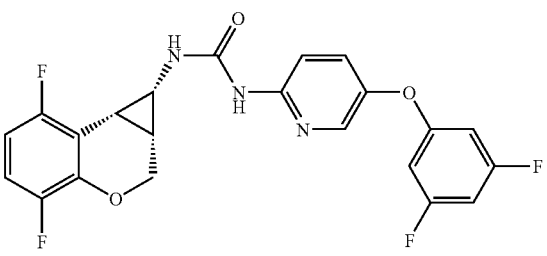

5-(3,5-diflurophenoxy)-2-pyridinamine 5-(3,5-Difluorophenoxy)-2-pyridinamine was synthesized analogously to Example 2 from 5-(3,5-difluorophenoxy)-2-nitropyridine to give about 200 mg of product as brown-beige powder.

¹H-NMR (CDCl₃): 7.92 (d, 1H), 7.19 (dd, 1H), 6.54 (d, 1H), 6.39-6.51 (m, 2H) 4.75 (br s, 2H).

EXAMPLE 24

N-[(1S,1aR,7bR)-4,7-difluoro-1,1a,2,7b-tetrahydro-cyclopropa[c]chromen-1-yl]-N'-[5-(3,5-difluorophenoxy)-2-pyridinyl]urea N-[(1S,1aR,7bR)-4,7-difluoro-1,1a,2,7b-tetrahydrocyclopropa[c]chromen-1-yl]-N'-[5-(2,5-difluorophenoxy)-2-pyridinyl]urea was synthesized analogously to Example 3 from 5-(2,5-difluorophenoxy)-2-pyridinamine (55 mg, 0.24 mmol) to give 60 mg of pure product as white powder (61% yield).

$^1$H-NMR (CDCl$_3$): 9.70 (br s, 1H), 9.45 (br s, 1H), 7.65 (d, 1H), 7.28 (dd, 1H), 6.90 (d, 1H), 6.77-6.85 (m, 1H), 6.51-6.61 (m, 2H), 6.39-6.46 (m, 2H), 4.48 (dd, 1H), 4.32 (dd, 1H), 3.83 (q, 1H), 2.60 (br tr, 1H), 1.94-2.10 (m, 1H).

EXAMPLE 25

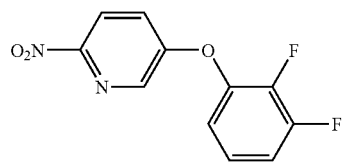

5-(2,3-difluorophenoxy)-2-nitropyridine 5-(2,3-Difluorophenoxy)-2-nitropyridine was synthesized analogously to Example 1 from 2,3-difluorophenol (0.3 g, 2.7 mmol) to give 210 mg of product as white powder (34% yield).

$^1$H-NMR (CDCl$_3$): 8.37 (d, 1H), 8.27 (d, 1H), 7.45 (dd, 1H), 7.13-7.23 (m, 2H), 7.13-7.02 (m, 1H).

EXAMPLE 26

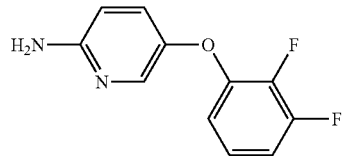

5-(2,3-difluorophenoxy)-2-pyridinamine 5-(2,3-Difluorophenoxy)-2-pyridinamine was synthesized analogously to Example 2 from 5-(2,3-difluorophenoxy)-2-nitropyridine (210 mg) to give 180 mg of product as brown powder.

$^1$H-NMR (CDCl$_3$): 7.92 (d, 1H), 7.20 (dd, 1H), 6.84-6.99 (m, 2H), 6.62-6.68 (m, 1H), 6.52 (dd, 1H), 4.40 (br s, 2H).

EXAMPLE 27

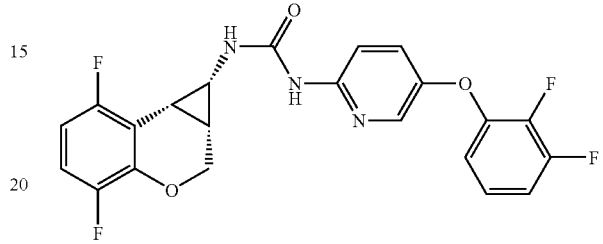

N-[(1S,1aR,7bR)-4,7-difluoro-1,1a,2,7b-tetrahydro-cyclopropa[c]chromen-1-yl]-N'-[5-(2,3-diflurophenoxy)-2-pyridinyl]urea N-[(1S,1aR,7bR)-4,7-difluoro-1,1a, 2,7b-tetrahydrocyclopropa[c]chromen-1-yl]-N'-[5-(2,3-diflurophenoxy)-2-pyridinyl]urea was synthesized analogously to Example 3 from 5-(2,3-difluorophenoxy)-2-pyridinamine (55 mg, 0.24 mmol) to give 50 mg of pure product as white powder (51% yield).

$^1$H-NMR (CDCl$_3$): 9.49 (br s, ~1H), 9.40 (br s, ~1H), 7.58 (d, 1H), 7.27 (dd, ~1H), 9.93-7.06 (m, 2H), 6.86 (d, 1H), 6.74-6.81 (m, 1H), 6.66-6.72 (m, 1H), 6.56 (tr d, 1H), 4.45 (dd, 1H), 4.32 (dd, 1H), 3.82 (q, 1H), 2.59 (br tr, 1H), 1.92-1.99 (m, 1H). LC-MS: M$^+$446, M$^-$444.

EXAMPLE 28

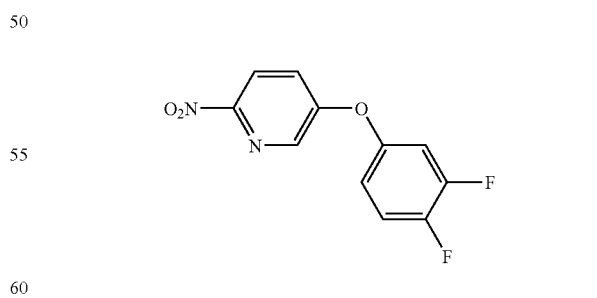

5-(3,4-difluorophenoxy)-2-nitropyridine 5-(3,4-Difluorophenoxy)-2-nitropyridine was synthesized analogously to Example 1 from 3,4-difluorophenol (0.35 g, 2.7 mmol) to give 230 mg of product (37% yield).

¹H-NMR (CDCl₃): 8.33 (d, 1H), 8.27 (d, 1H), 7.44 (dd, 1H), 7.23-7.31 (m, 1H), 6.97-7.03 (m, 1H), 6.85-6.91 (m, 1H).

EXAMPLE 29

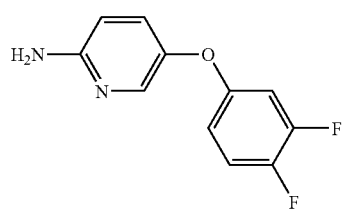

5-(3,4-difluorophenoxy)-2-pyridinamine 5-(3,4-Difluorophenoxy)-2-pyridinamine was synthesized analogously to Example 2 from 5-(3,4-difluorophenoxy)-2-nitropyridine (230 mg) to give 160 mg of product as brown oil.

¹H-NMR (CDCl₃): 7.89 (d, 1H), 7.19 (dd, 1H), 7.07 (app q, 1H), 6.72-6.79 (m, 1H), 6.61-6.67 (m, 1H), 6.54 (d, 1H), 4.46 (br s, 2H).

EXAMPLE 30

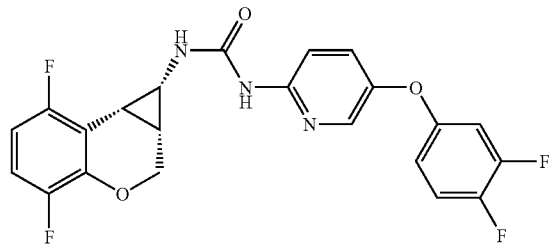

N-[(1S,1aR,7bR)-4,7-difluoro-1,1a,2,7b-tetrahydro-cyclopropa[c]chromen-1-yl]-N'-[5-(3,4-difluorophenoxy)-2-pyridinyl]urea N-[(1S,1aR,7bR)-4,7-difluoro-1,1a,2,7b-tetrahydrocyclopropa[c]chromen-1-yl]-N'-[5-(3,4-difluorophenoxy)-2-pyridinyl]urea was synthesized analogously to Example 3 from 5-(3,4-difluorophenoxy)-2-pyridinamine (55 mg, 0.24 mmol) to give 60 mg of pure product as white powder (61% yield).

¹H-NMR (CDCl₃): 9.50 (br s, ~1H), 9.45 (br s, ~1H), 7.60 (d, 1H), 7.25 (dd, ~1H), 7.12 (app q, 1H), 6.87 (d, 1H), 6.73-6.83 (m, 2H), 6.62-6.68 (m, 1H), 6.56 (tr d, 1H), 4.46 (dd, 1H), 4.32 (dd, 1H), 3.82 (q, 1H), 2.60 (br tr, 1H), 1.93-2.00 (m, 1H). LC-MS: M⁺446, M⁻444.

EXAMPLE 31

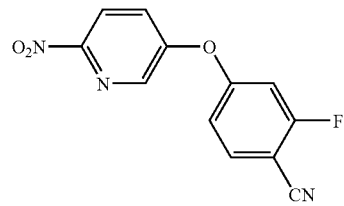

2-fluoro-4-[(6-nitro-3-pyridinyl)oxy]benzonitrile

2-Fluoro-4-[(6-nitro-3-pyridinyl)oxy]benzonitrile was synthesized analogously to Example 1 from 2-fluoro-4-hydroxybenzonitrile (0.37 g, 2.7 mmol) to give 80 mg (13% yield) of product after additional purification by preparative HPLC (XTerra MS C18 19×100 mm column, water/acetonitrile with 0.05% trifluoroacetic acid).

¹H-NMR (CDCl₃): 8.43 (d, 1H), 8.37 (d, 1H), 7.67-7.76 (m, 2H), 6.97-7.04 (m, 2H).

EXAMPLE 32

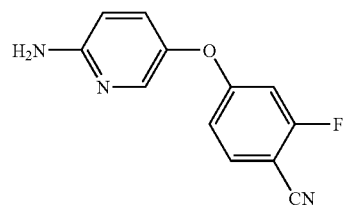

4-[(6-amino-3-pyridinyl)oxy]-2-fluorobenzonitrile

4-[(6-amino-3-pyridinyl)oxy]-2-fluorobenzonitrile was synthesized analogously to Example 2 from 2-fluoro-4-[(6-nitro-3-pyridinyl)oxy]benzonitrile (70 mg) to give 58 mg of product as a dark brown oil.

¹H-NMR (CDCl₃): 7.91 (d, 1H), 7.53 (dd, 1H), 7.21 (dd, 1H), 6.80 (dd, 1H), 6.71 (dd, 1H), 6.59 (d, 1H), 4.70 (br s, 2H).

EXAMPLE 33

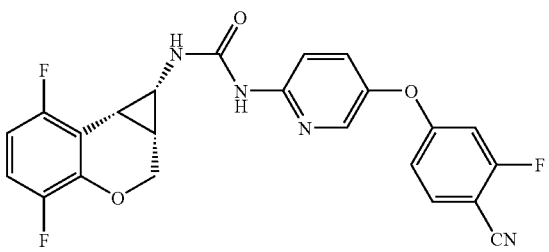

N-[(1S,1aR,7bR)-4,7-difluoro-1,1a,2,7b-tetrahydro-cyclopropa[c]chromen-1-yl]-N'-[5-(4-cyano-3-fluorophenoxy)-2-pyridinyl]urea N-[(1S,1aR,7bR)-4,7-difluoro-1,1a,2,7b-tetrahydrocyclopropa[c]chromen-1-yl]-N'-[5-(4-cyano-3-fluorophenoxy)-2-pyridinyl]urea was synthesized analogously to Example 3 from 4-[(6-amino-3-pyridinyl)oxy]-2-fluorobenzonitrile (58 mg, 0.24 mmol) to give 46 mg of pure product as white powder (46% yield).

$^1$H-NMR (CDCl$_3$): 9.77 (br s, ~1H), 9.45 (br s, ~1H), 7.70 (d, 1H), 7.58 (app tr, 1H), 7.32 (app dd, 1H), 6.93-6.99 (m, 1H), 6.75-6.85 (m, 2H), 6.70 (app d tr, 1H), 6.54-6.62 (m, 1H), 4.50 (dd, 1H), 4.31 (dd, 1H), 3.85 (br q, 1H), 2.63 (br tr, 1H), 1.96-2.03 (m, 1H). LC-MS: M$^+$453, M$^-$451.

EXAMPLE 34

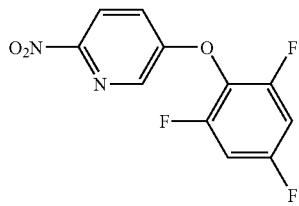

2-nitro-5-(2,4,6-triflurophenoxy)pyridine 2-nitro-5-(2,4,6-trifluorophenoxy)pyridine was synthesized analogously to Example 1 from 2,4,6-trifluorophenol (0.4 g, 2.7 mmol) to give 310 mg of product (47% yield).

$^1$H-NMR (CDCl$_3$): 8.36 (d, 1H), 8.28 (d, 1H), 7.42 (dd, 1H), 6.89 (app tr, 2H).

EXAMPLE 35

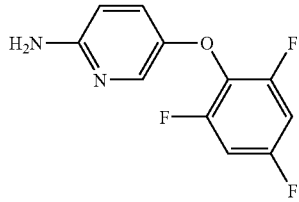

5-(2,4,6-triflurophenoxy)-2-pyridinylamine

4-[(6-amino-3-pyridinyl)oxy]-2-fluorobenzonitriie was synthesized analogously to Example 2 from 2-nitro-5-(2,4,6-trifluorphenoxy)pyridine (310 mg) to give 280 mg of product as brownish powder after purification by filtration through the short pad of silica.

$^1$H-NMR (CDCl$_3$): 7.83 (d, 1H), 7.15 (dd, 1H), 6.77 (app tr, 2H), 6.48 (d, 1H).

EXAMPLE 36

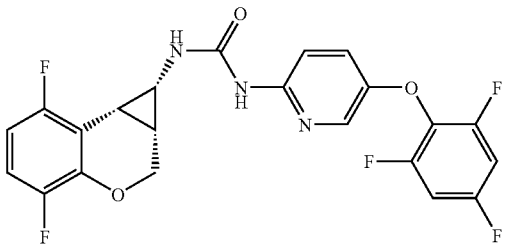

N-[(1S,1aR,7bR)-4,7-difluoro-1,1a,2,7b-tetrahydro-cyclopropa[c]chromen-1-yl]-N'-[5-(2,4,6-triflurophenoxy)-2-pyridinyl]urea N-[(1S,1aR,7bR)-4,7-difluoro-1,1a,2,7b-tetrahydrocyclopropa[c]chromen-1-yl]-N'-[5-(2,4,6-trifluorophenoxy)-2-pyridinyl]urea was synthesized analogously to Example 3 from 5-(2,4,6-trifluorophenoxy)-2-pyridinylamine (59 mg, 0.24 mmol) to give 25 mg of pure product as white powder (24% yield).

$^1$H-NMR (CDCl$_3$): 9.40 (br s, 1H), 9.10 (br s, 1H), 7.51 (d, 1H), 7.23 (dd, 1H), 6.72-6.87 (m, 3H), 6.55 (tr d, 1H). 4.44 (dd, 1H), 4.31 (dd, 1H), 3.83 (q, 1H), 2.58 (br tr, 1H), 1.91-1.98 (m, 1H). LC-MS: M$^+$464, M$^-$462.

EXAMPLE 37

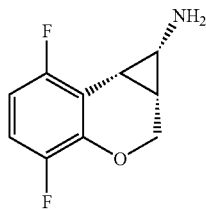

(1S,1aR,7bR)-4,7-difluoro-1,1a,2,7b-tetrahydrocyclopropa[c]chromen-1-amine (1S,1aR,7bS)-4,7-difluoro-1,1a,2,7b-tetrahydrocyclopropa[c]chromen-1-carboxylic acid (0.5 g, 2.2 mmol, ~95% ee) was mixed with toluene (3 ml), triethylamine (0.34 ml, 1.1 eq), DPPA (0.52 ml, 1.1 eq) and bubbled with argon for about 5 min. The reaction mixture was then heated at stirring at 120° C. for 1.5 h under argon. The temperature was then decreased to 50° C. and a mixture of 3 ml of 10% hydrochloric acid in 10 ml dioxane was added. The reaction mixture was stirred for 2 h at 50° C. and then concentrated by rotary evaporation. The residue was mixed with water ant diethyl ether. Water phase was collected and basified with 28% aqueous ammonia to pH 11 and extracted into ether (3×20 ml). Combined organic phases were washed with water and brine and dried over magnesium sulfate. Concentration by rotary evaporation gave 310 mg of crude product as yellow orange oil. The product was purified by column chromatography on silica (30 g, EtOAc/hexane 1:2) to give 220 mg of colorless oil (50% yield).

¹H-NMR (CDCl₃): 6.85 (ddd, 1H), 6.60 (tr d, 1H), 4.51 (dd, 1H), 4.33 (dd, 1H), 2.97 (tr, 1H), 2.28 (app tr, 1H), 1.71 (m, 1H), 1.23 (br s, 2H).

EXAMPLE 38

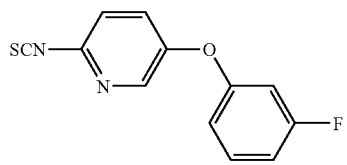

5-(3-fluorophenoxy)-2-isothiocyanatopyridine 5-(3-Fluorophenoxy)-2-pyridinamine (210 mg, 1 mmol) was dissolved in dry degassed methylene chloride (5 ml) and thiophosgene (0.11 ml, 1.3 mmol) was added through syringe during 5-10 min to the stirred solution. Pyridine (0.18 ml, 2 mmol) was added to the reaction mixture right after the addition of thiophosgene and the reaction mixture was stirred at ambient temperature for 1.5-2 h. Then the reaction mixture was poured into water (15 ml) and extracted into methylene chloride (3×20 ml). Organic extract was washed with water and brine and dried over magnesium sulfate. Solvent was then removed by rotary evaporation and the oil obtained was purified by column chromatography on silica (30 g, EtOAc/hexane 1:3) to give 190 mg of pure product as dark brown-purple solid. Yield 75%.

¹H-NMR (CDCl₃): 8.20 (d, 1H), 7.30-7.37 (m, 2H), 7.10 (d, 1H), 6.89 (dd tr, 1H), 6.80 (app dd, 1H), 6.74 (d tr, 1H).

EXAMPLE 39

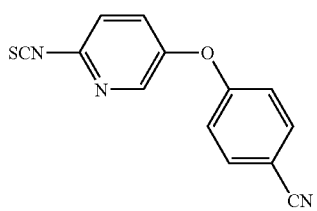

4-[(6-isothiocyanato-3-pyridinyl)oxy]benzonitrile

4-[(6-Isothiocyanato-3-pyridinyl)oxy]benzonitrile was synthesized analogously to Example 38 from 4-[(6-amino-3-pyridinyl)oxy]benzonitrile (275 mg, 1.3 mmol) to give 160 mg of pure product as brown-beige powder (49% yield).

¹H-NMR (CDCl₃): 8.25 (d, 1H), 7.67 (app d, 2H), 7.41 (dd, 1H), 7.15 (d, 1H), 7.06 (app d, 2H).

EXAMPLE 40

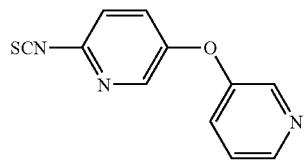

2-isothiocyanato-5-(3-pyridinyloxy)pyridine 2-isothiocyanato-5-(3-pyridinyloxy)pyridine was synthesized analogously to Example 38 from 5-(3-pyridinyloxy)-2-pyridinamine (200 mg, 1 mmol) to give 110 mg of pure product as orange-pink oil (45% yield).

¹H-NMR (CDCl₃): 8.43 (tr, 1H), 8.42 (tr, 1H), 8.22 (d, 1H), 7.31-7.36 (m, 3H), 7.11 (app d, 1H). LC-MS: M⁺198.

EXAMPLE 41

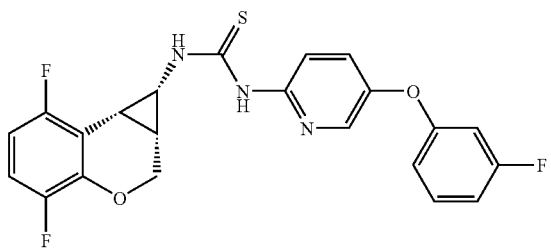

N-[(1S,1aR,7bR)-4,7-difluoro-1,1a,2,7b-tetrahydrocyclopropa[c]chromen-1-yl]-N'-[5-(3-fluorophenoxy)-2-pyridinyl]thiourea (1S,1aR,7bR)-4,7-difluoro-1,1a,2,7b-tetrahydrocyclopropa[c]chromen-1-amine (20 mg, 0.1 mmol) was dissolved in dry acetonitrile (1 ml) and 5-(3-fluorophenoxy)-2-isothiocyanatopyridine (25 mg, 0.1 mmol) was added and the reaction mixture was stirred at ambient temperature for 12 h. The precipitate formed was collected by filtration and washed with acetonitrile and diethyl ether to give 17 mg (38% yield) of pure product as beige powder.

¹H-NMR (CDCl₃): 8.21 (br s, 1H), 7.45 (br d, 1H), 7.28-7.34 (m, 2H), 6.87 (d tr, 1H), 6.79 (tr d, 1H), 6.72 (app dd, 1H), 6.56-6.69 (m, 3H), 4.46 (dd, 1H), 4.34 (dd, 1H), 4.17 (br q, 1H), 2.72 (br tr, 1H), 2.06-2.13 (m, 1H).

EXAMPLE 42

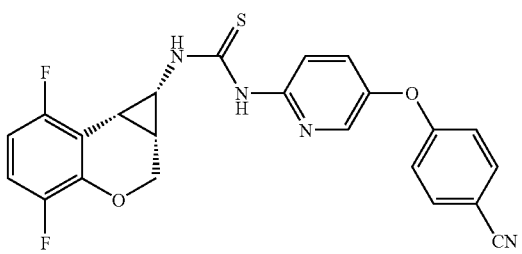

N-[(1S,1aR,7bR)-4,7-difluoro-1,1a,2,7b-tetrahydro-cyclopropa[c]chromen-1-yl]-N'-[5-(4-cyanophenoxy)-2-pyridinyl]thiourea N-[(1S,1aR,7bR)-4,7-difluoro-1,1a,2,7b-tetrahydrocyclopropa[c]chromen-1-yl]-N'-[5-(4-cyanophenoxy)-2-pyridinyl]thiourea was synthesized analogously to Example 41 from 4-[(6-isothiocyanato-3-pyridinyl)oxy]benzonitrile (52 mg, 0.2 mmol) to give 80 mg (88% yield) of pure product as beige-white powder.

$^1$H-NMR (CDCl$_3$): 11.50 (d, 1H), 9.78 (s, 1H), 7.65 (app d, 2H), 7.53 (d, 1H), 7.35 (dd, 1H), 7.00 (d, 1H), 6.98 (app d, 2H), 6.78 (d tr, 1H), 6.59 (d tr, 1H), 4.48 (dd, 1H), 4.33 (dd, 1H), 4.19 (br q, 1H), 2.74 (br tr, 1H), 2.08-2.16 (m, 1H). LC-MS: M$^-$449.

EXAMPLE 43

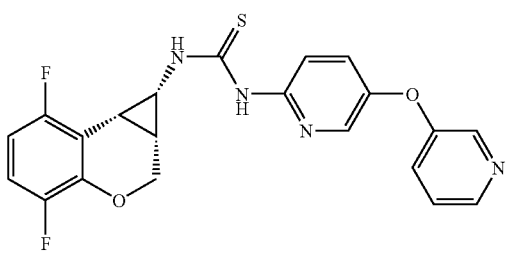

N-[(1S,1aR,7bR)-4,7-difluoro-1,1a,2,7b-tetrahydro-cyclopropa[c]chromen-1-yl]-N'-[5-(3-pyridinyloxy)-2-pyridinyl]thiourea N-[(1S,1aR,7bR)-4,7-difluoro-1,1a,2,7b-tetrahydrocyclopropa[c]chromen-1-yl]-N'-[5-(3-pyridinyloxy)-2-pyridinyl]thiourea was synthesized analogously to Example 41 from 2-isothiocyanato-5-(3-pyrdinyloxy)pyridine (58 mg, 0.25 mmol) to give 40 mg (37% yield) of pure product as beige powder.

$^1$H-NMR (CDCl$_3$): 11.48 (d, 1H), 9.47 (br s, 1H), 8.42 (dd, 1H), 8.39 (d, 1H), 7.45 (d, 1H), 7.32 (app dd, 2H), 7.24 (ddd, 1H), 6.90 (d, 1H), 6.78 (app d tr, 1H), 6.57 (d tr, 1H) 4.46 (dd, 1H), 4.33 (dd, 1H), 4.18 (br q, 1H), 2.72 (br tr, 1H), 2.28 (app ddd, 1H) LC-MS: M$^+$427, M$^-$425.

EXAMPLE 43

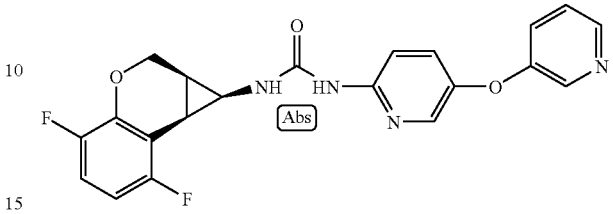

N-[(1S,1aR,7bS)-4,7-difluoro-1,1a,2,7b-tetrahydro-cyclopropa[c]chromen-1-yl]-N'-[5-(pyridinyloxy)-2-pyridinyl]urea (1S,1aR,7bS)-4,7-difluoro-1,1a,2,7b-tetrahydrocyclopropa[c]chromen-1-carboxylic acid (226 mg, 1.1 mmol), 5-(pyridine-3-yloxy)-pyridine-2-ylamine, DPPA 227 μL (97%) and triethylamine 140 μL were dissolved in Toluene (3 mL) and heated to reflux for 3 h. The solvent was removed and the crude product was dissolved in ethyl acetate and washed with HCl$_{aq}$ (0.01 M), water and brine. Purification by chromatography (silica gel, ether-2% methanol ether-5% methanol) gave pure product (80 mg, 20%)

$^1$H-NMR (CDCl$_3$-MeOD): 9.4 (Br S, 1H), 8.49 (broad s, 1H), 8.40-8.37 (m, 2H), 7.61 (d, 1H), 7.30-727 (m, 2H), 7.23-7.19 (m, 1H), 6.82-6.76 (m, 2H), 6.60-6.54 (m, 1H), 4,46 (dd, 1H), 4.33 (dd, 1H), 3.80 (q, 1H), 2.60 (t, 1H), 1.99-1.94 (m, 1H).

Additional Left Wings.

The following left wings are coupled to any of the above novel right hand wings analogously to Example 3 and/or 38 and/or 41 and/or with an activated 5-substituted-pyridin-pyridin-2-yl, such as the corresponding imidazole-1-carbothioic acid (5-substituted-pyridin-2-yl)amide as described in EP 540 143

EXAMPLE 44 a) ±cis-1,1a,2,7b-Tetrahydro-cyclopropa[c]chromene-1-carboxylic acid ethyl ester To a mixture of 2H-chromene (4.89 g, 37 mmol) and (CuOTf)$_2$-benzene (186 mg, 0.37

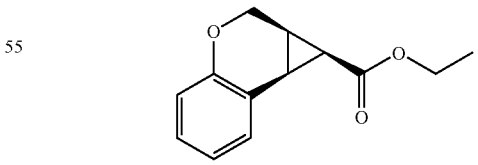

mmol) in 1,2-dichloroethane (80 mL) at 20° C., was added dropwise (3 h) a solution of ethyl diazoacetate (8.44 g, 74 mmol) in 1,2-dichloroethane (20 mL). After 15 min at 20° C., the reaction mixture was washed with H$_2$O (100 mL). The H$_2$O phase was washed with CH$_2$Cl$_2$ (50 mL) and the solvent of the combined organic phases was removed under reduced pressure. The crude product was column chromatographed (silica gel, 20→50% EtOAc in hexane), to give 1.96 g (24%) of ±cis-1,1a,2,7b-tetrahydro-cyclopropa[c]chromene-1-carboxylic acid ethyl ester and 3.87-g (48%) of ±-trans-1,1a,2,7b-tetrahydro-cyclopropa[c]chromene-1-carboxylic acid ethyl ester as a by product.

¹H-NMR (CDCl₃): 7.26 (d, 1H), 7.10 (dd, 1H), 6.90 (dd, 1H), 6.78 (d, 1H), 4.49 (dd, 1H), 4.20 (dd, 1H), 3.97 (q, 2H), 2.44 (dd, 1H), 2.14 (dd, 1H), 2.07-1.95 (m, 1H), 1.02 (t, 3H).

b) (±)-cis-1,1a,2,7b-Tetrahydro-cyclopropa[c]chromene-1-carboxylic acid

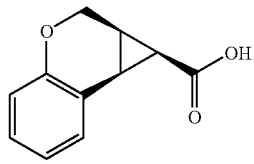

A mixture of (±)-cis-1,1a,2,7b-tetrahydro-cyclopropa[c]chromene-1-carboxylic acid ethyl ester (1.96 g, 9.0 mmol), LiOH (539 mg, 22.5 mmol), H₂O (10 mL) and MeOH (20 mL) was heated to reflux for 2 h. The reaction mixture was concentrated to about 10 mL, 4N HCl was added dropwise giving a white precipitate. The reaction mixture was extracted with CH₂Cl₂ (3×15 mL) and the solvent of the combined organic phases was removed under reduced pressure. The crude product was crystallized from EtOAc/hexane, to give 435 mg (25%) of (±)-cis-1,1a,2,7b-tetrahydro-cyclopropa[c]chromene-1-carboxylic acid as a white solid.

¹H-NMR (CDCl₃): 9.80 (br s, 1H), 7.22 (d, 1H), 7.10 (dd, 1H), 6.89 (dd, 1H), 6.77 (d, 1H), 4.45 (dd, 1H), 4.22 (dd, 1H), 2.45 (dd, 1H), 2.14-1.98 (m, 2H).

EXAMPLE 45 a) (±)-cis-1,1a,3,7b-Tetrahydro-2-oxa-cyclopropa[a]naphthalene-1-carboxylic acid ethyl ester

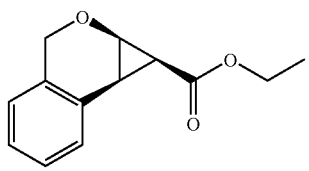

(±)-cis-1,1a,3,7b-Tetrahydro-2-oxa-cyclopropa[c]naphthalene-1-carboxylic acid ethyl ester was synthesized analogously to Example 44a from 1H-isochromene (3.57 g, 27 mmol), to give 910 mg (15%) of (±)-cis-1,1a,3,7b-tetrahydro-2-oxa-cyclopropa[a]naphthalene-1-carboxylic acid ethyl ester.

¹H-NMR (CDCl₃): 7.34 (d, 1H), 7.25 (dd, 1H), 7.18 (dd, 1H), 7.03 (d, 1H), 4.81 (d, 1H), 4.51 (d, 1H), 4.28 (dd, 1H), 3.95 (q, 2H), 2.43 (dd, 1H), 2.05 (dd, 1H), 1.04 (t, 3H).

b) (±)-cis-1,1a,3,7b-Tetrahydro-2-oxa-cylopropa[a]naphthalene-1-carboxylic acid

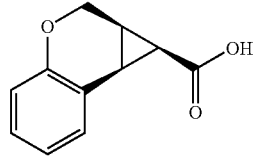

(±)-cis-1,1a,3,7b-Tetrahydro-2-oxa-cyclopropa[a]naphthalene-1-carboxylic acid was synthesized analogously to Example 44b from (±)-cis-1,1a,3,7b-tetrahydro-2-oxa-cyclopropa[a]naphthalene-1-carboxylic acid ethyl ester (436 mg, 2 mmol), to give 86 mg (22%) of (±)-cis-1,1a,3,7b-tetrahydro-2-oxa-cyclopropa[a]naphthalene-1-carboxylic acid as a white solid. The crude product was column chromatographed (silica gel, 1→5% MeOH in CH₂Cl₂).

¹H-NMR (CDCl₃): 8.50 (br s, 1H), 7.39 (d, 1H), 7.30 (dd, 1H), 7.21 (dd, 1H), 7.07 (d, 1H), 4.87 (d, 1H), 4.57 (d, 1H), 4.38 (dd, 1H), 2.59 (dd, 1H), 2.15 (dd, 1H).

The product of step b

EXAMPLE 46

(±)-cis-1-(5-Cyano-pyridin-2-yl)-3-(7-hydroxy-6-propionyl-1,1a,2,7b-tetrahydro-cyclopropa[c]chromen-1-yl)-urea a) 1-(2-Hydroxy-4-prop-2-ynyloxy-phenyl)-propan-1-one

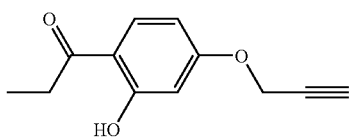

A mixture of 2',4'-dihydroxy-propiophenone (24.9 g, 0.15 mol), 3-bromo-propyne (24.2 g, 0.20 mol) and K₂CO₃ (20.7 g, 0.15 mol) in acetone (500 mL) was refluxed for 12 h. The reaction mixture was allowed assume room temperature and the precipitate was removed by filtration. The filtrate was concentrated under reduced pressure. The crude product was purified by column chromatography (silica gel, 0→2% MeOH in H₂O), to give 26.2 g (85%) of 1-(2-hydroxy-4-prop-2-ynyloxy-phenyl)-propan-1-one.

¹H-NMR (CDCl₃): 12.80 (s, 1H), 7.69 (d, 1H), 6.52 (m, 2H), 4.72 (d, 2H), 2.96 (q, 2H), 2.56 (t, 1H), 1.23 (t, 3H).

3b) 1-(5-Hydroxy-2H-chromen-6-yl)-propan-1-one

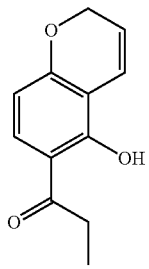

A mixture of 1-(2-hydroxy-4-prop-2-ynyloxy-phenyl)-propan-1-one (19.8 g, 97 mmol) and N,N-diethylaniline (100 mL) was heated to reflux for 3 h. The reaction mixture was concentrated under reduced pressure. The crude product was purified by column chromatography (silica gel, 5-10% EtOAc in Hexane) and thereafter recrystallized from EtOAc/Hexane, to give 8.91 g (45%) of 1-(5-hydroxy-2H-chromen-6-yl)-propan-1-one.

$^1$H-NMR (CDCl$_3$): 13.00 (s, 1H), 7.49 (d, 1H), 6.75 (dt, 1H), 6.27 (d, 1H), 5.67 (dt, 1H), 4.86 (dd, 2H), 2.90 (q, 2H), 1.19 (t, 3H).

3c) 7-Hydroxy-6-propionyl-1,1a,2,7b-tetrahydro-cyclopropa[c]chromene-1-carboxylic acid ethyl ester

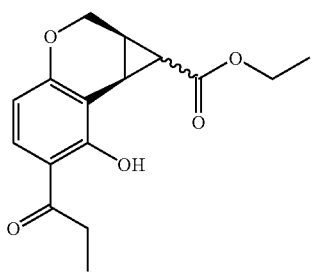

To a mixture of 1-(5-hydroxy-2H-chromen-6yl)-propan-1-one (511 mg, 2.5 mmol) and (Rh(II)Ac$_2$)$_2$ (11 mg, 0.025 mmol) in 1,2-dichloroethane (8 mL) at 20° C., was added dropwise (3 h) a solution of ethyl diazoacetate (571 mg, 5 mmol) in 1,2-dichloroethane (2 mL). After 15 min at 20° C., the reaction mixture was washed with H$_2$O (10 mL). The H$_2$O phase was washed with CH$_2$Cl$_2$ (10 mL) and the solvent of the combined organic phases was removed under reduced pressure. The crude product was purified by column chromatography (silica gel, 1→5% MeOH in CH$_2$Cl$_2$), to give 300 mg (41%) of 7-hydroxy-6-propionyl-1,1a,2,7b-tetrahydro-cyclopropa[c]chromene-1-carboxylic acid ethyl ester (a 33/64 mixture of cis and trans isomers).

$^1$H-NMR (CDCl$_3$): 13.13-13.07 (m, 1H), 7.57-7.49 (m, 1H), 6.41-6.38 (m, 1H), 4.65-3.92 (m, 4H), 3.01-1.95 (m, 5H), 1.29-1.08 (m, 6H).

3d) (±)-cis-7-Hydroxy-6-propionyl-1,1a,2,7b-tetrahydro-cyclopropa[c]chromene-1-carboxylic acid

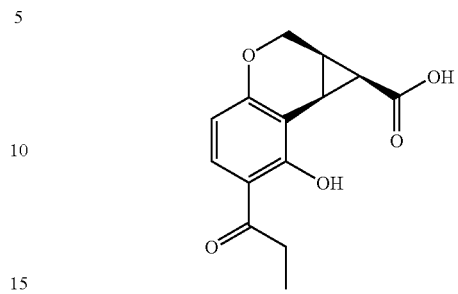

±cis-7-Hydroxy-6-propionyl-1,1a,2,7b-tetrahydro-cyclopropa[c]chromene-1-carboxylic acid was synthesized analogously to Example 2b from 7-hydroxy-6-propionyl-1,1a,2,7b-tetrahydro-cyclopropa[c]chromene-1-carboxylic acid ethyl ester (299 mg, 1.03 mmol, a 33/64 mixture of cis and trans isomers), to give 39.3 mg (15%) of (±)-cis-7-hydroxy-6-propionyl-1,1a,2,7b-tetrahydro-cyclopropa[c]chromene-1-carboxylic acid as a white solid and (±)-trans-7-hydroxy-6-propionyl-1,1a,2,7b-tetrahydro-cyclopropa[c]chromene-1-carboxylic acid as a byproduct. The crude product was purified by column chromatography (silica gel, 1→5% MeOH in CH$_2$Cl$_2$).

$^1$H-NMR (DMSO-d$_6$): 7.67 (d, 1H), 6.35 (d, 1H), 4.57 (dd, 1H), 4.36 (dd, 1H), 2.98 (q, 2H), 2.55-2.46 (m, 1H), 2.18-2.00 (m, 2H), 1.10 (t, 3H).

EXAMPLE 47 a) 1-(2-Hydroxy-4-prop-2-ynyloxy-phenyl)-ethanone

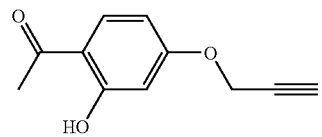

1-(2-Hydroxy-4-prop-2-ynyloxy-phenyl)-ethanone was synthesized analogously to Example 46a from 1-(2,4-dihydroxy-phenyl)-ethanone (20 g, 131 mmol), to give 22 g (88%) of 1-(2-hydroxy-4-prop-2-ynyloxy-phenyl)-ethanone.

$^1$H-NMR (CDCl$_3$): 12.70 (s, 1H), 7.66 (d, 1H), 6.52 (m, 2H), 4.72 (d, 2H), 2.58-2.55 (m, 4H).

b) 1-(5-Hydroxy-2H-chromen-6-yl)-ethanone

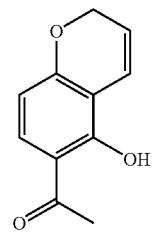

1-(5-Hydroxy-2H-chromen-6-yl)-ethanone was synthesized analogously to Example 46b from 1-(2-hydroxyprop-2-ynyloxy-phenyl)-ethanone (17 g, 89 mmol), to give 6.0 g (35%) of 1-(5-hydroxy-2H-chromen-6-yl)-ethanone.

$^1$H-NMR (CDCl$_3$): 12.92 (s, 1H), 7.51 (d, 1H), 6.79 (dt, 1H), 6.32 (d, 1H), 5.71 (dt, 1H) 4.89 (dd, 2H), 2.55 (s, 3H).

4c) 6-Acetyl-7-hydroxy-1,1a,2,7b-tetrahydro-cyclopropa[c]chromene-1-carboxylic acid ethyl ester

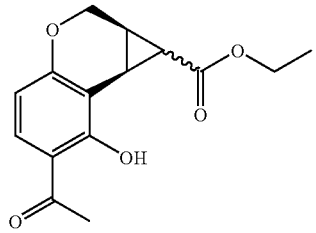

6-Acetyl-7-hydroxy-1,1a,2,7b-tetrahydro-cyclopropa[c]chromene-1-carboxylic acid ethyl ester (a 40/60 mixture of cis and trans isomers) was synthesized analogously to Example 46c from 1-(5-hydroxy-2H-chromen-6-yl)-ethanone.

$^1$H-NMR (CDCl$_3$): 13.05-12.97 (m, 1H), 7.54-7.47 (m, 1H), 6.43-6.33 (m, 1 H), 4.63-3.94 (m, 4H), 3.02-1.96 (m, 6H), 1.31-1.08 (m, 3H).

d) 6-Acetyl-7-hydroxy-1,1a,2,7b-tetrahydro-cyclopropa[c]chromene-1-carboxylic acid

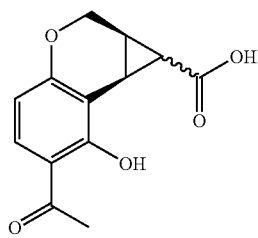

6-Acetyl-7-hydroxy-1,1a,2,7b-tetrahydro-cyclopropa[c]chromene-1-carboxylic acid was synthesized analogously to Example 44b from 6-acetyl-7-hydroxy-1,1a,2,7b-tetrahydro-cyclopropa[c]chromene-1-carboxylic acid ethyl ester (2 g, 8.1 mmol, a 40/60 mixture of cis and trans isomers), to give 300 mg (17%) of 6-acetyl-7-hydroxy-1,1a,2,7b-tetrahydro-cyclopropa[c]chromene-1-carboxylic acid (a 40/60 mixture of cis and trans isomers). The crude product was purified by column chromatography (silica gel, 1→5% MeOH in CH$_2$Cl$_2$)

$^1$H-NMR (CDCl$_3$): 7.55-7.45 (m, 1H), 6.45-6.30 (m, 1H), 4.65-4.00 (m, 2H), 3.05-1.95 (m, 6H).

EXAMPLE 48

5a) 1-(4-Fluoro-2-prop-2-ynyloxy-phenyl)-propan-1-one

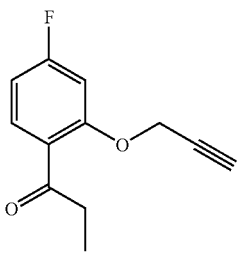

To a mixture of NaH (95%, 278 mg, 11 mmol) in DMF (20 mL) at 0° C., was added 1-(4-fluoro-2-hydroxy-phenyl)-propan-1-one (1.68 g, 10 mmol) in DMF (5 mL). After 15 min at 0° C., was 3-bromo-propyne (3.02 g, 20 mmol) added to the reaction mixture. After 1 h at 0° C., was the reaction mixture allowed to assume room temperature. The reaction mixture was extracted with H$_2$O (100 mL). The H$_2$O phase was washed with Et$_2$O 3×100 mL) and the solvent of the combined organic phases was removed under reduced pressure. The crude product was purified by column chromatography (silica gel, CH$_2$Cl$_2$), to give 1.40 g (68%) of 1-(4-fluoro-2-prop-2-ynyloxy-phenyl)-propan-1-one.

$^1$H-NMR (CDCl$_3$): 7.64 (dd, 1H), 6.69 (dd, 1H), 6.60 (ddd, 1H), 4.68 (d, 2H), 2.85 (q, 2H), 2.58 (t, 1H), 1.03 (t, 3H).

b) 1-(5-Fluoro-2H-chromen-8-ylpropan-1-one

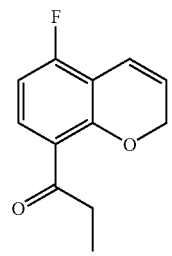

1-(5-Fluoro-2H-chromen-8-yl)-propan-1-one was synthesized analagously to Example 46b from 1-(4-fluoro-2-prop-2-ynyloxy-phenyl)-propan-1-one (1.34 g, 6.5 mmol), to give 619 mg (46%) of 1-(5-fluoro-2H-chromen-8-yl)-propan-1-one.

$^1$H-NMR (CDCl$_3$): 7.60 (dd, 1H), 6.67-6.58 (m, 2H), 5.86 (dt, 1H), 4.76 (dd, 2H), 2.93 (q, 2H), 1.23 (t, 3H).

c) (±)-cis-7-Fluoro-4-propionyl-1,1a,2,7b-tetrahydro-cyclopropa[c]chromene-1-carboxylic acid ethyl ester

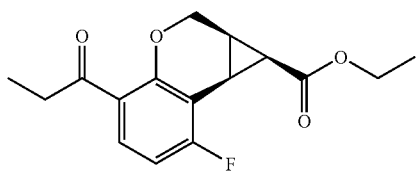

(±)-cis-7-Fluoro-4-propionyl-1,1a,2,7b-tetrahydro-cyclopropa[c]chromene-1-carboxylic acid ethyl ester was synthesized according to method 46c) from 1-(5-fluoro-2H-chromen-8-yl)-propan-1-one (619 mg, 3 mmol), to give 142 mg (16%) of (±)-cis-7-fluoro-4-propionyl-1,1a,2,7b-tetrahydro-cyclopropa[c]chromene-1-carboxylic acid ethyl ester and (±)-trans-7-fluoro-4-propionyl-1,1a,2,7b-tetrahydro-cyclopropa[c]chromene-1-carboxylic acid ethyl ester as a byproduct.

¹H-NMR (CDCl₃): 7.59 (dd, 1H), 6.65 (m, 1H), 4.50-4.46 (m, 2H), 3.95 (q, 2H), 2.89 (q, 2H), 2.57 (dd, 1H), 2.20 (dd, 1H), 1.13-1.03 (m, 1H), 1.12-1.01 (m, 6H).

5d) (±)-cis-7-Fluoro-4-propionyl-1,1a,2,7b-tetrahydro-cyclopropa[c]chromene-1-carboxylic acid

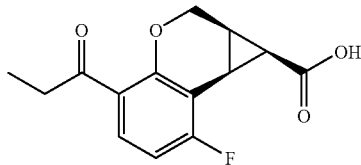

(±)-cis-7-Fluoro-4-propionyl-1,1a,2,7b-tetrahydro-cyclopropa[c]chromene-1-carboxylic acid was synthesized analogously to Example 44b from (±)-cis-7-fluoro-4-propionyl-1,1a,2,7b-tetrahydro-cyclopropa[c]chromene-1-carboxylic acid ethyl ester (140.3 mg, 0.48 mmol). to give 83 mg (65%) of (±)-cis-7-fluoro-4-propionyl-1,1a,2,7b-tetrahydro-cyclopropa[c]chromene-1-carboxylic acid as a white solid. The crude product was purified by column chromatography (silica gel, 1→5% MeOH in CH₂Cl₂).

¹H-NMR (DMSO-d₆): 12.15 (br s, 1H), 7.46 (dd, 1H), 6.78 (dd, 1H), 4.57 (dd, 1H), 4.43 (dd, 1H), 2.93-2.80 (m, 2H), 2.55 (dd, 1H), 2.24 (dd, 1H), 2.20-2.10 (m, 1H), 1.02 (t, 3H).

EXAMPLE 49 a) 6-Fluoro-2-hydroxy-3-methoxy-benzaldehyde 1M boron trichloride in dichloromethane (25 ml; 25 mmol) was added to a solution of 6-fluoro-2,3-dimethoxy-benzaldehyde [Cantrell, Amanda S.; Engelhardt, Per; Hoegberg, Marita; Jaskunas, S. Richard; Johansson, Nils Gunnar; et al.; J. Med. Chem.; 39; 21; 1996; 4261-4274] (4.26 g; 23 mmol) in dichloromethane (30 ml) keeping the reaction temperature at −70 C. The reaction mixture stirred at room temperature overnight and hydrolyzed with water. The organic phase was separated, washed with water and evaporated in vacuc. The residue was chromatographed (silica gel, EA:Hex, 5:1) to give 3.72 g (94%) of 6-fluoro-2-hydroxy-3-methoxy-benzaldehyde as yellow crystals.

¹H-NMR (CDCl₃): 11.61 (s, 1H), 10.23 (s, 1H), 7.02 (dd, 1H), 6.55 (app. t, 1H), 3.87 (s, 3H).

b) 5-Fluoro-8-methoxy-2H-chromene

6-Fluoro-2-hydroxy-3-methoxy-benzaldehyde (3.32 g, 19 mmol) was dissolved in acetonitrile (20 ml) and DBU (2.97 ml, 19 mmol) was-added followed by vinyltriphenylphosphine bromide (7.2 g, 19 mmol). The reaction mixture was heated under reflux for 48 h, diluted with water and extracted with ether (3×50 ml). The organic phase was washed with water, 10% sodium hydroxide, water and brine and evaporated in vacuo. The residue was submitted to column chromatography (silica gel, EA:Hex, 1:20) yielding 1.2 g of 5-fluoro-8-methoxy-2H-chromene (34%).

¹H-NNMR (CDCl₃): 6.65 (m, 2H), 6.54 (t, 1H), 5.83 (dt, 1H), 4.88 (dd, 2H), 3.83 (s, 3H).

c) (±)-cis-7-Fluoro-4-methoxy-1,1a,2,7b-tetrahydro-cyclopropa[c]chromene-1-carboxylic acid ethyl ester The title compound was synthesized analogously to example 46c from 5-fluoro-8-methoxy-2H-chromene.

¹H-NMR (CDCl₃): 6.7-6.5 (m, 2H), 4.48 (m, 2H), 3.99 (m, 2H), 3.80 (s, 3H), 2.57 (app. t, 1H), 2.20 (app. t, 1H), 2.05 (m, 1H), 1.08 (t, 3H).

d) (±)-cis-7-Fluoro-4-methoxy-1,1a,2,7b-tetrahydro-cyclopropa[c]chromene-1-carboxylic acid The title compound was synthesized analogously to example 44b from (±)-cis-7-fluoro-4-methoxy-1,1a,2,7b-tetrahydro-cyclopropa[c]chromene-1-carboxylic acid ethyl ester.

¹H-NMR (CDCl₃): 6.7-6.5 (m, 2H), 4.48 (m, 2H), 3.80 (s, 3H), 2.61 (app. t, 1H), 2.17 (app. t, 1H), 2.06 (m, 1H).

e) (±)-cis-1-(5-Cyano-pyridin-2-yl)-3-(7-fluoro-4-methoxy-1,1a,2,7b-tetrahydro-cyclopropa[c]chromen-1-yl)-urea The title compound was synthesized analogously to Example 44c from (±)-cis-7-fluoro-4-methoxy-1,1a,2,7b-tetrahydro-cyclopropa[c]chromene-1-carboxylic acid (62 mg, 0.17 mmol). Yield 38 mg (40%).

¹H-NMR (CDCl₃): 10.06 (br. s, 1H), 9.40 (br. d, 1H), 8.11 (d, 1H), 7.70 (dd, 1H), 6.91 (d, 1H), 6.68 (m, 2H), 4.48 (dd, 1H), 4.28 (dd, 1H), 3.90-3.72 (m, 4H), 2.64 (app. T. 1H), 1.96 (m, 1H).

EXAMPLE 50 a) 1-Chloro-4-fluoro-2-prop-2-ynyloxy-benzene

The title compound was synthesized analogously to example 15a) from 2-chloro-5-flurophenol (2.5 g). Yield 2.8 g (90%).

¹H-NMR (CDCl₃): 7.32 (dd, 1H), 6.85 (dd, 1H), 6.68 (m, 1H), 4.77 (d, 2H), 2.58 (t, 1H).

7b) 5-Fluoro-8-chloro-2H-chromene

The title compound was synthesized analogously to Example 15b) from 1-chloro-4-fluoro-2-prop-2-ynyloxy-benzene (2.8 g). Yield 0.97 g (35%).

¹H-NMR (CDCl₃): 7.09 (dd, 1H), 6.63 (dt, 1H), 6.56 (t, 1H), 5.84 (dt, 1H), 4.95 (dd, 2H).

c) ±cis-7-Fluoro-4-chloro-1,1a,2,7b-tetrahydro-cyclopropa[c]chromene-1-carboxylic acid ethyl ester The title compound was synthesized analogously to Example 15c) from 5-Fluoro-8-chloro-2H-chromene.

¹H-NMR (CDCl₃): 7.14 (dd, 1H), 6.60 (t, 1H), 4.51 (m, 2H), 4.01 (m, 2H), 2.60 (app. t, 1H), 2.23 (t, 1H), 2.09 (m, 1H), 1.08 (t, 3H).

d) (±)-cis-7-Fluoro-4-chloro-1,1a,2,7b-tetrahydro-cyclopropa[c]chromene-1-carboxylic acid The title compound was synthesized analogously to example 15 d) from (±)-cis-7-fluoro-4-chloro-1,1a,2,7b-tetrahydro-cyclopropa[c]chromene-1-carboxylic acid ethyl ester 850 mg). Yield 43 mg (96%).

$^1$H-NMR (CDCl$_3$): 8.86 (br. s, 1H), 7.13 (dd, 1H), 6.59 (t, 1H), 4.50 (m, 2H), 2.63 (t, 1H), 2.23-2.05 (m, 2H).

EXAMPLE 51 a) Trifluoro-methanesulfonic acid 4-formyl-3-hydroxy-phenyl ester

A solution of triflic anhydride (1.77 ml, 10.5 mmol) in dichloromethane 10 ml) was added to a mixture of 2,4-dihydroxybenzaldehyde (1.38 g, 10 mmol) and pyridine (0.85 ml, 10.5 mmol) in dichloromethane (30 ml) at −70 C. Dry ice bath was removed and the reaction mixture was stirred for 2 h at room temperature. The reaction mixture was diluted with dichloromethane, washed with water, brine and evaporated in vacuo. The crude product was purified by column chromatography (silica gel, EA:Hex, 1:6) to give 1.55 g of trifluoro-methanesulfonic acid 4-formyl-3-hydroxy-phenyl ester (57%).

$^1$H-NMR (CDCl$_3$): 11.28 (s, 1H), 9.93 (s, 1H), 7.67 (d, 1H), 6.95 (m, 2H).

b) Trifluoro-methanesulfonic acid 3-allyloxy-4-formyl-phenyl ester

Potassium carbonate (1.6 g, 11.5 mmol) and allyl bromide (1 ml, 11.5 mmol) were added to a solution of trifluoro-methanesulfonic acid 4-formyl-3-hydroxy-phenyl ester (1.55 g, 5.7 mmol) in acetone (50 ml). The reaction mixture was stirred at 55 C for 2 h, filtered and evaporated in vacuo. The residue was chromatographed (silica gel, EA:Hex, 1:20) to give 1.3 g (73%) of trifluoro-methanesulfonic acid 3-allyloxy-4-formyl-phenyl ester.

$^1$H-NMR (CDCl$_3$): 10.47 (s, 1H), 7.93 (d, 1H), 6.95 (d, 1H), 6.90 (s, 1H), 6.05 (m, 1H), 5.47 (d, 1H), 5.40 (d, 1H), 4.69 (d, 2H).

c) Trifluoro-methanesulfonic acid 3-allyloxy-4-vinyl-phenyl ester

Methyltriphenylphosphonium bromide (1.95 g, 5.45 mmol) was added to a suspension of sodium hydride (60% in oil) (0.25 g, 6.3 mmol) in THF (35 ml) at 0 C and it was stirred for 30 min at room temperature. To the above solution was added solution of trifluoro-methanesulfonic acid 3-allyloxy-4-formyl-phenyl ester (1.3 g, 4.2 mmol) in THF (15 ml), nd the reaction mixture was stirred for 2 h at room temperature. The reaction mixture as diluted with hexane and extracted with water. Organic phase was washed with brine and evaporated. Silica gel column chromiatography (EA:Hex, 1:20) afforded trifluoromethanesulfonic acid 3-allyloxy-4-vinyl-phenyl ester (0.68 g, 53%).

$^1$H-NMR (CDCl$_3$): 7.51 (d, 1H), 7.02 (dd, 1H), 6.85 (dd, 1H), 6.77 (d, 1H), 6.05 (m, 1H), 5.76 (dd, 1H), 5.43 (m, 1H), 5.32 (m, 2H), 4.58 (dt, 2H).

d) Trifluoro-methanesulfonic acid 2H-chromen-7-yl ester

To a solution of trifluoro-methanesulfonic acid 3-allyloxy-4-vinyl-phenyl ester (0.68 g, 2.2 mmol) in dichloromethane (5 ml) was added Ru-catalyst (Grubb's catalyst) (36 mg, 2 mol %), and the reaction mixture was stirred for 2 h at room temperature. After that period the reaction was complete (GC) and the reaction mixture was used in the next step without any work-up. Analytical sample was obtained after removal of the solvent by silica gel column chromatography (EA:Hex, 1:20).

$^1$H-NMR (CDCl$_3$): 6.97 (d 1H), 6.76 (dd, 1H), 6.68 (d, 1H), 6.39 (dt, 1H), 5.81 (dt, 1H), 4.98 (dd, 2H).

e) (±)-cis-5-Trifluoromethanesulfonyloxy-1,1a,2,7b-tetrahydro-cyclopropa[c]chromene-1-carboxylic acid ethyl ester Rh(OAc)$_2$ (19 mg, 2 mol %) was added to the above solution (10d) and the solution of EDA (0.44 ml, 4.4 mmol) in 1 ml of dichloromethane was added with a syringe pump over 5 h at room temperature. When the reaction was complete (GC) dichloromethane was evaporated, the residue was dissolved in ethyl acetate and washed with saturated ammonium chloride solution and brine. Organic phase was evaporated and crude mixture of cis and trans-isomers (1:1.3) was separated by column chromatography (silica gel, EA:Hex, 1:6) to give 0.4 g (50%) of ±cis-5-trifluoromethanesulfonyloxy-1,1a,2,7b-tetrahydro-cyclopropa[c]chromene-1-carboxylic acid ethyl ester.

$^1$H-NMR (CDCl$_3$): 7.29 (d, 1H), 6.82 (dd, 1H), 6.73 (d, 1H), 4.51 (dd, 1H), 4.29 (dd, 1H), 3.98 (m, 2H), 2.45 (t, 1H), 2.19 (t, 1H), 2.05 (m, 1H), 1.03 (t, 3H).

f) ±cis-5-Cyano-1,1a,2,7b-tetrahydro-cyclopropa[c]chromene1-carboxylic acid ethyl ester ±cis-5-Trifluoromethanesulfonyloxy-1,1a,2,7b-tetrahydro-cyclopropa[c]chromene-1-carboxylic acid ethyl ester (154 mg, 0.42 mmol), Pd(OAc)$_2$ (9 mg, 10 mol %) and PPh$_3$ (44 mg, 40 mol %) were mixed in DMF (4 ml) and gentle stream of nitrogen passed through reaction mixture for 10 min. Zn(CN)$_2$ (74 mg, 0.63 mmol) was added, vial was sealed and the reaction mixture was stirred at 120 C overnight. The reaction mixture was diluted with ethyl acetate and extracted with saturated ammonium chloride. Organic phase was evaporated and residue chromatographed (silica gel, EA:Hex 1:5) to give 53 mg (52%) of ±cis-5-cyano-1,1a,2,7b-tetrahydro-cyclopropa[c]chromene-1-carboxyiic acid ethyl ester.

$^1$H-NMR (CDCl$_3$): 7.33 (d, 1H), 7.19 (dd, 1H), 7.05 (d, 1H), 4.50 (dd, 1H), 4.25 (dd, 1H), 3.99 (q, 2H), 2.46 (t, 1H), 2.25 (t, 1H), 2.11 (m, 1H), 1.06 (t, 3H).

g) ±cis-5-Cyano-1,1a,2,7b-tetrahydro-cyclopropa[c]chromene-1-carboxylic acid

±cis-5-Cyano-1,1a,2,7b-tetrahydro-cyclopropa[c]chromene-1-carboxylic acid ethyl ester (53 mg, 0.22 mmol) and NaOH (35 mg, 0.88 mmol) were dissolved in mixture methanol water (1:1) (5 ml). Reaction mixture was stirred at 60 C for 30 min. Methanol was evaporated in vacuo and 20 ml of water was added. Resulting solution was extracted with ether. Water phase was concentrated, acidified with 1M HCl to pH~12 and extracted with ether. The organic phase was washed with brine and evaporated to give 42 mg (90%) of ±cis-5-cyano-1,1a,2,7b-tetrahydro-cyclopropa[c]chromene-1-carboxylic acid.

$^1$H-NMR (CDCl$_3$): 7.33 (d, 1H), 7.19 (dd, 1H), 7.06 (d, 1H), 4.51 (dd, 1H), 4.31 (dd, 1H), 2.53 (app. t, 1H), 2.27 (app. t, 1H), 2.16 (m, 1H).

EXAMPLE 52 a) ±cis-5-Trimethylsilanylethynyl-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (152 mg, 0.41 mmol), DPPP (38 mg, 20 mol %), Pd(dba)$_2$ (24 mg, 10 mol %), CuI (3 mg, 4 mol %) were mixed in 3 ml of triethylariine and gentle stream of nitrogen passed through reaction mixture for 10 min. Trimethylsilyl-acetylene (0.088 ml, 0.62 mmol) was added, vial was sealed and the reaction mixture was stirred at 120 C overnight. The reaction mixture was diluted with ethyl acetate, washed with water, brine and evaporated. The residue was purified by silica gel column chromatography (EA:Hex, 1:15) to give 0.1 g (77%) of ±cis-5trimethylsilanylethynyl-1,1a,2,7b-tetrahydro-cyclopropa[c]chromene-1-carboxylic acid ethyl ester.

$^1$H-NMR (CDCl$_3$): 7.15 (d, 1H), 7.01 (dd, 1H), 6.88 (d, 1H), 4.47 (dd, 1H), 4.16 (dd, 1H), 3.96 (q, 2H), 2.38 (t, 1H), 2.13 (t, 1H), 2.01 (m, 1H), 1.04 (t, 3H), 0.22 (s, 9H).

b) ±cis-5-Ethynyl-1,1a,2,7b-tetrahydro-cyclopropa[c]chromene-1-carboxylic acid ±cis-5-Trimethylsilanylethynyl-1,1a,2,7b-tetrahydro-cyclopropa[c]chromene-1-carboxylic acid ethyl ester (0.1 g, 0.32 mmol) and sodium hydroxide (0.076 g, 1.9 mmol) were dissolved in mixture of methanol:water (1:1) (5 ml). The reaction mixture was heated at 60 C for 5 h, then it was acidified with 1 M HCl to pH~2 and extracted with ether. The organic phase was washed with brine and evaporated to give 66 mg (97%) of ±cis-5-ethynyl-1,1a,2,7b-tetrahydro-cyclopropa[c]chromene-1-carboxylic acid.

$^1$H-NMR (CDCl$_3$): 7.17 (d, 1H), 7.03 (dd, 1H), 6.91 (d, 1H), 4.45 (dd, 1H), 4.23 (dd, 1H), 3.02 (s, 1H), 2.46 (t, 1H), 2.13 (t, 1H), 2.07 (m, 1H).

EXAMPLE 53

±cis-1-(5-Acetyl-1,1a,2,7b-tetrahydro-cyclopropa[c]chromen-1-yl)-3-(5-cyano-pyridin-2-yl)-urea a) ±cis-5-Acetyl-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (117 mg, 0.32 mmol), DPPP (7.3 mg, 50 mol %), Pd(OAc)$_2$ (2 mg, 25 mol %) and triethyl amine (0.09 ml, 0.64 mmol) were mixed in DMF (3 ml) and gentle stream of nitrogen passed through reaction mixture for 10 min. Butyl vinyl ether (0.21 ml, 1.6 mmol) was added, vial was sealed and the reaction mixture was stirred at 100 C for 2 h. 5% HCl (5 ml) was added and the reaction mixture was stirred at room temperature for 30 min. Resulting mixture was extracted with ethyl acetate. The organic phase was washed with saturated ammonium chloride and evaporated. The residue was purified by silica gel column chromatography (EA:Hex, 1:5) to give 76 mg (91%) of ±cis-5-acetyl-1,1a,2,7b-tetrahydro-cyclopropa[c]chromene-1-carboxylic acid ethyl ester.

$^1$H-NMR (CDCl$_3$):7.52 (dd, 1H), 7.36 (d, 1H), 7.34 (d, 1H), 4.51 (dd, 1H), 4.21 (dd, 1H), 3.98 (q, 2H), 2.53 (s, 3H), 2.47 (t, 1H), 2.23 (t, 1H), 208 (m, 1H), 1.05(t, 3H).

b) ±cis-5-Acetyl-1,1a,2,7b-tetrahydro-cyclopropa[c]chromene-1-carboxylic acid The title compound was synthesized analogously to example 51 g from ±cis-5-acetyl-1,1a,2,7b-tetrahydro-cyclopropa[c]chromene-1-carboxylic acid ethyl ester (76 mg, 29 mmol). Yield 66 mg (97%).

$^1$H-NMR (CDCl$_3$): 7.52 (dd, 1H), 7.37 (d, 1H), 7.34 (d, 1H), 4.52 (dd, 1H), 4.26 (dd, 1H), 2.55 (s, 3H ), 2.53 (t, 1H), 2.25 (t, 1H), 2.13 (m, 1H).

EXAMPLE 54

±cis-5-Methoxy-1,1a,2,7b-tetrahydro-cyclopropa[c]chromene-1-carboxylic acid

The title compound was synthesized analogously to example 51 from 2-hydroxy-4-methoxybenzaldehyde.

EXAMPLE 55 a) N-Acetyl-1,2-dihydroquinoline

Quinoline (19.37 g, 150 mmol) was dissolved in anhydrous diethyl ether (500 ml) and cooled to 0° C. under inert atmosphere. DIBAL, 1.5 M in toluene (100 ml, 150 mmol) was added dropwise over 2 hrs and the reaction mixture was stirred at 0° C. for 30 min. Acetic anhydride (500 ml) was added dropwise over 30 min and the reaction mixture was stirred at 0° C. for 30 min. H$_2$O was added cautiously. The reaction mixture was extracted with diethyl ether and concentrated to give N-acetyl-1,2-dihydroquinoline (11.5 g, 44%).

b) ±cis-(N-acetyl-1,1a,2,7b-tetrahydro-cyclopropa[c]quinoline)-1-carboxylic acid ethyl ester ±cis-(N-acetyl-1,1a,2,7b-tetrahydro-cyclopropa[c]quinoline)-1-carboxylic acid ethyl ester was prepared according to the procedure described in example 44a, from N-acetyl-1,2-dihydroquinoline (10 g, 58 mmol) The product was purified by column chromatography on silica (EtOAc/hexane 5%→50%) to give ±cis-(N-acetyl-1,1a,2,7b-tetrahydro-cyclopropa[c]quinoline)-1-carboxylic acid ethyl ester (2.0 g, 13%).

c) ±cis-(N-Acetyl-1,1a,2,7b-tetrahydro-cyclopropa[c]quinoline)-1-carboxylic acid ±cis-(N-Acetyl-1,1a,2,7b-tetrahydro-cyclopropa[c]quinoline)-1-carboxylic acid (425 mg, 24%) was prepared according to the procedure described in example 44b, from ±cis-(N-acetyl-1,1a,2,7b-tetrahydro-cyclopropa[c]quinoline)-1-carboxylic acid ethyl ester (2.0 mg, 7.7 mmol).

EXAMPLE 56 a) 2,4-Difluoro-2-propynyloxybenzene

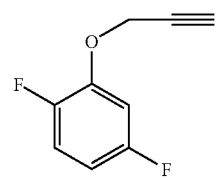

Commercially available 2,5-difluorophenol (20 g, 0.15 mol), K$_2$CO$_3$ (53 g, 0.38 mol) and commercially available 3-bromopropyne (45 g, 0.38 mol) were dissolved in acetone (300 ml), refluxed over night, cooled and filtrated. The solvent was removed and the crude product, dissolved in ether and washed with water and brine. The organic phase was evaporated and the crude product was re-dissolved in a small amount of ether and filtrated through a column of basic Al$_2$O$_3$. Evaporation and drying gave 20 g (80%) of 2,4-difluoro-2-prop-ynyloxy-benzene b) 5,8-Difluoro-2H-chromene

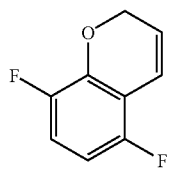

2,4-Difluoro-2-propynyloxybenzene (20 g, 0.12 mol) was dissolved in N,N,-diethyl aniline (100 ml) and heated under argon atmosphere at 225 deg. Celcius with an oil-bath for 6-8 h. Ether (150 ml) was added and the aniline was removed by extraction using 2 M HCl$_{(aq)}$. Purification by chromatography (silica gel, n-hexane) gave 5,8-difluoro-2H-chromene.5.8 g (29%)

c) +/−cis-4,7-Difluoro-1,1a,2,7b-tetrahydro-cyclopropa[c]chromene-1-carboxylic acid ethyl ester

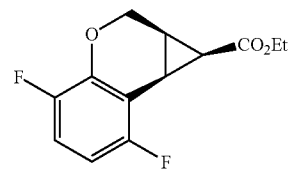

5,8-Difluoro-2H-chromene (5 g, 0.03 mol), (Rh(II)Ac$_2$)$_2$ (0.39 g, 0.00089 mol) was dissolved in 1,2-dichloroethane (60 ml) or ethanol-free chloroform. Ethyl diazoacetate (9.4 ml, 0089 mol) in the same solvent was added dropwise over a period of approximately 5 h under N$_2$ atmosphere. The solvent was then removed under vacuum and the mixture was taken upp in ethyl acetate, washed with NaHCO$_3$(aq), water and brine and the solvent removed. The product (33% cis, 66% trans) was purified by hromatography (0→10% ethyl acetate in n-hexane) to give 2.2 g of the title compound (30%).

d) cis-4,7-Difluoro-1,1a,2,7b-tetrahydro-cyclopropa[c]chromene-1-carboxylic acid

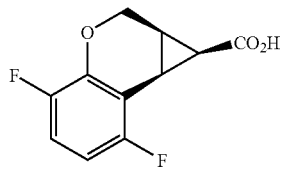

Cis-4,7-Difluoro-1,1a,2,7b-tetrahydro-cyclopropa[c]chromene-1-carboxylic acid ethyl ester (2 g, 0.008 mol) was heated in 1M LiOH in methanol-water (25%) at 80 deg. for 2 h. The volume was reduced to half and acidified. Extraction with ether followed by chromatography (silica gel, ether) gave pure title compound (35%)

EXAMPLE 57

Additional Intermediates a) 6-Fluorochroman-4-ol

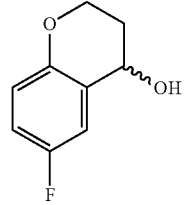

6-Fluorochroman-4-one (10 g, 61 mmol) was dissolved in ethanol (100 ml). NaBH$_4$ (excess) was added and cooled on icebath. The mixture was then left in room temperature for 2 h, followed by reflux for 4 h. Purification by chromatography (silica gel, ether-hexane, 1:5) gave 8. g (80%) pure 6-fluorochroman-4-ol.

b) 6-Fluoro-2H-chromene

6-Fluorochroman-4-ol (8 g, 48 mmol) and toluene-4-sulphonic acid (1 g) were dissolved in toluene and refluxed over-night with subsequent water removal. The mixture was then cooled and washed with NaHCO$_3$ (aq) and purified by chromatography (silica gel, n-hexane) to give 4.2 g (52%) of pure 6-fluoro-2H-chromene.

c) +/−cis-6-Fluoro-1,1a,2,7b-tetrahydro-cyclopropa[c]chromene-1-carboxylic acid ethyl ester

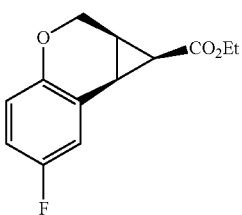

This Compound was prepared analogously to cis-4,7-Difluoro-1,1a,2,7b-tetrahydro-cyclopropa[c]chromene-1-carboxylic acid ethyl ester but using 6-fluoro-2H-chromene to give 1.9 (29%) of the tide compound.

d) Cis-6-Fluoro-1,1a,2,7b-tetrahydro-cyclopropa[c]chromene-1-carboxylic acid

This compound was prepared analogously to cis-4,7-difluoro-1,1a,2,7b-tetrahydro-cyclopropa[c]

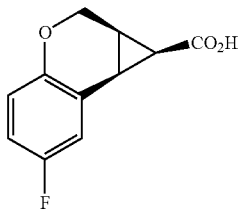

chromene-1-carboxylic acid but using cis-6-fluoro-1,1a,2,7b-tetrahydro-cyclopropa[c]chromene-1-carboxylic acid ethyl ester (1.9 g, 8 mmol) to give 350 mg (21%) of pure cis-6-fluoro-1,1a,2,7b-tetrahydro-cyclopropa[c]chromene-1-carboxylic acid e) 1-Bromo-4-fluoro-2-prop-2-ynyloxy-benzene

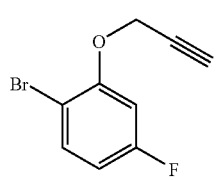

This compound was prepared analogously to 2,4-difluoro-2-prop-ynyloxy-benzene but using 2-bromo-5-fluorphenol (15 g, 78 mmol) to give 1-bromo-4-fluoro-2-prop-2-ynyloxy-benzene 15.6 g (87%)

f) 2-Bromo-4-fluoro-1-prop-2-ynyloxy-benzene

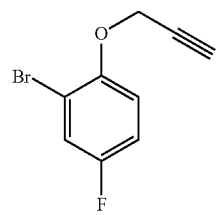

This compound was prepared analogously to 2,4-difluoro-2-prop-ynyloxy-benzene but using 2-bromo-4-fluoro-phenol (15 g, 78 mmol) to give 2-bromo-4-fluoro-1-prop-2-ynyloxy-benzene 15. g (84%).

g) 1,3-difluoro-5-prop-2-ynyloxy-benzene

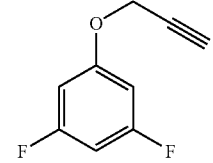

This compound was prepared analogously to 2,4-difluoro-2-propynyloxybenzene but using 3,5-difluoro-phenol (14 g, 107 mmol) to give 1,3-difluoro-5-prop-2-ynyloxy-benzene 12 g (67%).

h) 8-Bromo-6-fluoro-2H-chromene

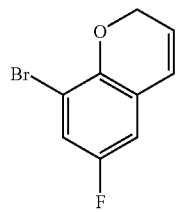

This compound was prepared analogously to 5,8-difluoro-2H-chromene but using (15 g, 65 mmol) of 2-bromo-4-fluoro-1-prop-2-ynyloxybenzene to give the title compound (7 g, 46%)

i) 8-Bromo-5-fluoro-2H-chromene

This compound was prepared analogously to 5,8-difluoro-2H-chromene but using (15 g, 65 mmol) of 1-bromo-4-fluoro-2-prop-2-ynyloxybenzene to give the title compound (3.7 g, 25%)

j) 5,7-Difluoro-2H-chromene

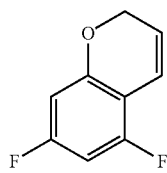

This compound was prepared analogously to 5,8-difluoro-2H-chromene but using (18 g, 107 mmol) of 1,3-difluoro-5-prop-2-ynyloxybenzene and PEG-200 as solvent to give the title compound (4 g, 23%).

k) +/−cis-4-Bromo-6-fluoro-1,1a,2,7b-tetrahydro-cyclopropa[c]chromene-1-carboxylic acid ethyl ester

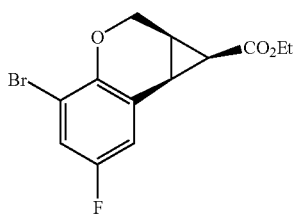

This compound was prepared analogously to +/−cis-4,7-difluoro-1,1a,2,7b-tetrahydro-cyclopropa[c]chromene-1-carboxylic acid ethyl ester but using 5 g (22 mmol) of 8-bromo-6-fluoro-2H-chromene to give 1.9 g (30%) of cis-6-fluoro-1,1a,2,7b-tetrahydro-cyclopropa[c]chromene-1-carboxylic acid ethyl ester.

l) +/−cis-4-Bromo-7-fluoro-1,1a,2,7b-tetrahydro-cyclopropa[c]chromene-1-carboxylic acid ethyl ester

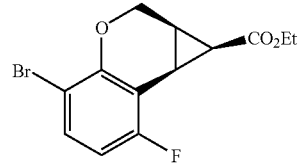

This compound was prepared analogously to +/−cis-4,7-difluoro-1,1a,2,7b-tetrahydro-cyclopropa[c]chromene-1-carboxylic acid ethyl ester but using 3.5 g (15.3 mmol) of 8-bromo-5-fluoro-2H-chromene to give 1.6 g (33%) of +/−cis-4-bromo-7-fluoro-1,1a,2,7b-tetrahydro-cyclopropa[c]chromene-1-carboxylic acid ethyl ester.

m) +/−cis-5,7-Difluoro-1,1a,2,7b-tetrahydro-cyclopropa[c]chromene-1-carboxylic acid ethyl ester

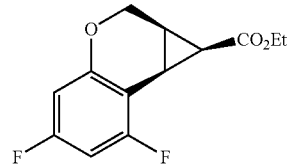

This compound was prepared analogously to +/−cis-4,7-difluoro-1,1a,2,7b-tetrahydro-cyclopropa[c]chromene-1-carboxylic acid ethyl ester but using 2 g (12 mmol) of 5,7-difluoro-2H-chromene-to give 0.9 g (29%) of +/−cis-5,7-difluoro-1,1a,2,7b-tetrahydro-cyclopropa[c]chromene-1-carboxylic acid ethyl ester.

EXAMPLE 58 a) Resolution of the racemic cis-7-fluoro-4-chloro-1,1a,2,7b-tetrahydro-cyclopropa[c]chromene-1-carboxylic acid 0.32 g (1.32 mmol) of racemic cis-7-fluoro-4-chloro-1,1a,2,7b-tetrahydro-cyclopropa[c]chromene-1-carboxylic acid was dissolved in hot acetonitrile (50 ml) and (1R,2R)-2-benzyloxycyclopentylamine (0.25 g, 1.32 mmol) was added. The resulting solution was left for crystallization. After few hours the mother liquor was decanted and crystals were washed with acetonitrile. The second crystallization from acetonitrile gave 92 mg of pure diastereomeric salt. The salt was treated with 1 M HCl and resulting mixture was extracted with ethyl acetate. The organic phase was washed with water, brine and evaporated to give 0.05 g of enantiomeric cis-7-fluoro-4-chloro-1,1a,2,7b-tetrahydro-cyclopropa[c]chromene-1-carboxylic acid.

EXAMPLE 59

+/−cis-N-(5-cyano-2-pyridinyl)-N'-(4,7-dichloro-1,1a,2 7b-tetraydrocyclopropa[c]chromen-1-yl)urea a) 1,4-dichloro-2-(2-propynyloxy)benzene

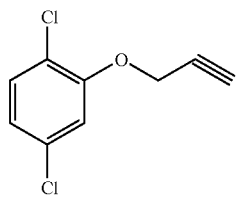

2,5-Dichlorophenol (8 g, 49 mmol) was mixed with potassium carbonate (13.6 g, 98 mmol) and 80% solution of propargyl bromide in toluene (11 ml, 98 mmol) in acetone (100 ml) and stirred overnight at room temperature. The precipitate was removed by filtration and washed with acetone. The acetone solution obtained was concentrated by rotary evaporation and kept under vacuum for 5 h. The product was obtained as yellow oil with quantitative yield. It was used for further transformations without additional purification.

b) 5,8-dichloro-2H-chromene

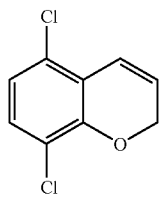

1,4-Dichloro-2-(2-propynyloxy)benzene was degassed and heated at stirring under argon for 4 h at 224° C. The reaction mixture was then distilled in Kugelrohr apparatus (150-175° C./4.1×10$^{-2}$ mbar) to give 3.58 g of desired product as white solid. Yield 36% from starting dichlorophenol.

c) +/−cis-ethyl-4,7-dichloro-1,1a,2,7b-tetrahydrocyclopropa[c]chromene-1-carboxylate

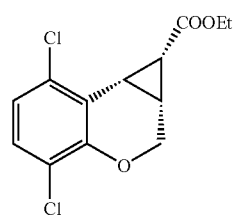

5,8-Dichloro-2H-chromene (3.15 g, 16 mmol), (Rh(II)Ac$_2$)$_2$ (30 mg, 0.1 mol %) was dissolved in degassed dry methylene chloride (3 ml). Ethyl diazoacetate (3 ml, 2 eq.) in the same solvent was added by a syringe at the flow rate 0.4 ml/h over a period of approximately 5 h under N$_2$ atmosphere. The reaction mixture was then washed with NH$_4$Cl(aq), water and brine and the solvent removed. The product (45% cis, 55% trans) was purified by chromatography on silica (200 g, ethyl acetate/n-hexane 1:15) to give 0.9 g of the pure cis product (racemate). Yield 20%. M$^+$=287.

$^1$H-NMR (CDCl$_3$): 7.15 (d, 1H, J=8.5 Hz), 6.91 (d, 1H, J=8.8 Hz), 4.59 (dd, 1H, J$_1$=12.02, J$_2$=7.03), 4.48 (dd, 1H, J$_1$=12.02, J$_2$=4.10), 4.07-3.94 (m, 3H), 2.62 (t, 1H, J=8.8 Hz), 2.27 (t, 1H, J=8.36 Hz), 2.20-2.12 (m, 1H), 1.1 (t, 3H).

d) +/−cis-4,7-dichloro-1,1a,2,7b-tetrahydrocyclopropa[c]chromene-1-carboxylic acid

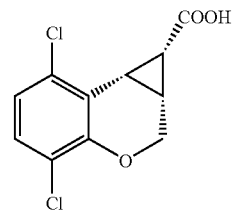

+/−cis-Ethyl-4,7-dichloro-1,1a,2,7b-tetrahydrocyclopropa[c]chromene-1-carboxylate was mixed with methanol (3 ml) and water solution of NaOH (1.5 eq., 3 ml) and heated at stirring for 1.5 h at 60° C. The extraction of basic reaction mixture into hexane showed that no starting material present. The reaction mixture was acidified with excess of 3M HCl solution (pH=1). The precipitate formed was collected by suction and washed with water. White solid obtained was dried under high vacuum (yield 80%).

EXAMPLE 59A a) 5-chloro-2-fluorophenol

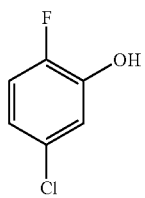

5-Chloro-2-fluoroaniline (10 g, 68 mmol) was dissolved in 6M sulfuric acid and cooled in ice/brine bath to −5° C. The solution of NaNO$_2$ (5.2 g, 76 mmol) in minimum amount of water was added dropwise to the stirred suspension at the temperature not higher then −2° C. After the addition clear yellow solution formed was allowed to stir for additional 30 min at cooling. CuSO$_4$ was dissolved water (80 ml) and mixed with sulfuric acid (32 ml). The diazonium salt solution was added dropwise to the preheated (160° C.) cuprous sulfate solution and the product was removed from the reaction flask by steam distillation. The reaction took about 2 h to be complete. The water/phnol solution was extracted into ether, washed with brine and dried over Na$_2$SO$_4$. Concentration gave 4 g of crude phenol (40%).

b) 4-chloro-1-fluoro-2-(2-propynyloxy)benzene

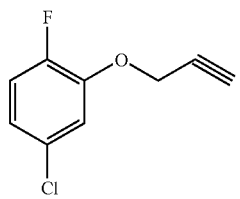

4-Chloro-1-fluoro-2-(2-propynyloxy)benzene was synthesized analogously to Example 33a from (4 g, 27 mmol) 4-chloro-1-fluorophenol to give 4.6 g of product (purified by column chromatography on silica, ethyl acetate/n-hexane 1:15) as yellow oil. Yield 90%.

c) 5-chloro-8-fluoro-2H-chromene

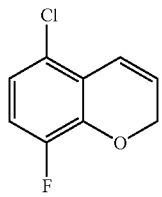

5-Chloro-8-fluoro-2H-chromene was synthesized analogously to Example 33b) from 4-chloro-1-fluoro-2-(2-propynyloxy)benzene (4.6 g, 25 mmol) to give 1 g of product (purified by column chromratography on alumina, ethyl acetate/n-hexane 1:15) as colourless oil. Yield 22%.

d) ethyl +/–cis-7-chloro-4-fluoro-1,1a,2,7b-tetrahydrocyclopropa[c]chromene-1-carboxylate

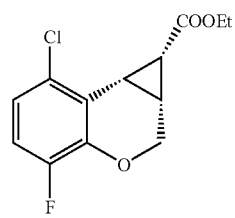

Ethyl +/–cis-7-chloro-4-fluoro-1,1a,2,7b-tetrahydrocyclopropa[c]chromene-1-carboxylate was synthesized analogously to Example 33c from 5-chloro-8-fluoro-2H-chromene (1 g, 5.4 mmol) to give 360 mg of +/–cis product (purified by column chromatography on silica, ethyl acetate/n-hexane 1:20) as white solid. Yield 25%.

e) +/–cis-7-chloro-4-fluoro-1,1a,2,7b-tetrahydrocyclopropa[c]chromene-1-carboxylic acid

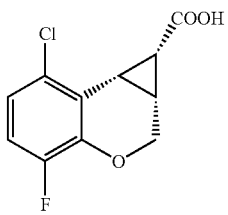

+/–cis-7-Chloro-4-fluoro-1,1a,2,7b-tetrahydrocyclopropa[c]chromene-1-carboxylic acid was synthesized analogously to Example 33d from ethyl +/–cis-7-chloro-4-fluoro-1,1a,2,7b-tetrahydrocyclopropa[c]chromene-1-carboxylate (360 mg, 1.3 mmol) to give 259 mg of +/–cis acid (80%).

EXAMPLE 60

N-[(1S,1aR,7bR) or (1R,1aS,7bS)-1,1a,2,7b-tetrahydrocyclopropa[c][1]benzothiopyran-1-yl]-N'-(5-cyano-2-pyridinyl)urea a) 3,4-dihydro-2H-1-benzothiopyran-4-ol

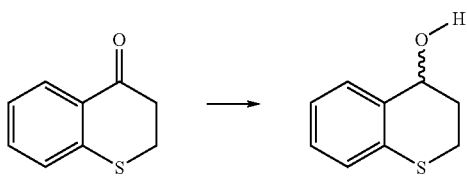

A solution of thiochroman-4-one (9 g) in ether (27 ml) was added slowly to a mixture of lithium aluminium hydride (0.53 g) in ether (54 ml). After the end of the addition, the mixture was refluxed for 2 hours. The reaction mixture was cooled and ice was added, followed by water and by a solution of 20% H$_2$SO$_4$. The water phase was washed twice with ether. The ether phase was washed twice with NaOH 2N, and once with water, dried over MgSO$_4$ and evaporated. The clear oil (8.9 g) crystallised after few hours. Rdt=97% b) 2H-1-benzothiopyran and 4H-1-benzothiopyran

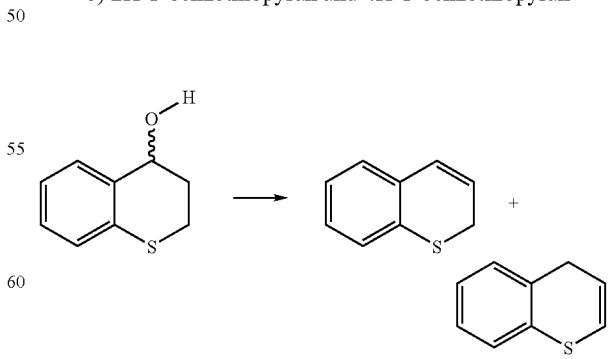

4-Thiochromanol (8.9 g) and potassium acid sulfate (0.89 g) were placed in a flask and evacuated to 1 mm. The flask was put in a bath-heated at 90° C. until the alcohol melted.

The magnetic stirrer was started and the bath slowly brought to 120° C. Dehydration was rapid and a mixture of the product and water distilled and was collected in a ice-cooled receiver. The product was taken up in ether and dried. The crude product (7 g, Rdt=88%) wasn't purified. The NMR showed the presence of 10% of the 4H-1-benzothiopyran.

c) Ethyl ester 1,1a,2,7b-tetrahydro-cyclopropa[c][1] benzothiopyran-1-carboxylic acid, (1S,1aR,7bR) or (1R,1aS,7bS)

Ethyl diazoacetate was added slowly to 500 mg of thiochromene at 140 C. The reaction was followed by Gas chromatography and stopped when all starting material was consumed (about 7 hours). The residue was purified by flash chromatography (5% ether in hexane). The cis isomer (46,5 mg, Rdt=6%) was identified by NMR spectroscopy.

d) 1,1a,2,7b, tetrahydro-cyclopropa[c][1]benzothiopyran-1-carboxylic acid, (1S, 1aR,7bR) or (1R,1aS, 7bS)

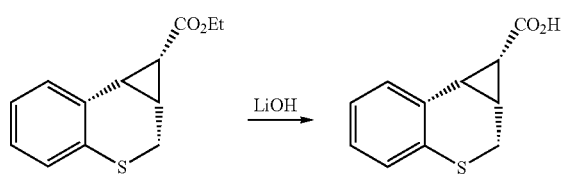

A mixture of the cis isomer (46,5 mg), LiOH (4 eq., 19 mg) in 5 ml of methanol/25% $H_2O$ was refluxed for 1 hour. After evaporation of the solvent under vacuum, the residue was dissolved in water and washed with ether. The water phase was acidified with concentrated HCl, and extracted twice with dichloromethane. After drying, the organic phase was evaporated and gave the desired acid (30 mg). Rdt=73%.

EXAMPLE 61

(1S,1aR,7bS)-4,7-difluoro-1,1a,2,7b-tetrahydrocyclopropa[c]chromene-1-carboxylic acid a) (2Z)-3-(3,6-difluoro-2-methoxyphenyl)-2-propen-1-ol

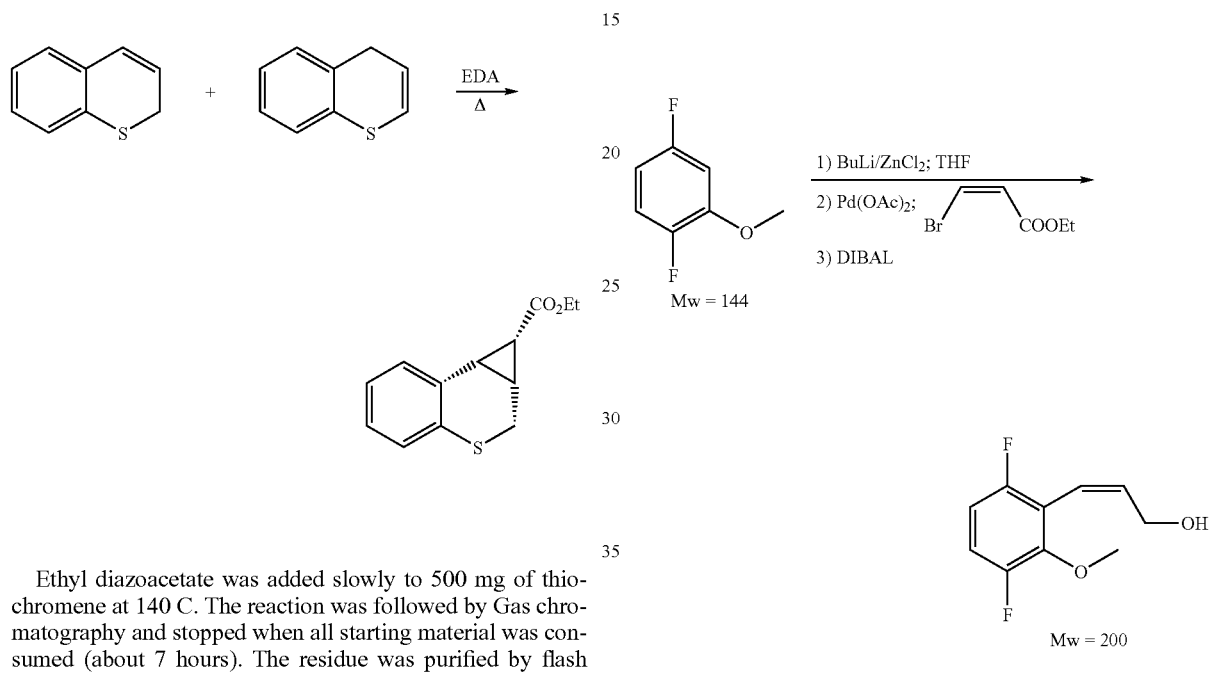

Solution of BuLi (2.5M) in hexane (9.6 ml; 0.024 mol) was added to a stirred solution of 2,5-difluoroanisol (2.88 g, 0.02 mol) in dry THF (30 ml) at −70 C, followed after 2 h by solution of zinc chloride (3.6 g; 0.026 mol) in dry THF (50 ml). The reaction temperature was allowed to raise to room temperature and then stirring was maintained at room temperature for 30 min. $Pd(OAc)_2$ (8 mg; 0.2 mol %) was added, followed by ethyl cis-3-bromoacrylate (3.58 g; 0.02 mol). The reaction mixture was placed in preheated oil bath and heated under reflux for 1 h. The resulting reaction mixture was chilled to −78 C and 60 ml (0.06 mol) of DIBAL (1M solution in hexanes) was added dropwise. The stirring was continued at −78 C for 2 h and 1 h at room temperature. The reaction was quenched with water and all solids were dissolved by addition of HCl. The organic phase was diluted with ether, separated, washed with 5N HCl, brine and evaporated in vacuo. The residue was Kugelrohr distilled ($1.5 \times 10^{-2}$ mbar, 150 C) to give 3.7 g (92%) of crude (2Z)-3-(3,6-difluoro-2-methoxyphenyl)-2-propen-1-ol, which contains ~6% of other regioisomers. The crude product was used in the next step without further purification.

$^1$H-NMR ($CDCl_3$): 7.00 (m, 1H); 6.77 (m, 1H); 6.31 (app. d, 1H); 6.12 (app. dt, 1H); 4.08 (br. t, 2H); 3.89 (d, 3H); 1.80 (br. t, 1H).

b) (2Z)-3-(3,6-difluoro-2-methoxyphenyl)prop-2-enyl diazoacetate

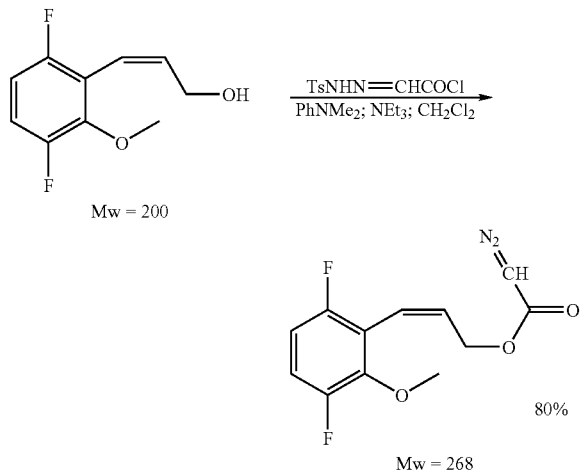

The p-toluenesulfonylhydrozone of glyoxylic acid chloride (5.16 g; 0.02 mol) was added to a solution of (2Z-3-(3,6-difluoro-2-methoxyphenyl)-2-propen-1-ol (3.6 g; 0.018 mol) in dry $CH_2Cl_2$ (50 ml) at −5 C, and N,N-dimethylaniline (2.5 ml; 0.02 mol) was added slowly. After stirring for 30 min at −5 C, $Et_3N$ (12 ml; 0.09 mol) was added slowly. The resulting mixture was stirred for 15 min at −5 C and then for 30 min at room temperature, whereupon water (~50 ml) was added. The organic phase was separated washed with water, brine and concentrated in vacuo. Flash chromatography (silica, EA:Hex; 1:1.5) gave 3.86 g (80%) of product as a yellow solid.

$^1$H-NMR (CDCl$_3$): 7.00 (m, 1H); 6.76 (m, 1H); 6.41 (app. d, J=12.2 Hz; 1H); 6.00 (app. dt, J=12.2; 6.10 Hz; 1H); 4.71 (br. s, 1H); 4.67 (dt, 2H); 3.89 (d, 3H).

c) (1S,5R,6S)-6-(3,6-difluoro-2-methoxyphenyl)-3-oxabicyclo[3.1.0]hexan-2-one

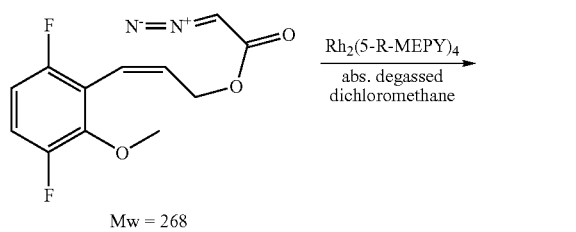

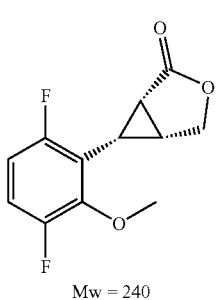

(2Z)-3-(3,6-difluoro-2-methoxyphenyl)prop-2-enyl diazoacetate (3.45 g, 0.013 mol) was dissolved in 100 ml of dried degassed dichloromethane and added dropwise to the solution of chiral Doyle catalyst (Aldrich, also available from Johnsson Matthey, 10 mg, 0.1 mol %) in 50 ml of dichloromethane under argon at ambient temperature over a period of ~6 h. The initial blue color had turned to olive by the end of the addition. The reaction mixture was concentrated in vacuo and the crude product was purified by flash chromatography (silica, EA:Hex, 1:5→1:1) to give 2.72 g (88%) of (1S,5R,6S)-6-(3,6-difluoro-2-methoxyphenyl)-3-oxabicyclo[3.1.0]hexan-2-one as colorless solid. Enantiomeric purity could be checked on this stage using Chiracel OD column, 10% IPA in hexane—94% ee.

$^1$H-NMR (CDCl$_3$): 7.00 (m, 1H); 6.72 (m, 1H); 4.33 (dd, 1H); 4.10 (d, 1H); 402 (d, 3H); 2.66 (m, 2H); 2.37 (t, 1H).

d) (1S,1aR,7b S)-1-(bromomethyl)-4,7-difluoro-1a,7b-dihydrocyclopropa[c]chromene-2(1H)-one

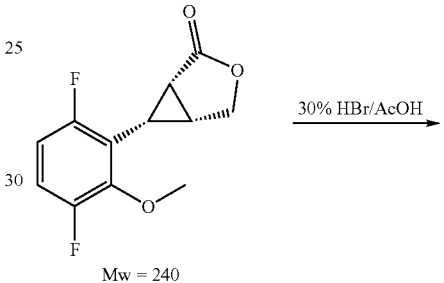

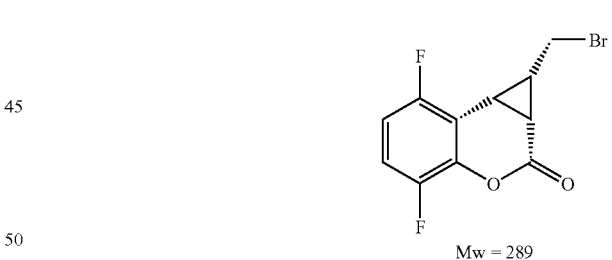

(1S,5R,6S)-6-(3,6-difluoro-2-methoxyphenyl)-3-oxabicyclo[3.1.0]hexan-2-one (130 mg, 0.55 mmol) was mixed with 1.2 ml of 30% HBr/AcOH (6 mmol) and heated in a sealed vessel at stirring for about 4 h at 90° C. The reaction mixture was then cooled down, mixed with water and extracted into diethyl ether (3×20 ml). Ether extract was washed with sat sodium bicarbonate solution and brine. Dried over magnesium sulfate. Concentration gave 160 mg of white solid material. 98% yield.

$^1$H-NMR (CDCl$_3$): 7.08 (m, 1H); 6.88 (m, 1H); 3.44 (dd, 1H); 3.06 (t, 1H); 2.96 (dd, 1H); 2.64 (dd, 1H); 2.46 (m, 1H).

e) (1S,1aR,7bS)-4,7-difluoro-1,1a,2,7b-tetrahydrocyclopropa[c]chromene-1-carboxylic acid

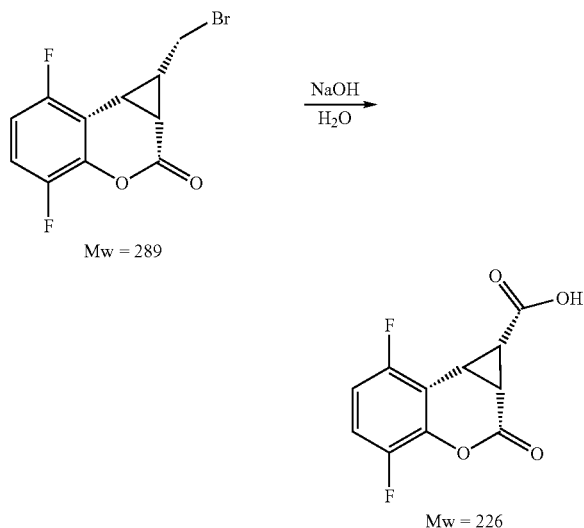

(1S,1aR,7bS)-1-(bromomethyl)-4,7-difluoro-1a,7b-dihydrocyclpropa[c]chromen-2(1H)-one (360 mg, 1.2 mmol) was mixed with the solution of NaOH (0.1 g, 2.5 mmol) in 5 ml of water and heated at stirring for 1 h at 90° C. After completion the reaction mixture was cooled down and extracted into diethyl ether (2×20 ml). Water phase was acidified with conc. HCl. The precipitate formed was collected by filtration to give 180 mg of pure product. Mother liquor was extracted into ether and washed with brine, dried over magnesium sulfate. Concentration gave additional 70 mg of product (containing up to 15% of impurities). Overall yield about 92%.

$^1$H-NMR (CDCl$_3$); 6.86 (m, 1H); 6.54 (m, 1H); 4.48 (m, 2H); 2.62 (t, 1H); 2.20 (t, 1H); 2.11 (m, 1H).

EXAMPLE 62 a) cis ethyl ester 1a,6b-dihydro-1H-benzo[b]cyclopropa[d]thiophene-1-carboxylic acid, (1S,1aS,6bR) or (1R,1aR,6bS)

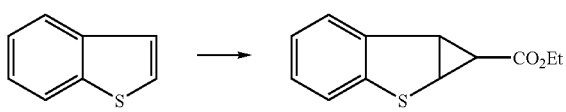

Ethyl diazoacetate is added slowly to 10 g of thiophene at 140° C. The reaction was checked by gas chromatography and stopped after 7 hours. The residue is purified by flash chromatography (5% ether in hexane). The cis isomer (917 mg, Rdt=6%) was identified by NMR spectroscopy.

REFERENCE

Badger G. M. et al, *J. Chem. Soc.*, 1958, 1179-1184.
Badger G. M. et al, *J. Chem. Soc.*, 1958, 4777-4779.

b) cis 1a,6b-dihydro-1H-benzo[b]cyclopropa[d]thiophene-1-carboxylic acid, (1S,1aS,6bR) or (1R,1aR,6bS)

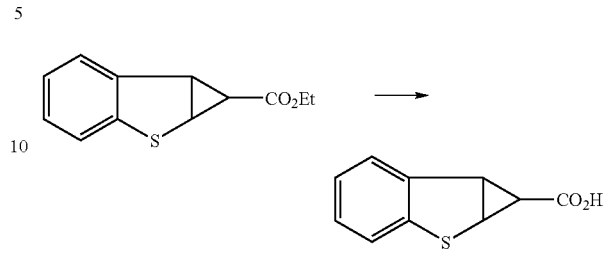

A mixture of the cis isomer (443 mg), LiOH (193 mg) in 15 ml of methanol/25% H$_2$O is refluxed for 1 hour. After evaporation of the solvent under vacuum, the residue is dissolved in water and washed with ether. The water phase is acidified with concentrated HCl, and extracted twice with dichloromethane. After drying, the organic phase is evaporated and gave the desired acid (313.6 mg). Rdt=81%.

EXAMPLE 63

(1S,5R,6S)-6-(3,6-difluoro-2-methoxyphenyl)-2-methoxy-3-oxabicyclo[3.1.0]hexane

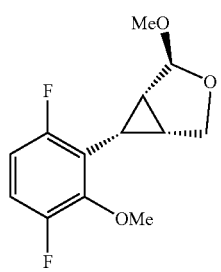

a) Iodo-3-oxabicyclo[3.1.0]hexan-2-one

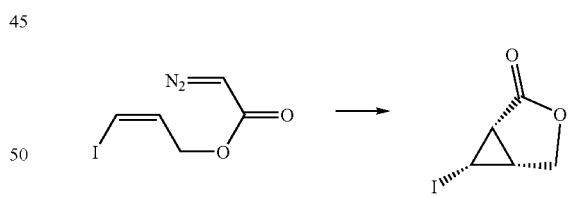

The title compound is synthesised in the depicted stereochemistry as described in Doyle J Amer Chem Soc 117 (21) 5763-5775 (1993)

b) Iodo-2-methoxy-3-oxabicyclo[3,1,0]hexane

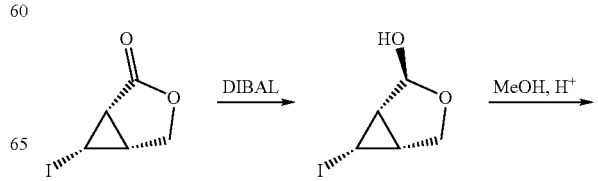

-continued

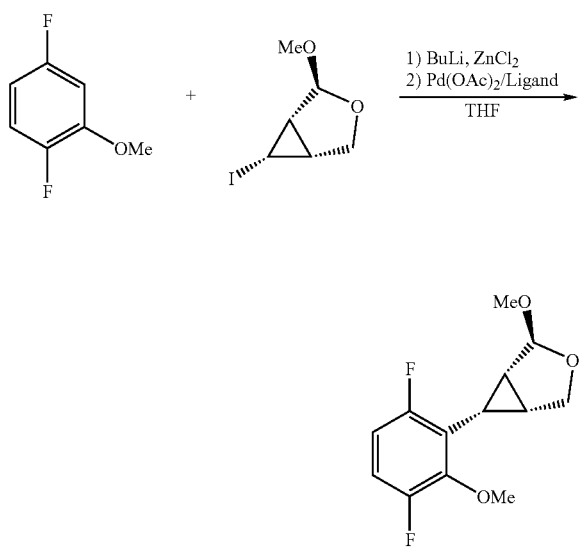

The title compound is synthesised in the depicted stereochemistry as described in Martin et al Tett Lett 39 1521-1524 (1998).

c) (1S,5R,6S)-6-(3,6-difluoro-2-methoxyphenyl)-2-methoxy-3-oxabicyclo[3.1.0]hexane 2,4-diflouroanisol (90 mg, 0.62 mmol) was dissolved in anhydrous, degassed, THF (7 ml) and cooled to −78° C. under $N_2$. nBuLi, 2,5 M in hexane, (0.30 ml, 0.77 mmol) was added and the reaction mixture was stirred at −78° C. for 2 hrs. $ZnCl_2$ (150 mg, 1.1 mmol), as a solution in anhydrous THF (7 ml), was added and the reaction mixture was allowed to warm to ambient temperature for 2 hrs. Iodo-2-methoxy-3-oxabicyclohexane (150 mg, 0.63 mmol), Pd (OAc)$_2$ (1.5 mg, 6.2 mol), and ligand Tris(2,4-di-tert-butylphenyl)phosphite (40 mg, 62 μmol) were mixed in anhydrous THF (7 ml) and added to the reaction mixture. The reaction mixture was heated at reflux for 3 days and quenched with $H_2O$. Diethyl ether was added and the layers were separated, the organic layer was washed with $H_2O$ and aq. sat. NaCl, dried over $MgSO_4$, filtered and concentrated to give the title compound, otherwise denoted 2,4-di-fluoro-5-(cyclopropylacetal)anisol. Column chromatography on silica (EtOAc/Hexane 1:3) gave (4) 50 mg, 31%.

$^1$H NMR (CDCl$_3$) δ (ppm): 6.88-6.94 (m, 1H, ArH), 6.68-6.73 (m, 1 H, ArH), 4.82 (s, 1H, CHOCH$_3$), 3.97-3.98 (m, 1H, CHOCH), 3.94 (s, 3H, OCH$_3$), 3.79-3.81 (m, 1H, CHOCH), 3.30 (s, 3H, OCH$_3$), 2.13-2.19 (m, 2H, 2x CH-cyclopropyl), 1.89 (tr, J=7.81 Hz, 1H, CH cyclopropyl).

EXAMPLE 64 cis-4,7-Difluoro-1,1a,2,7b-tetrahydro-cyclopropa[c]chromene-1-carboxylic acid

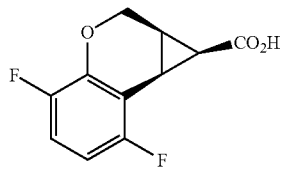

BBr$_3$ 1M solution in CH$_2$Cl$_2$ (5.8 ml; 5.8 mmol 2.1 eq) was added to starting lactone, (1S,5R,6S)-6-(3,6-difluoro-2-methoxyphenyl)-3-oxabicyclo[3.1.0]hexan-2-one from example 42c) (0.66 g; 2.75 mmol) at 0° C. The reaction mixture was stirred at 0° C. for 1 h. Acetonitrile (5.8 ml) was added and stirring was continued for 3 h at 0° C. The reaction mixture was quenched by addition of water and the organic phase was separated. Water phase was extracted with CH$_2$Cl$_2$ and combined organic phases were evaporated. NaOH (0.33 g; 8.25 mmol; 3 eq) in water (~5 ml) was added to the resulted residue and stirred at 80° C. for 45 min. The reaction mixture was extracted with ether to remove none acidic impurities. The residual ether in water phase was evaporated in vacuo and conc. HCl was added to pH of ~3. After ~1 h the solid was filtered off yielding 0.497 g (80%) of crude final acid as brownish solid. The crude acid was dissolved in 6 ml of EtOH/H$_2$O (40/60 v/v) and treated with activated carbon. The hot solution was filtered and left for crystallization. Yield 0.4 g (64%).

$^1$H-NMR (CDCl$_3$): 10.32 (br s, ~1H), 7.68 (d, 2H), 7.37 (s, 1H), 7.32 (d, 2H), 6.96 (s, 1H), 6.87 (m, 1H), 6.62 (dt, 1H), 4.44 (dd, 1H), 4.33 (dd, 1H), 3.53 (m, 1H), 2.56 (m, ~1H), 1,96 (m, 1H). LC-MS: M$^+$434.

EXAMPLE 65 a) 1,1a,66a-tetrahydrocyclopropa[a]indene-1-carboxylic acid ethyl ester

Indene is diluted in 100 ml dichloroethane. Around 10 mg of CuI and around 10 mg Pd(OAc)$_2$ is added. 25 ml of the resultant mixture is dropwise added to 25 ml ethyldiazoacetate and refluxed for 30 minutes. The solution is filtered through Al$_2$O$_3$ which is eluted with a EtOAC/hexane gradient. The eluate is evaporated vigorously at 100°, 2 mmHg to yield the title compound (36 g).

b) 1,1a,66a-tetrahydrocyclopropa[a]indene-1-amine

The product of step a) is boiled with around 50 g NaOH in 200 ml 10:1MeOH:H$_2$O for 2 hours. The mixture is diluted with water, washed with dichloroethane, evaporated with HOAc, extracted with dichloroethane, washed with water, dried with sulphate, filtered and evaporated to yield 25 g of the acid, 95% pure. DPPA 275.2 δ=1.128 10 ml, 46.5 mmol TEA 7.1 ml 1.1ee and 7.3 g of the acid (mass 174.12, 0.9ee) is mixed in 200 ml toluene and refluxed for around 2 hours. The product is evaporated and dissolved in dioxane 200 ml. 25 ml HCl(aq) and 25 ml water is added and the mixture agitated for 60 minutes at room temperature. The solution is partioned with acid/base in water/dichloroethiane. The organic, phase is dired, filtered and evaporated. The product is chromatographed through a silica 60 column to yield 660 mg of 85% pure cis amine, mol wt 145.11.

EXAMPLE 66

±cis-1-(5-Cyano-pyridin-2-yl)-3-(1,1a,6,6a-tetrahydro-cyclopropa[a]inden-1-yl)-urea a) ±cis-1,1a,6,6a-Tetrahydro-cyclopropa[a]indene-1-carboxylic acid ethyl ester To a mixture of indene (11.6 g, 100 mmol) and $Cu_2Br_2$ (0.10 g, 0.35 mmol) in 1,2-dichloroethane

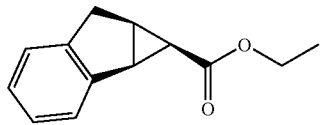

(200 mL) at 80° C., was added dropwise (3 h) a solution of ethyl diazoacetate (17.1 g, 150 mmol) in 1,2-dichloroethane (35 mL). After 15 min at 80° C., the reaction mixture was washed with $H_2O$ (200 mL). The $H_2O$ phase was washed with $CH_2Cl_2$ (50 mL) and the solvent of the combined organic phases was removed under reduced pressure. The crude product was column chromatographed (silica gel, 5→10% EtOAc in Hexane), to give 3.63 g (18%) of ±cis-1,1a,6,6a-tetrahydro-cyclopropa[a]indene-1-carboxylic acid ethyl ester and 6.68 g (33%) of ±trans-1,1a,6,6a-tetrahydro-cyclopropa[a]indene-1-carboxylic acid ethyl ester as a byproduct.

$^1$H-NMR ($CDCl_3$): 7.30-7.05 (m, 4H), 3.81 (q, 2H), 3.36 (d, 1H), 3.18 (dd, 1H), 2.92 (m, 1H), 2.24 (m, 1H), 1.99 (dd, 1H), 0.92 (t, 3H).

b) ±cis-1,1a,6,6a-Tetrahydro-cyclopropa[a]indene-1-carboxylic acid

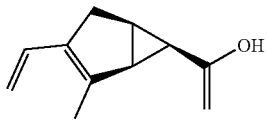

±cis-1,1a,6,6a-Tetrahydro-cyclopropa[a]indene-1-carboxylic acid was synthesized from ±cis-1,1a,6,6a-tetrahydro-cyclopropa[a]indene-1-carboxylic acid ethyl ester (3.53 g, 15.5 mmol), LiOH (539 mg, 22.5 mmol), $H_2O$ (10 mL) and MeOH (20 mL) which were heated to reflux for 2 h, concentrated and acidified to precipitate 1.62 g (62%) of ±cis-1,1a,6,6a-tetrahydro-cyclopropa[a]indene-1-carboxylic acid as a white solid. The product was not crystallized.

$^1$H-NMR ($CDCl_3$): 10.95 (br s, 1H, 7.35-7.02 (m, 4H), 3.29 (d, 1H), 3.14 (dd, 1H), 2.96 (m, 1H), 2.27 (m, 1H), 1.91 (dd, 1H).

The reaction mixture was concentrated under reduced pressure, benzene (20 mL) was added and the reaction mixture was washed with 1N HCl (30 mL), $H_2O$ (30 mL) and brine (30 mL). The solvent of the organic phases was removed under reduced pressure. The crude product was column chromatographed (silica gel, 4→5% MeOH in $CH_2Cl_2$), to give 25 mg (5%) of ±cis-1-(5-cyano-pyridin-2-yl)-3-(1,1a,6,6a-tetrahydro-cyclopropa[a]inden-1-yl)-urea.

$^1$H-NMR (DMSO-$d_6$): 9.58 (s, 1H), 8.18 (d, 1H), 7.96 (dd, 1H), 7.40-7.25 (m, 3H), 7.17-7.05 (m, 3H), 3.27-3.13 (m, 2H), 2.80-2.73 (m, 2H), 2.05 (dd, 1H).

EXAMPLE 67

±cis-1-(5-Cyano-pyridin-2-yl)-3-(1a,2,3,7b-tetrahydro-cyclopropa[a]naphthalen-1-yl)-urea a) 1a,2,3,7b-Tetrahydro-1H-cyclopropa[a]naphthalene-1-carboxylic acid ethyl ester 1a,2,3,7b-Tetrahydro-1H-cyclopropa[a]naphthalene-1-carboxylic acid ethyl ester was

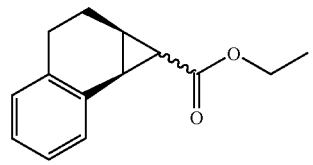

Synthesized analogously to Example 66 from 1,2-dihydronaphthalene (3.91 g, 30 mmol), to give 688 mg (11%) of 1a,2,3,7b-tetrahydro-1H-cyclopropa[a]naphthalene-1-carboxylic acid ethyl ester (a 56/39 mixture of cis and trans isomers).

$^1$H-NMR ($CDCl_3$): 7.35-6.95 (m, 4H), 4.30-3.85 (m, 2H), 2.90-1.00 (m, 10H).

b) 1a,2,3,7b-Tetrahydro-1H-cyclopropa[a]naphthalene-1-carboxylic acid

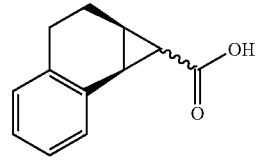

1a,2,3,7b-Tetrahydro-1H-cyclopropa[a]naphthalene-1-carboxylic acid was synthesized analogously to Example 66b from 1a,2,3,7b-tetrahydro-1H-cyclopropa[a]naphthalene-1-carboxylic acid ethyl ester (688 mg, 3.18 mmol, a 56/39 mixture of cis and trans isomers), to give 540 mg (90%) of 1a,2,3,7b-tetrahydro-1H-cyclopropa[a]naphthalene-1-carboxylic acid (a 56/39 mixture of cis and trans isomers). The product was not crystallized.

$^1$H-NMR ($CDCl_3$): 11.36 (br s, 1H), 7.30-6.95 (m, 4H), 2.80-1.65 (m, 7H).

EXAMPLE 68 a) 1,1a,2,3,4,8b-Hexahydro-benzo[a]cyclopropa[c]cycloheptene-1-carboxylic acid ethyl ester

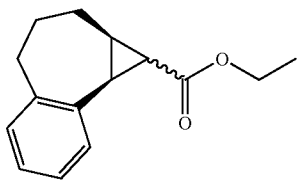

1,1a,2,3,4,8b-Hexahydro-benzo[a]cyclopropa[c]cycloheptene-1-carboxylic acid ethyl ester was synthesized analogously to Example 66a from 6,7-dihydro-5H-benzocycloheptane (4.40 g, 30.5 mmol), to give 3.43 g (49%) of 1,1a,2,3,4,8b-hexahydro-benzo[a]cyclopropa[c]cycloheptene-1-carboxylic acid ethyl ester (a 1/10 mixture of cis and trans isomers).

$^1$H-NMR (CDCl$_3$): 7.40-6.90 (m, 4H), 4.30-4.00 (m, 2H), 3.30-0.50 (m, 12H).

b) 1,1a,2,3,4,8b-Hexahydro-benzo[a]cyclopropa[c]cycloheptene-1-carboxylic acid 1,1a,2,3,4,8b-Hexahydro-benzo[a]cyclopropa[c]cycloheptene-1-carboxylic acid was

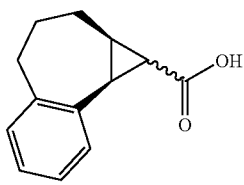

synthesized analogously to Example 66 from 1,1a,2,3,4,8b-hexahydro-benzo[a]cyclopropa[c]cycloheptene-1-carboxylic acid ethyl ester (3.43 g, 14.9 mmol, a 1/10 mixture of cis and trans isomers), to give 2.81 g (93%) of 1,1a,2,3,4,8b-hexahydro-benzo[a]cyclopropa[c]cycloheptene-1-carboxylic acid (a 1/10 mixture of cis and trans isomers). The product was not crystallized.

$^1$H-NMR (CDCl$_3$): 10.76 (br s, 1H), 7.40-7.00 (m, 4H), 3.30-0.50 (m, 9H).

EXAMPLE 69 a) 6-methoxy-1,2,3,4-tetrahydronaphthalen-1-ol

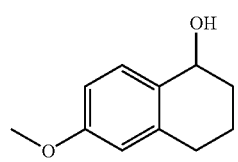

6-Methoxytetralone (10 g, 0.057 mol) was mixed with 150 ml of dry ethanol and sodium borohydride (1.2 eq) was added by portions to the stirred mixture. The reaction mixture was left to stir at ambient temperature for 15 h. The reaction mixture was then concentrated by rotary evaporation, mixed with 100 ml of water and heated for 1 h at 45° C. The resulting mixture was extracted into diethyl ether (3×80 ml). Combined organic extract was dried over Na$_2$SO$_4$ and concentrated by rotary evaporation to give 10.39 g of yellow oil which was used in the next step without additional purification.

b) 7-methoxy-1,2-dihydronaphthalene

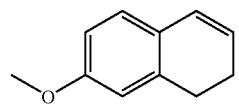

Crude 6-methoxy-1,2,3,4-tetrahydronaphthalen-1-ol (10.3 g, 0.058 mol) was dissolved in 100 ml of toluene and heated in an oil bath (115° C.). P-tolylsulphonic acid (20 mg) was added to the reaction mixture and it was refluxed for about 1 h. The reaction was monitored by GC. The reaction mixture was then cooled and washed with sat. NaHCO$_3$ solution, water and brine and organic layer was dried over Na$_2$SO$_4$. Concentration gave 8.87 g of light brown oil. Yield 96%.

c) Ethyl 5-methoxy-1a,2,3,7b-tetrahydro-1H-yclopropa[a]aphthalene-1-carboxylate

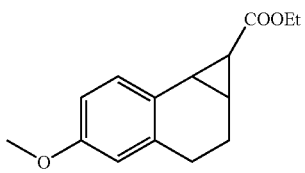

7-Methoxy-1,2-dihydronaphthalene (8.8 g, 0.055 mol) was mixed with 10 ml of degassed absolute methylene chloride and 20 mg of rhodium acetate (appr. 0.1 mol %. The reaction mixture was bubbled with nitrogen and ethyl diazoacetate (2 eq, 50% solution in degassed abs. methylene chloride) was added slowly through the syringe (flow rate about 1 ml/hour) to the stirred solution at ambient temperature. Gas evolution started upon the addition. The reaction was monitored by GC. Additional amount of catalyst was added during the reaction (about 20 mg). GC-ratio of cis/trans isomers was 21:48.

After the reaction was complete according to GC data the reaction mixture was washed with saturated NH$_4$Cl solution and brine. The methylene chloride solution was dried over Na$_2$SO$_4$. Concentration gave 13 g of crude product as yellow oil. Purified by column chromatography on silica (200 g, ethyl acetate/hexane 1:20). Only trans isomer was obtained in pure form. The required cis form could not be purified by the technique used. Fractions which were more enriched with required product were combined (200 mg, cis/trans ratio 70:30 according to GC) and used for further transformations.

d) 5-Methoxy-1a,2,3,7b-tetrahydro-1H-cyclopropa[a]naphthalene-1-carboxylic acid

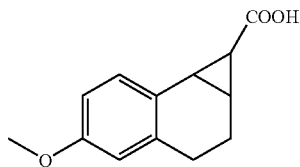

Ethyl 5-methoxy-1a,2,3,7b-tetrahydro-1H-cyclopropa[a]naphthalene-1-carboxylate (0.2 g, 0.8 mmol) was dissolved in 2 ml of methanol and the solution of sodium hydroxide (0.2 g, 50 mmol) in 2 ml of water was added to the reaction mixture and stirred at ambient temperature overnight. The extraction of basic reaction mixture into hexane showed that no starting material present. The reaction mixture was acidified with excess of 3M HCl solution (pH=1), and extracted into ethylacetate (3×15 ml). The combined extracts were washed with water and brine, dried over $Na_2SO_4$ and concentrated by rotary evaporation to give 0.1 5 g of mixture of cis/trans acids as white solid.

EXAMPLE 70 a) 7-methoxy-1,2,3,4-tetrahydro-1-naphthalenol

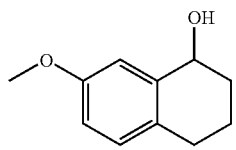

7-Methoxy-3,4-dihydro-1(2H)-naphthalenol was synthesized analogously to Example 69a from 7-methoxy-1,2,3,4-tetrahydro-1-naphthalenone (5 g, 28 mmol), to give about 5 g of crude product (quantitative yield), which was used in the next step without additional purification.

b) 6-methoxy-1,2-dihydronaphthalene

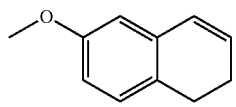

6-Methoxy-1,2-dihydronaphthalene was synthesized analogously to Example 69b from 7-methoxy-1,2,3,4-tetrahydro-1-naphthalenol to give 4.4 g of product as brown yellow oil (96% yield from 7-methoxy-1,2,3,4-tetrahydro-1-naphthalenone).

c) ethyl 6-methoxy-1a,2,3,7b-tetrahydro-1H-cyclopropa[a]naphthalene-1-carboxylate

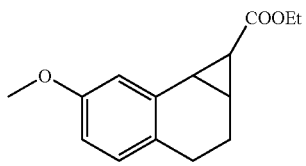

Ethyl 6-methoxy-1a,2,3,7b-tetrahydro-1H-cyclopropa[a]naphthalene-1-carboxylate was synthesized analogously to Example 67 from 6-methoxy-1,2-dihydronaphthalene (4.4 g, 28 mmol) at addition rate 0.7 ml/h to give 9.68 g of crude product as orange-brown oil. Purified by column chromatography on silica (200 g, ethylacetate/hexane 1:10). Three fractions were collected: fraction enriched with cis isomer (75% by GC)—0.16 g, mixed fraction—1.76 g, and fraction contained pure trans isomer—1 g. Total yield 45%.

d) 6-methoxy-1a,2,3,7b-tetrahydro-1H-cyclopropa[a]naphthalene-1-carboxylic acid

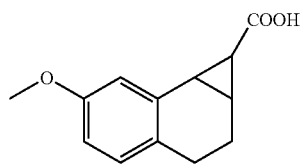

6-Methoxy-1a,2,3,7b-tetrahydro-1H-cyclopropa[a]naphthalene-1-carboxylic acid was synthesized analogously to Example 69d) from ethyl 6-methoxy-1a,2,3,7b-tetrahydro-1H-cyclopropa[a]naphthalene-1-carboxylate (0.16 g, 0.65 mmol) to give 0.1 g of product as white crystals. Yield 71%.

EXAMPLE 71 a) 7,8-dihydro-2-naphthalenol

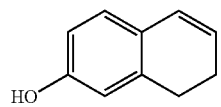

7-Methoxy-1,2-dihydronaphthalene (6.4 g, 40 mmol) was dissolved in abs. DMF and bubbled with argon sodium ethylthiolate (2.5 eq) was added and the reaction mixture was heated at stirring at 160° C. for about 4 h. Reaction was monitored by GC. Reaction mixture was diluted with water, acidified with 3M HCl and extracted into ethylacetate. Organic extract was washed with water and brine, dried over $Na_2SO_4$ and concentrated by rotary evaporation. Purification by column chromatography on silica (200 g, ethylacetate/hexane) gave 5.36 g of desired phenol. Yield 92%.

b) 7,8-dihydro-2-naphthalenyl trifluoromethanesulfonate

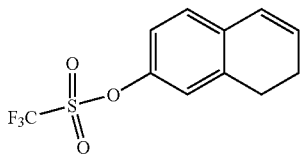

7,8-Dihydro-2-naphthalenol (5.3 g, 37 mmol) was mixed with triethylamine (6.2 ml, 44 mmol) in abs. methylenechrloride and cooled under nitrogen in the ice/brine bath. Triflic anhydride (7.4 ml, 44 mmol) was added to the stirred solution through syringe during 10 min. The temperature was allowed to rise slowly up to room temperature. The reaction mixture was then washed with water and brine and dried over $Na_2SO_4$. The crude product was purified by column chromatography on silica. 9 g of brown liquid was obtained. Yield 88%.

c) Ethyl 5-{[(trifluoromethyl)sulfony]oxy}-1a,2,3,7b-tetrahydro-1H-cyclopropa[a]naphthalene-1-carboxylate

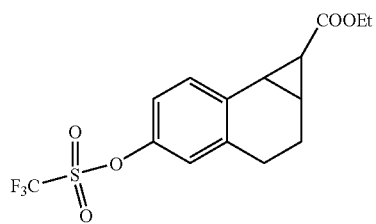

Ethyl 5-{[(trifluoromethyl)sulfonyl]oxy}-1a,2,3,7b-tetrahydro-1H-cyclopropa[a]naphthalene-1-carboxylate was synthesized analogously to Example 5c from 7,8-dihydro-2-naphthalenyl trifluoromethanesulfonate (9 g, 32 mmol) at addition rate 1 ml/h to give 13 g of crude product as orange-brown oil. Purified by column chromatography on silica (200 g, ethylacetate/hexane 1:15). Fraction enriched with cis isomer (80% by GC)—0.64 g was collected and used for futher transformations.

d) Ethyl 5-cyano-1a,2,3,7b-tetrahydro-1H-cyclopropa[a]naphthalene-1-carboxylate

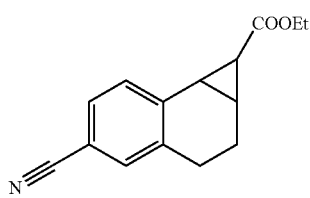

Ethyl 5-{[(trifluoromethyl)sulfonyl]oxy}-1a,2,3,7b-tetrahydro-1H-cyclopropa[a]naphthalene-1-carboxylate (0.2 g, 0.5 mmol) was mixed with $Zn(CN)_2$ (0.82 mmol) and $Pd(Ph_3P)_4$ (56 mg, 10 mol %) in DMF (4 ml), bubbled with argon for 5 min and heated at stirring in a closed vial for 14 h at 100° C. Reaction was monitored by GC. The reaction mixture was concentrated by rotary evaporation, mixed with saturated $NH_4Cl$ and extracted into ethylacetate (3×15 ml). Organic extract was washed with water and brine, dried under $Na_2SO_4$. Concentration gave 0.12 g of product as an oil (yield 90%).

d) 5-cyano-1a,2,3,7b-tetrahydro-1H-cyclopropa[a]naphthalene-1-carboxylic acid

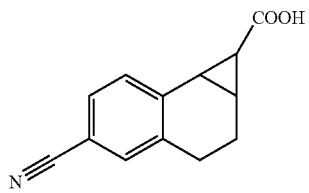

5-Cyano-1a,2,3,7b-tetrahydro-1H-cyclopropa[a]naphthalene-1-carboxylic acid was synthesized analogously to Example 69d from ethyl 5-cyano-1a,2,3,7b-tetrahydro-1H-cyclopropa[a]naphthalene-1-carboxylate (0.12 g, 0.5 mmol) to give 0.1 g of product as white crystals. Yield 94%.

$^1$H-NMR (DMSO-$d_6$): 9.70 (br s, 1H), 8.32 (br s, 1H), 8.03 (dd, 1H), 7.46-7.63 (m, 4H), 7.32 (br s, 1H), 3.18-3.10 (m, 2H), 2.76-2.65 (m 1H), 2.62-2.51 (m, 1H), 2.34 (t, 1H), 2.01-1.80 (br m, 2H), 1.78-1.69 (br m, 1H).

EXAMPLE 71A a) Ethyl 5-[(trimethylsilyl)ethynyl]-1,1a,2,3,7b-tetrahydro-1H-cyclopropa[a]naphthalene-1-carboxylate

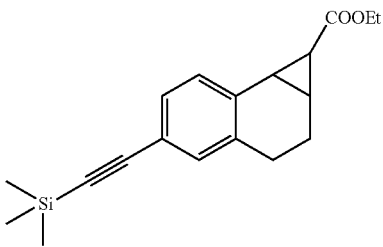

Ethyl 5-{[(trifluoromethyl)sulfonyl]oxy}-1a,2,3,7b-tetrahydro-1H-cyclopropa[a]naphthalene-1-carboxylate (0.2 g, 0.5 mmol) was mixed with trimethylsylilacetylene (0.2 ml, 1.37 mmol), DPP (35 mg, 10 mol %), $Pd(dba)_2$ (30 mg, 10 mol %) and CuI (3 mg) in $Et_3N$ (2.5 ml), bubbled with argon for 5 min and heated at stirring in a closed vial for 14 h at 95° C. Reaction was monitored by GC. The reaction mixture was concentrated by rotary evaporation, mixed with saturated $NH_4Cl$ and extracted into ethylacetate (3×15 ml). Organic extract was washed with water and brine, dried under $Na_2SO_4$. Concentration gave 0.15 g of product as an oil (yield 87%).

b) 5-Ethynyl-1a,2,3,7b-tetrahydro-1H-cyclopropa[a]naphthalene-1-carboxylic acid

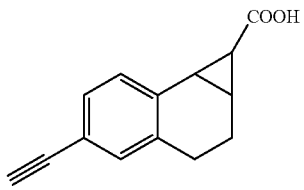

Ethyl 5-[(trimethylsilyl)ethynyl]-1a,2,3,7b-tetrahydro-1-H-cyclopropa[a]naphthalene-1-carboxylate (0.2 g, 0.64 mmol) was dissolved in 4 ml of methanol and the solution of sodium hydroxide (0.05 g, 1.2 mmol) in 2 ml of water was added to the reaction mixture and stirred at heating at 65° C. for 6 h. The extraction of basic reaction mixture into hexane showed that no starting material present. The reaction mixture was acidified with excess of 3M HCl solution (pH=1), and extracted into ethylacetate (3×15 ml). The combined extracts were washed with water and brine, dried over $Na_2SO_4$ and concentrated by rotary evaporation to give 0.12 g of mixture of cis/trans acids (85:15) as white solid. Yield 88%. 7

EXAMPLE 72 a) 5,8-difluoro-4-methyl-3,4-dihydro-1(2H)-naphthalenone

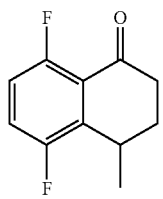

1,4-Difluorobenzene (22 ml, 210 mmol) was mixed with gamma-valerolactone (4 ml, 42 mmol) and $AlCl_3$ (28 g, 210 mmol) was added by portions to the stirred reaction mixture. The reaction mixture was then refluxed at stirring for 16 h (oil bath 110° C.). The reaction mixture was cooled down (ice/brine bath) and ice/conc. HCl was added and stirred until homogeneous mixture was obtained. The reaction mixture was then extracted into methylene chloride, washed with water (4×10 ml) and sodium bicarbonate solution (3×100 ml). The organic extract was dried over $Na_2SO_4$. Concentration by rotary evaporation gave 6.7 g of product as yellow powder. Yield 81%.

b) 5,8-difluoro-4-methyl-1,2,3,4-tetrahydro-1-naphthalenol

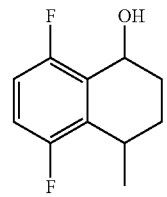

5,8-Difluoro-4-methyl-1,2,3,4-tetrahydro-1-naphthalenol was synthesized analogously to Example 69a from 5,8-difluoro-4-methyl-3,4-dihydro-1(2H-naphthalenone to give 1.8 g of crude product, which was used in the next step without additional purification.

c) 5,8-difluoro-1-methyl-1,2-dihydronaphthalene

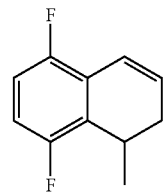

5,8-Difluoro-1-methyl-1,2-dihydronaphthalene was synthesized analogously to Example 69b from 5,8-difluoro-4-methyl-1,2,3,4-tetrahydro-1-naphthalenol (1.8 g, 9.1 mmol) to give 1.5 g of product as brown yellow oil (90% yield from 5,8-difluoro-4-methyl-1,2,3,4-tetrahydro-1-naphthalenone).

d) Ethyl 4,7-difluoro-3-methyl-1a,2,3,7b-tetrahydro-1H-cyclopropa[a]naphthalene-1-carboxylate

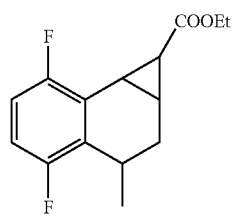

Ethyl 4,7-difluoro-3-methyl-1a,2,3,7b-tetrahydro-1H-cyclopropa[a]naphthalene-1-carboxylate was synthesized analogously to Example 69c from 5,8-difluoro-1-methyl-1,2-dihydronaphthalene (3.5 g, 19 mmol) at addition rate 0.5 ml/h to give crude product as yellow-brown oil. Purified by column chromatography on silica (200 g, ethylacetate/hexane 1:15) to give 5.2 g of the mixture of diastereomeric esters together with dimers of EDA as colourless oil (GC ratio: anti-45%; 40% /trans:cis/, syn-11%; 2.3% /trans:cis/).

e) +/−anti-cis-4,7-difluoro-3-methyl-1a,2,3,7b-tetrahydro-1H-cyclopropa[a]naphthalene-1-carboxylic acid

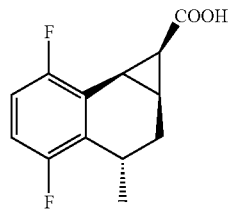

Ethyl 4,7-difluoro-1a,2,3,7b-tetrahydro-1H-cyclopropa[a]naphthalene-1-carboxylate (5.25 g, 20 mmol, ~50:50 mixture of cis and trans isomers) was dissolved in 2.5 ml of methanol and the solution of sodium hydroxide (0.4 g, 10 mmol) in 2.5 ml of water was added to the reaction mixture and stirred at ambient temperature overnight. The reaction mixture was extracted into hexane (3×30 ml). The combined extracts were washed with water and brine, dried over Na$_2$SO$_4$ and concentrated by rotary evaporation to give 1.12 g of cis esters as colourless oil (mixture of ethyl and methyl esters—94% according to GC). The mixture obtained was dissolved in 1.5 ml of methanol and the solution of sodium hydroxide (0.2 g, 5 mmol) in 1.5 ml of water was added to the reaction mixture and stirred at 95° C. for 40 min. The reaction mixture was acidified with excess of 3M HCl solution (pH=1), and extracted into ethylacetate (3×15 ml). The combined extracts were washed with water and brine, dried over Na$_2$SO$_4$ and concentrated by rotary evaporation to give 0.93 g anti-+/−cis acid as slightly orange crystals. Yield 20% (appr. quantitative if calculated for starting cis isomer).

EXAMPLE 73 a) 4,7-difluoro-3-methyl-1-indanone

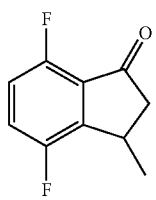

4,7-Difluoro-3-methyl-1-indanone was synthesized analogously to Example 72a from beta-butyrolactone (4 ml, 52 mmol) to give 7.19 g of yellow powder (85:15 mixture of corresponding indanone and tertralone according to GC). The product was purified by column chromatography on silica (200 g, ethylacetate/hexane) to give 3.7 g (40% yield) of pure product together with mixed fraction and fraction containing pure tetralone.

b) 4,7-difluoro-3-methyl-1-indanol

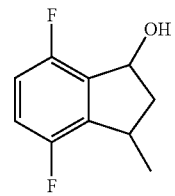

4,7-Difluoro-3-methyl-1-indanol was synthesized analogously to Example 69 from 4,7-difluoro-3-methyl-1-indanone (3.7 g, 20 mmol), to give about 3.75 g of crude product (quantitative yield), which was used in the next step without additional purification.

c) 4,7-Difluoro-1-methyl-1H-indene

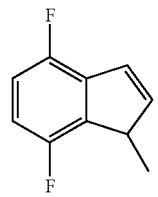

4,7-Difluoro-1-methyl-1H-indene was synthesized analogously to Example 66 from 4,7-difluoro-3-methyl-1-indanol (3.75 g, 9.1 mmol) to give 2.36 g of product as beige liquid (70% yield).

d) Ethyl 2,5-difluoro-6-methyl-1,1a,6,6a-tetrahydrocyclopropa[a]indene-1-carboxylate

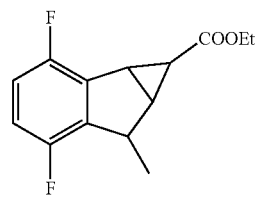

Ethyl 2,5-difluoro-6-methyl-1,1a,6,6a-tetrahydrocyclopropa[a]indene-1-carboxylate was synthesized analogously to Example 69c from 4,7-difluoro-1-methyl-1H-indene (1.32 g, 7.9 mmol) at addition rate 0.4 min to give crude product as yellow-brown oil. Purified by column chromatography on silica (100 g, ethylacetate/hexane 1:15) to give 0.61 g of the mixture of diastereomeric esters cis- and trans-esters as colourless oil (cis/trans ratio: 84:16 according to NMR). Yield 30%.

e) anti-+/−cis-2,5-difluoro-6-methyl-1,1a,6,6a-tetrahydrocyclopropa[a]indene-1-carboxylic acid

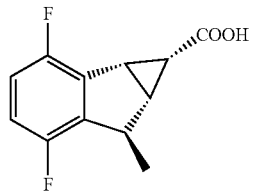

anti-+/−cis-2,5-Difluoro-6-methyl-1,1a,6,6a-tetrahydrocyclopropa[a]indene-1-carboxylic acid was synthesized analogously to Example 34 from ethyl 2,5-difluoro-6-methyl-1,1a,6,6a-tetrahydrocyclopropa[a]indene-1-carboxylate (0.61 g, 2.4 mmol) by stepwise hydrolysis first with 20 mol. % of NaOH and then with the excess of NaOH at heating to give 380 mg of product as white crystals. Yield 70% (appr. quantitative if calculated for starting cis isomer).

EXAMPLE 74 a) 5,8-difluoro-3,4-dihydro-1(2H)-naphthalenone

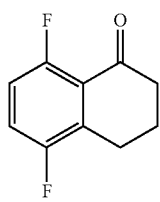

5,8-Difluoro-3,4-dihydro-1(2H)-naphthalenone was synthesized together with 4,7-difluoro-3-methyl-1-indanone according to procedure described in Example 73a. Separated by column chromatography on silica. 0.77 g of pure product was obtained yield 8%.

b) 5,8-difluoro-1,2,3,4-tetrahydro-1-naphthalenol

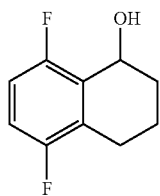

5,8-Difluoro-1,2,3,4-tetrahydro-1-naphthalenol was synthesized analogously to Example 69a from 5,8-difluoro-3,4-dihydro-1(2H)-naphthalenone (0.77 g, 4.2 mmol), to give crude product (quantitative yield), which was used in the next step without additional purification.

c) 5,8-difluoro-1,2-dihydronaphthalene

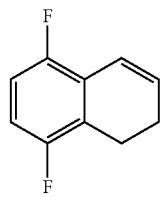

5,8-Difluoro-1,2-dihydronaphthalene was synthesized analogously to Example 69b from 5,8-difluoro-1,2,3,4-tetrahydro-1-naphthalenol to give 0.67 g of crude product as brownish liquid (90% yield from 5,8-difluoro-3,4-dihydro-1 (2H)-naphthalenone).

Additional amount of product was also obtained from the mixture of 5,8-difluoro-3,4-dihydro-1(2H)-naphthalenone and 4,7-difluoro-3-methyl-1-indanone by reduction followed by dehydration. The mixture of corresponding indene and naphthalene is easy to separate by column chromatography on silica (ethyl acetate/hexane 1:20).

d) ethyl 4,7-difluoro-1a,2,3,7b-tetrahydro-1H-cyclopropa[a]naphthalene-1-carboxylate

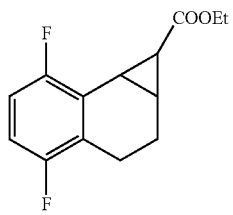

Ethyl 4,7-difluoro-1a,2,3,7b-tetrahydro-1H-cyclopropa[a]naphthalene-1-carboxylate was synthesized analogously to Example 69c from 5,8-difluoro-1,2-dihydronapthalene (0.7 g, 4.2 mmol) at addition rate 0.4 ml/h to give crude product as yellow-brown oil. Purified by column chromatography on silica (100 g, ethylacetate/hexane 1:15) to give 0.45 g of the mixture of cis- and trans-esters as colourless oil (cis/trans ratio: 33:67 according to GC) 4,7-difluoro-1a,2,3, 7b-tetrahydro-1H-cyclopropa[a]naphthalene-1-carboxylic acid e) 4,7-Difluoro-1a,2,3,7b-tetrahydro-1H-cyclopropa[a]naphthalene-1-carboxylic acid

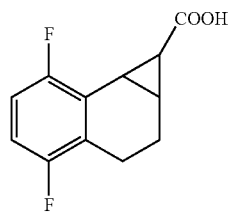

4,7-Difluoro-1a,2,3,7b-tetrahydro-1H-cyclopropa[a]naphthalene-1-carboxylic acid was synthesized analogously to Example 72e from ethyl 4,7-difluoro-1a,2,3,7b-tetrahydro-1H-cyclopropa[a]naphthalene-1-carboxylate (0.45 g, 1.8 mmol) by stepwise hydrolysis first with excess of NaOH at r.t. and then with the excess of NaOH at heating (60° C., 1.5 h) to give 80 mg of product as white crystals (cis/trans ratio 78:22 according to HPLC).

EXAMPLE 75 a) 6-Bromoindene

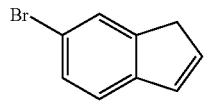

This compound was prepared analogously to Examples 69a & 69b from 5-bromo-1-indanone (4.0 g, 18.8 mmol) to give 2.4 g (65%) of 6-bromoindene.

b) (±)-cis-Ethyl 4-bromo-1,1a,6,6a-tetrahydrocyclopropa[a]indene-1-carboxylate

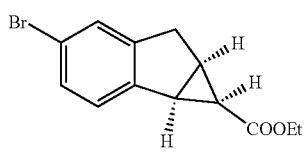

This compound was prepared analogously to Example 69c from 6-bromoindene (1.95 g, 10 mmol). Purification on silica gel starting with hexanes followed by hexanes with 2% diethyl ether and finally hexanes with 5% diethyl ether afforded 670 mg (24%) of the cis-ester.

c) (±)-cis-4-Bromo-1,1a,6,6a-tetrahydrocyclopropa[a]indene-1-carboxylic acid

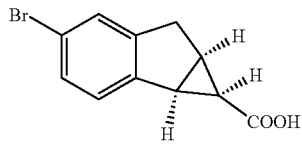

This acid was synthesized analogously to Example 69d starting with 330 mg (1.77 mmol) of the compound from Example 75b to give 232 mg (79%) of (±)-cis-4-Bromo-1,1a,6,6a-tetrahydrocyclopropa[a]indene-1-carboxylic acid.

EXAMPLE 76 a) (±)-cis-Ethyl 4-cyano-1,1a,6,6a-tetrahydrocyclopropa[a]indene-1-carboxylate

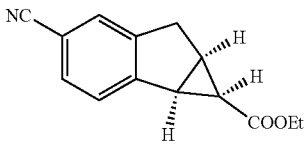

This compound was prepared analogously to Example 71d from (±)-cis-ethyl 4-bromo-1,1a,6,6a-tetrahydrocyclopropa[a]indene-1-carboxylate (200 mg, 0.7 mmol) to give, after purification on silica gel using hexanes with 10% ethyl acetate as the eluent, 73 mg (46%) of (±)-cis-ethyl 4-cyano-1,1a,6,6a-tetrahydrocyclopropa[a]indene-1-carboxylate.

b) (±)-cis-4-Cyano-1,1a,6,6a-tetrahydrocyclopropa[a]indene-1-carboxylic acid

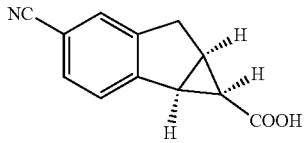

This acid was synthesized analogously to Example 69d starting with 73 mg (0.32 mmol) of the compound from Example 76a to give 59 mg (95%) of (±)-cis-4-cyano-1,1a,6,6a-tetrahydrocyclopropa[a]indene-1-carboxylic acid.

EXAMPLE 77 a) 4,7-Difluoro-1-indanone

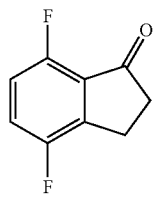

2,5-Difluorocinnamic acid (5.0 g, 27.2 mmol) was dissolved in 25 ml of ethanol and a catalytic amount of 10% Pd on carbon was added. The reaction mixture was hydrogenated at normal pressure for a period of 3 hrs. Filtration through celite and evaporation of the solvent afforded crude 3-(2,5-difluorophenyl)-propionic acid. This acid was dissolved in 75 ml of toluene and 5 ml of thionyl chloride was added. The reaction mixture was heated at +110° C. for a period of 2 hrs. Evaporation of the solvent afforded crude 3-(2,5-difluorophenyl)-propionyl chloride, which was dissolved in 25 ml of carbon disulfide and added drop wise to a suspension of 4 g of aluminium chloride in 100 ml of carbon disulfide. The reaction mixture was refluxed for 2 hrs and gave after work up and re-crystallization from ethanol 975 mg (22%) of 4,7-difluoro-1-indanone.

b) 4,7-Difluoroindene

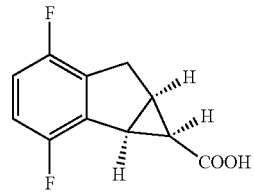

This compound was prepared analogously to Examples 69a & 69b from 4,7-difluoro-1-indanone (975 mg, 5.8 mmol) to give 475 mg (54%) of 4,7-difluoroindene.

c) (±)-cis-Ethyl 2,5-difluoro-1,1a,6,6a-tetrahydrocyclopropa[a]indene-1-carboxylate

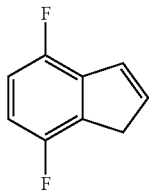

This compound was prepared analogously to Example 69c from 4,7-difluoroindene (475 mg, 3.13 mmol). Purification on silica gel starting with hexanes followed by hexanes with 2% diethyl ether and finally hexanes with 5% diethyl ether afforded 205 mg of the cis-ester contaminated with 22% of the trans-ester.

d) (±)-cis-2,5-Difluoro-1,1a,6,6a-tetrahydrocyclopropa[a]indene-1-carboxylic acid

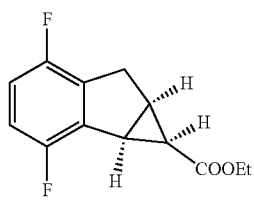

This acid was synthesized analogously to Example 69d starting with 205 mg cis-ester from Example 77c to give 120 mg of (±)-cis-2,5-difluoro-1,1a,6,6a-tetrahydrocyclopropa[a]indene-1-carboxylic acid containing a minor fraction of the corresponding trans-acid.

EXAMPLE 78

N-[(1S,1aR,7bR)-4,7-difluoro-1,1a,2,7b-tetrahydrocyclopropa[c]chromen-1-yl]-N'-[5-(2-fluorophenoxy)-2-pyridinyl]urea

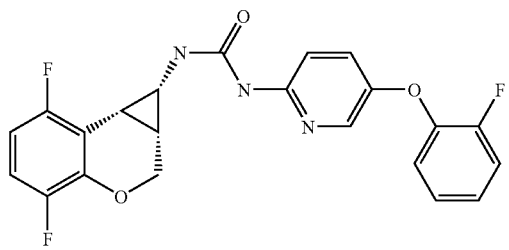

a) 5-(2-fluorophenoxy)-2-nitropyridine

Sodium hydride (60% dispersion in mineral oil, 0.11 g, 2.7 mmol) was mixed with 3-5 ml of dry dimethylformamide and 2-fluorophenol (0.24 ml, 2.7 mmol) was added to the stirred suspension. When the gas evolution was ceased the reaction mixture was heated at stirring at 60° C. and 5-bromo-2-nitropyridine (0.5 g, 2.5 mmol) was added to the reaction mixture in one portion. The reaction mixture was stirred at 60° C. for about 12 hours. The reaction mixture was then mixed with 50 ml of water and extracted into methylene chloride (3×20 ml). Organic extract was washed with water and brine, dried over magnesium sulfate and concentrated by rotary evaporation. The resulting mixture was purified by column chromatography on silica (30 g, EtOAc/hexane 1:3) to give 326 mg (57% yield) of desired product.
$^1$H-NMR (CDCl$_3$): 8.34 (d, 1H), 8.25 (d, 1H), 7.36-7.40 (m, 1H), 7.23-7.34 (m, 4H).

b) 5-(2-fluorophenoxy)-2-pyridinamine 5-(2-fluorophenoxy)-2-nitropyridine (326 mg) was mixed with 15-20 ml of ethanol and bubbled with argon. About 20 mg of Pd/C was added to the reaction mixture and hydrogen gas was applied at normal pressure and ambient temperature for 3 h. The reaction was monitored by TLC. After the reaction was complete, the reaction mixture was bubbled with argon, filtered through Celite and the solution obtained was concentrated by rotary evaporation to give 200 mg of desired aminopyridine (quantitative yield).

$^1$H-NMR (CDCl$_3$): 790 (d, 1H), 7.10-7.20 (m, 2H), 7.00-7.05 (m, 2H), 6.87-6.94 (m, 1H), 6.49 (d, 1H), 4.51 (br s, 2H).

c) N-[(1S,1aR,7bR)-4,7-difluoro-1,1a,2,7b-tetrahydrocyclopropa[c]chromen-1-yl]-N-[5-(2-fluorophenoxy)-2-pyridinyl]urea (1S,1aR,7bS)-4,7-difluoro-1,1a,2,7b-tetrahydro-cyclopropa[c]chromene-1-carboxylic acid (50 mg, 0.22 mmol, ~95% ee) was mixed with toluene (1,5 ml), triethylamine (1.1 eq), 5-(3-fluorophenyl)-2-aminopyridine (1.1 eq), DPPA (1.1 eq) and bubbled with argon for about 5 min. The reaction mixture was then heated at stirring at 110° C. for 3 h under in a closed vial. The reaction mixture was concentrated by rotary evaporation and purified by column chromatography on silica (30 g, ethylacetate/hexane 1:1). Desired product was obtained as white powder (61 mg, yield 64%).

$^1$H-NMR (CDCl$_3$): 9.44 (br s, 1H), 9.39 (br s, 1H), 7.53 (d, 1H), 7.00-7.27 (m, 4H), 6.93-6.99 (m, 1H), 6.84 (d, 1H), 6.74 (m, 1H), 6.54 (d tr, 1H), 4.43 (dd, 1H), 4.33 (dd, 1H), 3.79 (q, 1H), 2.57 (br tr, 1H), 1.90-1.98 (m, 1H).

EXAMPLE 79

N-[(1S,1aR,7bR)-4,7-difluoro-1,1a,2,7b-tetrahydro-cyclopropa[c]chromen-1-yl]-N'-{5-[(4-fluorophenyl)(hydroxy)methyl]-2-pyridinyl}urea

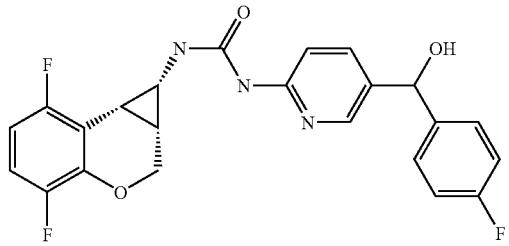

a) (6-chloro-3-pyridinyl)(4-fluorophenyl)methanone

Aluminium chloride (2 g) was suspended in 3 ml of fluorobenzene. A solution of 6-chloronicotinoyl chloride (1 g, 5.7 mmol) in 2 ml of fluorobenzene was added to the stirred reaction mixture by syringe and stirred at 80° C. overnight in a closed vial. The reaction mixture was deluted with EtOAc and basified with aqueous sodium hydroxide (pH>8.5). The precipitate formed was removed by filtration. The organic solution was washed with water, dried over magnesium sulfate and concentrated by rotary evaporation. Desired product was purified by column chromatography on silica (EtOAc/hexane) to give 1.22 g (90%).

$^1$H-NMR (CDCl$_3$): 8.75 (dd, 1H), 8.08 (dd, 1H), 7.82-7.87 (m, 2H), 7.50 (dd, 1H), 7.21 (tr, 2H).

b) (6-amino-3-pyridinyl)(4-fluorophenyl)methanone (6-Chloro-3-pyridinyl)(4-fluorophenyl)methanone (0.3 g) was mixed with 3 ml of abs ethanol and 7 ml of liquid ammonia in an Ace ampule (suitable for work under pressure). The ampule was closed with Teflon stopper (CAPFE O-ring) and heated at 145° C. for 14 h. The reaction mixture was cooled down and concentrated by rotary evaporation to give 0.22 g of orange-brown oil. The oil obtained was mixed with 1N HCl and precipitate formed was collected by filtration (starting material). The acidic solution was washed with EtOAc and basified with 1N NaOH. Basic solution was extracted into EtOAc. Organic extract was washed with water and brine, dried over magnesium sulfate. Purification by column chromatography gave 60 mg of desired amine.

$^1$H-NMR (CDCl$_3$): 8.5 (d, ~1H), 7.98 (dd, 1H), 7.79 (m, 2H), 7.15 (tr, 2H), 6.55 (d, 1H), 4.95 (br s, 2H); LC-MS: M$^+$217, M$^-$215.

c) N-[(1S,1aR,7bR)-4,7-difluoro-1,1a,2,7b-tetrahydro-cyclopropa[c]chromen-1-yl]-N'-[5-(4-fluorobenzoyl)-2-pyridinyl]urea (1S,1aR,7bS)-4,7-difluoro-1,1a,2,7b-tetrahydrocyclopropa[c]chromene-1-carboxylic acid (40 mg, 0.18 mmol, ~95% ee) was mixed with toluene (1 ml), triethylamine (1.1 eq), (6-amino-3-pyridinyl)(4-fluorophenyl)methanone (1.1 eq), DPPA (1.1 eq) and bubbled with argon. The reaction mixture was then heated at stirring at 110° C. for 3 h under in a closed vial. The reaction mixture was concentrated by rotary evaporation and purified by column chromatography on silica (30 g, ethylacetate/hexane 1:4). The last fraction collected contained desired product together with starting aminopyridine (25%, NMR data). The mixture was dissolved in methylene chloride and washed with 1N HCl, water and brine. Organic layer was dried over magnesium sulphate. Concentration gave pure product as white powder (30 mg, yield 39%).

$^1$H-NMR (CDCl$_3$): 9.74 (br d, 1H), 9.57 (br s, 1H), 8.22 (d, 1H), 8.06 (dd, 1H), 7.80 (m, 2H), 7.22 (t, 2H), 6.91 (d, 1H), 6.74-6.81 (m, 1H), 6.57 (tr d, 1H), 4.49 (dd, 1H), 4.33 (dd, 1H), 3.86 (q, 1H), 2.65 (br tr, 1H), 1.97-2.03 (m, 1H). LC-MS: M$^+$440, M$^-$438.

d) N-[(1S,1aR,7bR)-4,7-difluoro-1,1a,2,7b-tetrahydrocyclopropa[c]chromen-1-yl]-N'-{5-[(4-fluorophenyl)(hydroxy)methyl]-2-pyridinyl}urea N-[(1S,1aR,7bR)-4,7-difluoro-1,1a,2,7b-tetrahydrocyclopropa[c]chromen-1-yl]-N'-[5-(4-fluorobenzoyl)-2-pyridinyl]urea (20 mg) was dissolved in methanol and sodium borohydride (appr. 20 mg) was added to the reaction mixture in small portions. The reaction mixture was stirred for about 3 h at ambient temperature. The reaction was monitored by TLC. The reaction mixture was diluted with water, acidified with 1N HCl and extracted into methylene chloride. Organic extract low as washed with water and bine, dried over magnesium sulfate and concentrated. Purification by column chromatography on silica (EtOAc/hexane) gave 12 mg of pure product.

$^1$H-NMR (CDCl$_3$): 9.60 (br s, 1H), 8.20 (br s, 1H), 7.72 (s, 1H), 7.47 (d tr, 1H), 7.27-7.32 (m, 2H), 7.04 (t, 2H), 6.75 (m, 1H), 6.52-6.62 (m, 2H), 5.72 (br s, 1H), 4.43 (d tr, 1H), 4.32 (dd, 1H), 3.76 (q, 1H), 2.67 (br s, 1H), 2.58 (br tr, 1H), 1.91-1.98 (m, 1H).

EXAMPLE 80

N-[(1S,1aR,7bR)-4,7-difluoro-1,1a,2,7b-tetrahydro-cyclopropa[c]chromen-1-yl]-N'-[5-(4-fluorobenzyl)-2-pyridinyl]urea

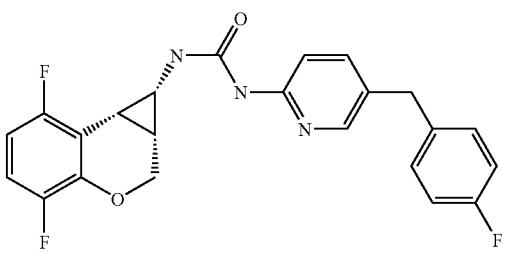

a) 5-(4-fluorobenzyl)-2-pyridinylamine (6-Amino-3-pyridinyl)(4-fluorophenyl)methanone (30 mg, 0.138 mmol) was dissolved in 1 ml of trifluoroacetic acid. 161 of sulfuric acid (2.2 eq) and 50 l of Et₃SiH and stirred at ambient temperature for 4 h in a closed vial. The reaction mixture was poured into water, basified with 2N sodium hydroxide and extracted into methylene chloride. Organic extract was washed with water and brine, concentrated and purified by column chromatography on silica (10 g, EtOAc/hexane 1:1) to give 12 mg of desired product (43% yield).

b) N-[(1S,1aR,7bR)-4,7-difluoro-1,1a,2,7b-tetahydrocyclopropa[c]chromen-1-yl]-N'-[5-(4-fluorobenzyl)-2-pyridinyl]urea (1S,1aR,7bS)-4,7-difluoro-1,1a,2,7b-tetrahydrocyclopropa[c]chromene-1-carboxylic acid (11 mg, 0.05 mmol, ~95% ee) was mixed with toluene (1 ml), triethylamine (1.1 eq), 5-(4-fluorobenzyl)-2-pyridinylamine (1.1 eq), DPPA (1.1 eq) and bubbled with argon. The reaction mixture was then heated at stirring at 110° C. for 3 h under in a closed vial. The reaction mixture was concentrated by rotary evaporation and purified by column chromatography on silica (10 g, ethylacetate/hexane 1:1) to give 4 mg (19%) of pure product.

¹H-NMR (CDCl₃): 9.60 (br s, 1H), 8.05 (br s, 1H), 7.59 (d, 1H), 7.29 (dd, 1H), 7.05-7.10 (m, 2H), 6.99 (tr, 2H), 6.78 (m, 1H), 6.59 (m, 2H), 4.45 (dd, 1H), 4.34 (dd, 1H) 3.74-3.86 (m, 3H), 2.59 (br tr, 1H), 1.92-1.99 (m, 1H). LC-MS: M⁺426.

EXAMPLE 81

N-[(1S,1aR,7bR)-4,7-difluoro-1,1a,2,7b-tetrahydro-cyclopropa[c]chromen-1-yl]-N'-[5-(3-fluoro-4-(N-morpholinocarboxyamido)phenoxy)-2-pyridinyl]urea

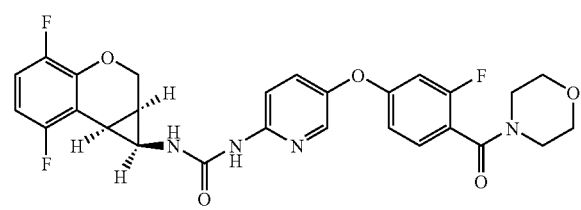

a) 5-(3-fluoro-4-(N-morpholinocarboxyamido)phenoxy)-2-nitropyridine

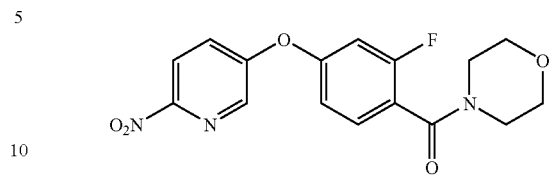

Potassium tert-butoxide (452 mg, 4.03 mmol) was added to a solution of 3-fluoro-4-(N-morpholinocarboxyamido)phenol (907 mg, 4.03 mmol) in DMF (6 ml) and the mixture was stirred for 1 hour at room temperature. Then the mixture was heated to 60° C. and 5-bromo-2-nitro pyridine (724 mg, 3.57 mmol) was added and the mixture was stirred at 60° C. for 12 hours. Then the solvent was evaporated and the residue extracted between water and methylene chloride. The organic phase was dried over sodium sulfate and evaporated. The resulting mixture was purified by column chromatography on silica gel (0-½-1% EtOH/methylene chloride) to give 743 mg (60% yield) of desired product.

¹H-NMR (CDCl₃): 8.39 (d, 1H), 8.30 (d, 1H), 7.53 (d, 1H), 7.53 (dd, 1H), 6.98 (dd, 1H), 6.88 (dd, 1H), 3.81 (m, 4H), 3.68 (tr, 2H), 3.39 (tr, 2H).

b) 5-(3-fluoro-4-(N-morpholinocarboxyamido)phenoxy)-2-pyridinamine

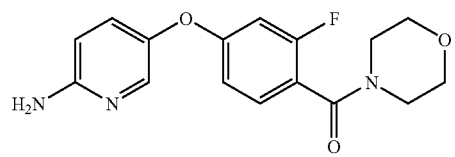

5-(3-fluoro-4-(N-morpholinocarboxyamido)phenoxy)-2-pyridinamine was synthesized analogously to Example 2 from 5-(3-fluoro-4-(N-morpholinocarboxyamido)phenoxy)-2-nitropyridine, after 2 hours stirring under hydrogen. The crude product was purified by column chromatography on silica gel (0-10% EtOH/methylene chloride) to give 411 mg of the title compound.

¹H-NMR (CDCl₃): 7.90 (d, 1H), 7.35 (dd, 1H), 7.20 (dd, 1H), 6.77 (dd, 1H), 6.62 (dd, 1H), 6.54 (d, 1H), 4.49 (br, 2H), 3.81 (m, 4H), 3.65 (tr, 2H), 3.37 (tr, 2H).

c) N-[(1S,1aR,7bR)-4,7-difluoro-1,1a,2,7b-tetrahydrocyclopropa[c]chromen-1-yl]-N'-[5-(3-fluoro-4-(N-morpholinocarboxyamido)phenoxy)-2-pyridinyl]urea The title compound was synthesized analogously to Example 3 from 5-(3-fluoro-4-(N-morpholinocarboxyamido)phenoxy)-2-pyridinamine (47 mg, 0.15 mmol), with the exception that the reaction mixture was worked up by extractions between EtAc and 5% citric acid followed by sat. aq. NaHCO₃, to give 34 mg of pure product as white powder (49% yield) after silica gel column chromatography (0-3½% EtOH/methylene chloride).

¹H-NMR (CDCl₃): 9.25 (br s, 1H), 7.66 (d, 1H), 7.44 (br s, 1H), 7.39 (dd, 1H), 7.29 (dd, 1H), 6.81 (tr d, 1H), 6.77 (dd, 1H), 6.68 (d, 1H), 6.63 (dd, 1H), 6.60 (d tr, 1H), 4.47 (dd, 1H), 4.32 (dd, 1H), 3.84-3.75 (m, 5H), 3.66 (tr, 2H), 3.38 (tr, 2H), 2.62 (tr, 1H), 201-1.95 (m, 1H). LC-MS: M+541, M−539

EXAMPLE 82

N-[(1S,1aR,7bR)-4,7-difluoro-1,1a,2,7b-tetrahydro-cyclopropa[c]chromen-1-yl]-N'-[5-(3-fluoro-4-(N-morpholinomethyl)phenoxy)-2-pyridinyl]urea

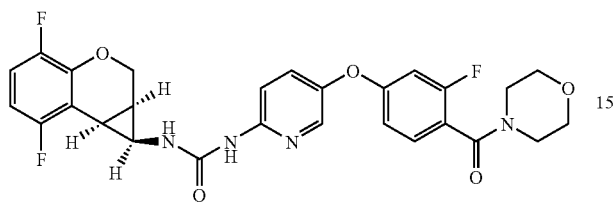

a) 5-(3-fluoro-4-(N-morpholinomethyl)phenoxy)-2-nitropyridine

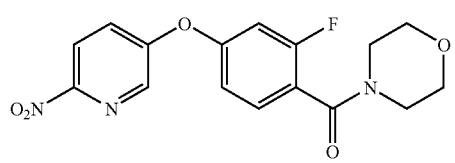

Borane in THF (1M, 0.79 ml, 0.79 mmol) was cooled to 0° C. A concentrated solution of 5-(4-(N-morpholinocarboxyamido)-3-fluorophenoxy)-2-nitropyridine (363 mg, 1.05 mmol) in THF was added through a syringe under argon. A few minutes after complete addition, the cooling was removed and the reaction mixture was heated to 75° C. and stirred for 1½ hours. 6M HCl (0.15 ml) was added and the mixture was stirred until gas evolution ceased. The THF was evaporated and the residual aqueous solution was basified by addition of near saturated Na$_2$CO$_3$ solution. The resulting aqueous layer was extracted with methylene chloride, which was dried through sodium sulfate and evaporated. The title compound was isolated from the residue by column chromatography on silica (0-6%EtOH/methylene chloride to give 73 mg (21% yield) as a yellow powder.

$^1$H-NMR (CDCl$_3$): 8.34 (d, 1H), 8.26 (d, 1H), 7.49 (tr, 1H), 7.46 (dd, 1H), 6.88 (dd, 1H), 6.84 (dd, 1H), 3.73 (tr, 4H), 3.58 (s, 2H), 2.50 (tr, 4H).

b) 5-(3-fluoro-4-(N-morpholinomethyl)phenoxy)-2-pyridinamine

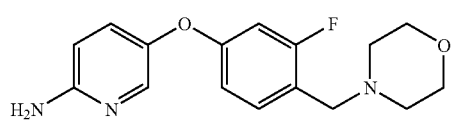

A hot clear water solution (0.25 ml) of sodium sulphide nonahydrate (58 mg, 0.24 mmol) and sulphur (14 mg, 0.447 mmol) was added to a water-dioxane mixture (1.12 ml, 1:1.5 v/v) of 5-(3-fluoro-4-(N-morpholinomethyl)phenoxy)-2-nitropyridine (72 mg, 0.216 mmol). The resulting solution was heated at 80° C. and stirred for 30 min. Then the reaction was cooled and the volatile matter was evaporated and the residue coevaporated with dioxane. The residue was slurried in 30% MeOH-chloroform and the insoluble matter was filtered off and the filtrate evaporated. The title compound was isolated from the resulting residue by column chromatography on silica (1-4% EtOH/methylene chloride to give 18 mg (28% yield) as a yellow powder.

$^1$H-NMR (CDCl$_3$): 7.91 (d, 1H), 7.26 (tr, 1H), 7.20 (dd, 1H), 6.68 (dd, 1H), 6.60 (dd, 1H), 6.53 (dd, 1H), 4.40 (br s, 2H), 3.70 (tr, 4H), 3.51 (s, 2H), 2.46 (tr, 4H).

c) N-[(1S,1aR,7bR)-4,7-difluoro-1,1a,2,7b-tetrahydro-cyclopropa[c]chromen-1-yl]-N'[5-(3-fluoro-4-(N-morpholinomethyl)phenoxy)-2-pyridinyl]urea The title compound was synthesized analogously to Example 3 from 5-(3-fluoro-4-(N-morpholinomethyl)phenoxy)-2-pyridinamine (27 mg, 0.089 mmol), with the exception that the reaction mixture was worked up by extractions between methylene chloride and 5% citric acid followed by sat. aq. NaHCO$_3$, to give 30 mg of product with >98% purity as white powder (72% yield) after silica gel column chromatography (0-4% EtOH/methylene chloride). $^1$H-NMR (CDCl$_3$): 9.25 (br s, 1H), 7.61 (d, 1H), 7.32 (tr, 1H), 7.26 (m, 2H), 6.81 (tr d, 1H), 6.70 (dd, 1H), 6.64-6.56 (m, 3H), 4.47 (dd, 1H), 4.33 (dd, 1H), 3.79 (dd, 1H), 3.71 (tr, 4H), 3.54 (s, 2H), 2.60 (tr, 1H), 2.48 (tr, 4H), 2.01-1.95 (m, 1H). LC-MS: M+527, M−525.

EXAMPLE 83

N-[(1S,1aR,7bR)-4,7-difluoro-1,1a,2,7b-tetrahydro-cyclopropa[c]chromen-1-yl]-N'-[5-(2-(N-morpholino)ethoxy)-2-pyridinyl]urea

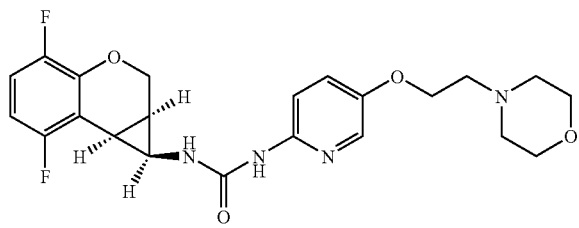

a) 5-(2-(N-morpholino)ethoxy)-2-pyridinamine

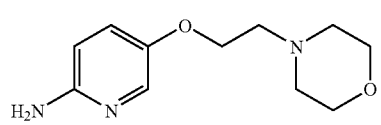

Sodium (26 mg, 1.14 mmol) was dissolved in 2-(N-morpholino)ethanol (9.5 ml). Then 2-amino-5-iodopyridine (500 mg, 2.27 mmol) was added followed by copper powder (202 mg, 3.18 mmol). The suspension was stirred at 160° C. for 40 hours. The solids were then filtered off and the volatile matter was evaporated. The residue was slurried in methylene chloride and the insolubles were filtered off through Celite. The title compound in the residual oil was isolated by column chromatography on silica (0-8% EtOH/methylene chloride. Yield 110 mg (21%).

¹H-NMR (CDCl₃): 7.80 (br s, 1H), 7.12 (dd, 1H), 6.48 (d, 1H), 4.25 (br s, 2H), 4.06 (tr, 2H), 3.74 (tr, 4H), 2.76 (tr, 2H), 2.56 (tr, 4H).

b) N-[(1S,1aR,7bR)-4,7-difluoro-1,1a,2,7b-tetrahydro-cyclopropa[c]chromen-1-yl]-N'-[5-(2-(N-morpholino)ethoxy)-2-pyridinyl]urea The title compound was synthesized analogously to Example 3 from 5-(2-N-morpholinoethoxy)-2-pyridinamine (33 mg, 0.15 mmol), with the exception that the reaction mixture was worked up by extractions between methylene chloride and 5% citric acid followed by sat. aq. NaHCO₃, to give 12.6 mg of product with >95% purity as white powder (19% yield) after silica gel column chromatography (2-10% EtOH/methylene chloride).

¹H-NMR (CDCl₃): 9.45 (br s, 1H), 8.08 (s, 1H), 7.52 (d, 1H), 7.16 (dd, 1H), 6.64-6.58 (m, 2H), 4.45 (dd, 1H), 4.33 (dd, 1H), 4.06 (tr, 2H), 3.84 (q, 1H), 3.75 (m, 4H), 2.78 (tr, 2H), 2.61-2.54 (m, 5H), 2.01-1.95 (m, 1H). LC-MS: M⁺447, M⁻445.

EXAMPLE 84

N-[(1S,1aR,7bR)-4,7-difluoro-1,1a,2,7b-tetrahydro-cyclopropa[c]chromen-1-yl]-N'-{5-[(6-bromo-3-pyridinyl)oxy]-2-pyridinyl}urea

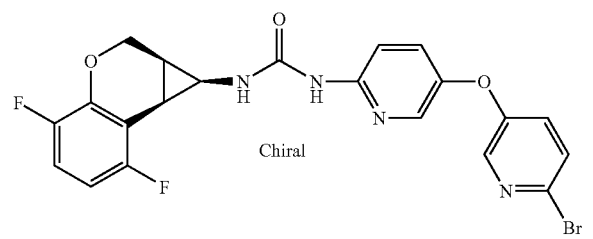

a) 5-[(6-bromo-3-pyridinyl)oxy]-2-nitropyridine

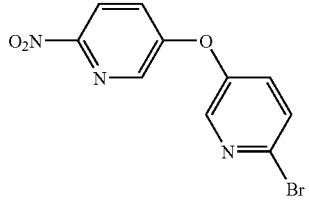

5-[(6-bromo-3-pyridinyl)oxy]-2-nitropyridine was synthesized analogously to Example 1 from 5-bromo-2-nitropyridine (203 mg, 1 mmol) and 2-bromo-3-hydroxypyridine (prepared according to WO9825920) to give 65 mg of product (22%).

¹H-NMR (CDCl₃): 8.38 (d, 1H), 8.31-8.28 (m, 2H), 7.6 (dd, 1H), 7.49 (dd, 1H), 7.35 (dd, (1H)

b) 5-[(6-bromo-3-pyrdinyl)oxy]-2-pyridinylamine

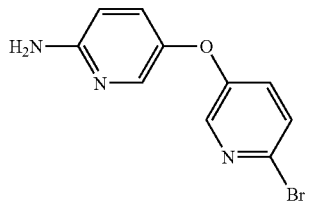

5-[(6-bromo-3-pyridinyl)oxy]-2-nitropyridine 65 mg, 0.22 mmol) was dissolved in acetic acid (1.5 ml) and water (2 ml) and heated to 50 degrees C. Iron powder (42 mg, 0.75 mmol) was added and the mixture was left for 1 h. Filtration and purification by column chromatography on silica (ethyl acetate/hexane 2:1) gave 57 mg, 97% of desired product.

¹H-NMR (CDCl₃): 8.11 (d, 1H), 7.92 (d, 1H), 7.39 (d, 1H), 7.2 (dd, 1H), 7.11 (dd, 1H), 6.54 (d, 1H).

c) N-[(1S,1aR,7bR)-4,7-difluoro-1,1a,2,7b-tetrahydrocyclopropa[c]chromen-1-yl]-N'-{5-[(6-bromo-3-pyridinyl)oxy]-2-pyridiny}urea N-[(1S,1aR,7bR)-4,7-difluoro-1,1a,2,7b-tetrahydro-cyclopropa[c]chromen-1-yl]-N'-{5-[(6-bromo-3-pyridinyl)oxy]-2-pyridinyl}urea was synthesized analogously to Example 3 from 5-[(6-bromo-3-pyridinyl)oxy]-2-pyridinylamine (37 mg, 0.14 mmol) and (1S,1aR,7bS)-4,7-difluoro-1,1a,2,7b-tetrahydrocyclopropa[c]chromene-1-carboxylic acid (32 mg, 0.14 mmol) to give 25 mg (36%) of pure product.

¹H-NMR (CDCl₃): 9.4 (br s, 2H), 8.12 (d, 1H), 7.63 (d, 1H), 7.43 (d, 1H), 7.27 (dd, 1H), 7.12 (dd, 1H), 6.88 (d, 1H), 6.81 (m, 1H), 6.57 (m, 1H), 4.49 (dd, 1H), 4.30 (dd, 1H), 4.83 (q, 1H), 2.62 (t, 1H), 1.98 (m, 1H)

EXAMPLE 85

N-[(1S,1aR,7bR)-4.7-difluoro-1,1a,2,7b-tetrahydro-cyclopropa[c]chromen-1-yl]-N'-{5-[6-cyano-3-pyridinyl)oxy]-2-pyridinyl}urea

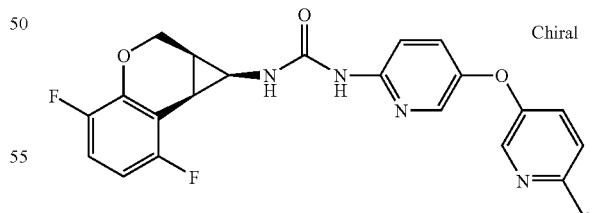

N-[(1S,1aR,7bR)-4,7-difluoro-1,1a,2,7b-tetrahydrocyclopropa[c]chromen-1-yl]-N'-{5-[6-bromo-3-pyridinyl)oxy]-2-pyridinyl}urea (100 mg, 0.2 mmol), zink cyanide (70 mg, 0.6 mmol) and tertrakis(triphenylphospine)palladium(0) (46 mg, 20 mol % was dissolved in DMF and heated at 85° C. for 24 h. under argon atmosphere. The reaction mixture was then extracted between ethyl acetate and 1 M potassium carbonate.

The organic solvent was removed under reduced pressure and the crude product was purified by chromatography (silica, 1% methanol in diethyl ether) to give 25 mg (28%) of pure product.

¹H-NMR (CDCl₃+MeOD): 8.10 (d, 1H), 7.63 (d, 1H), 7.45 (d, 1H), 7.28 (dd, 1H), 7.13 (dd, 1H), 6.85-6.79 (m, 2H), 6.64-6.58 (m, H), 4.46 (dd, 1H), 4.32 (dd, 1H), 3.74 (q, 1H), 2.61 (t, 1H), 2.01-1.96 (m, 1H)

EXAMPLE 86

N-[(1S,1aR,7bR)-4,7-difluoro-1,1a,2,7b-tetrahydro-cyclopropa[c]chromen-1-yl]-N'-[5-(3-fluoroanilino)-2-pyridinyl]urea

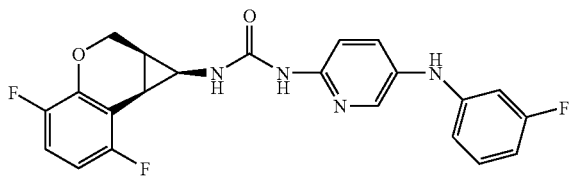

a) N-(3-fluorophenyl)-6-nitro-3-pyridinamine

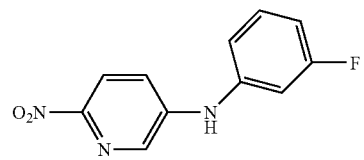

This compound was prepared from 2-nitro-5-bromopyridine and 3-fluoroaniline using the catalytic amination procedure described for similar compounds in Tetrahedron Lett. Vol. 38, No 36, pp. 6359-6362 1997.

8.62 (d, 1H), 8.51 (dd, 1H), 8.11 (dd, 1H), 7.69 (dt, 1H), 7.41 (ddd, 1H), 7.25 (dd, 1H), 6.61 (ddd, 1H), 6.39 (d, 1H).

b) N⁵-(3-fluorophenyl)-2,5-pyridinediamine

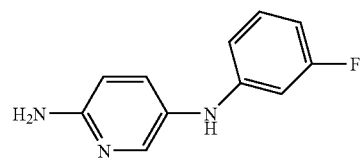

This compound was easily prepared from N-(3-fluorophenyl)-6-nitro-3-pyridinamine 210 mg, 0.9 mmol) by catalytic hydrogenation (Raney nickel at atmospheric pressure) in methanol to give the desired product (180 mg, 98%)

c) N-[(1S,1aR,7bR)-4,7-difluoro-1,1a,2,7b-tetrahydrocyclopropa[c]chromen-1-yl]-N'-[5-(3-fluoroanilino)-2-pyridinyl]urea N-[(1S,1aR,7bR)-4,7-difluoro-1,1a,2,7b-tetrahydro-cyclopropa[c]chromen-1-yl]-N'-[5-(3-fluoroanilino)-2-pyridinyl]urea was synthesized analogously to Example 3 from N⁵-(3-fluorophenyl)-2,5-pyridinediamine (180 mg, 0.88 mmol) and (1S,1aR,7bS)-4,7-difluoro-1,1a,2,7b-tetrahydro-cyclopropa[c]chromene-1-carboxylic acid (200 mg, 0.88 mmol) to give 94 mg (25%).

¹H-NMR (CDCl₃): 9.2 (br s, 2H), 7.68 (d, 1H), 7.35 (dd, 1H), 7.2-7.15 (m, 2H), 6.9-6.8 (m, 1H), 6.65-6.53 (m, 5H), 5.49 (s, 1H), 4.4 (dd, 2H), 3.8 (q, 1H), 2.58 (t, 1H), 2.0-1,95 (m, 1H)

Biological Results

Extensive guidance on the assay of test compounds at the enzyme level and in cell culture, including the isolation and/or selection of mutant HIV strains and mutant RT are found in DAIDS Virology Manual for HIV Laboratories complied by Division of AIDS, NIAID USA 1997. Resistance studies, including rational for various drug escape mutants is described in the HIV Resistance Collaborative Group Data Analysis Plan for Resistance Studies, revised 31 Aug. 1999.

Compounds of the invention are assayed for HIV activity, for example using multiple determinations with XTT in MTA-4 cells (Weislow et al, J Nat Cancer Inst 1989, vol 81 no 8, 577 et seq), preferably including determinations in the presence of 40-50% human serum to indicate the contribution of protein binding. In short the XTT assay uses human T cell line MT4 cells grown in RPMI 1640 medium supplemented with 10% fetal calf serum (or 40-50% human serum as appropriate), penicillin and streptomycin seeded into 96 well microplates (2·10⁴ cells/well) infected with 10-20 TCID₅₀ per well of HIV-1$_{IIIB}$ (wild type) or mutant virus, such as those bearing RT Ile 100, Cys 181 or Asn 103 mutations. Serially diluted test compounds are added to respective wells and the culture incubated at 37° C. in a CO₂ enriched atmosphere and the viability of cells is determined at day five or six with XTT vital dye. Results are typically presented as ED₅₀ μM.

Compounds are preferably potent against wild type virus and mutant HIV virus, especially virus comprising drug escape mutations. Drug escape mutations are those which arise in patients due to the selective pressure of a prior art antiviral and which confer enhanced resistance to that antiviral. The above cited Data Analysis Plan outlines relevant drug escape mutants for each of the antiviral classes currently on the market. Drug escape clones are readily isolated from HIV patients who are failing on a particular antiviral therapy. Alternatively the preparation of RT mutations on a known genetic background is shown in WO97/27319, WO99/61658 and WO00/73511 which also show the use of such mutants in sensitivity profiling.

K103 N is a particularly relevant drug escape mutant in the context of NNRTI therapy and compounds of the invention preferably have a low ED₅₀ against this mutant, especially in assays mimicking the presence of human serum. Compounds of the invention, such as those exemplified above typically show sub micromolar activities in such assays.

The invention claimed is:

1. A compound of the formula Y:

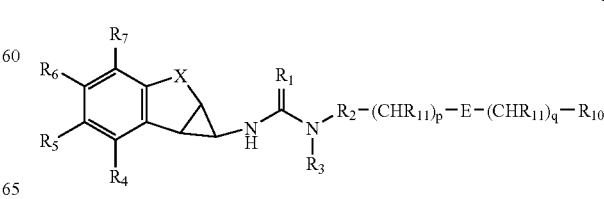

where;

$R_1$ is O, S;

$R_2$ is pyrid-2-yl, substituted at the 5 position with the —$(CHR_{11})_p$-E-$(CHR_{11})_q$—$R_{10}$ moiety;

$R_3$ is H;

$R_4$ and $R_7$ are fluoro;

$R_5$ and $R_6$ are H;

X is —$(CR_8R_8')_n$-D-$(CR_8R_8')_m$—;

D is O;

m is 1;

n is 0;

$R_8$ and $R_8'$ are H;

E is —O;

p and q are 0;

$R_{10}$ is pyrid-3yl, optionally substituted with halo or cyano;

and pharmaceutically acceptable salts and prodrugs thereof.

2. A compound according to claim 1, wherein $R_1$ is O.

3. A compound according to claim 1, wherein the cyclopropyl moiety has an enantiomeric excess of the conformation depicted in the partial formulae:

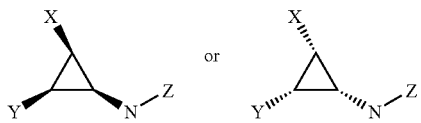

where X is as defined, Y is the bridge to the (substituted) phenyl ring depicted in formula I and Z is bond to the urea-$R_2$—$(CHR_{11})_p$-E-$(CHR_{11})_q$—$R_{10}$ moiety depicted in formula I.

4. A compound according to claim 1 wherein the compound of formula I comprises an enantiomeric excess of the isomer showing negative optical activity.

5. A compound according to claim 1, wherein $R_{10}$ is cyano or fluoro substituted pyrid-3-yl.

6. A pharmaceutical composition comprising a compound as defined in any one of claims 1, 3, 4, and 5, and a pharmaceutically acceptable vehicle or diluent therefor.

7. A composition according to claim 6, further comprising 1 to 3 additional HIV antivirals selected from the group consisting of AZT, ddI, ddC, D4T, 3TC, DAPD, alovudine, abacavir, adefovir, adefovir dipivoxil, bis-POC-PMPA, foscarnet, efavirenz, trovirdine, capravirine, nevirapine, delaviridine, tipranavir, emtricitabine, omaciclovir, valomaciclovir stearate, TMC-126, TMC-125, TMC-120, efavirenz, loviride, ritonavir, kaletra, lopinavir, saguinavir, lasinavir, indinavir, amprenavir, amprenavir phosphate and nelfinavir.

8. A method of treatment of HIV-1 infections comprising administering to a patient infected with HIV-1 an effective amount of the compound as defined by claim 1.

9. The method of claim 8, wherein said HIV-1 infection is a drug escape mutant.

10. The method of claim 9, wherein said drug escape mutant comprises the K1031 mutation.

11. The method of claim 8, wherein the compound has the formula:

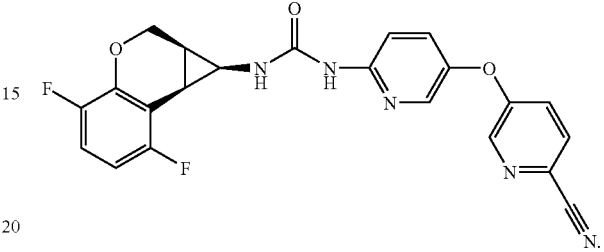

12. A compound according to claim 5, wherein $R_{10}$ is 6-cyano-pyrid-3-yl.

13. The compound of claim 1 with the formula:

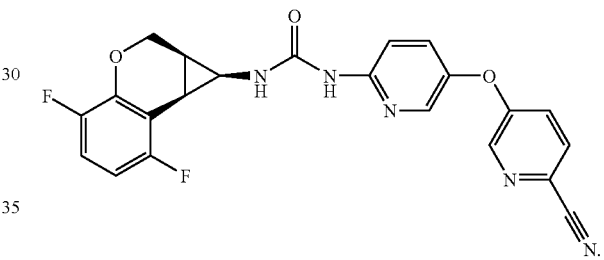

14. A pharmaceutical composition comprising the compound of claim 12 and a pharmaceutically acceptable vehicle or diluent therefor.

15. The pharmaceutical composition of claim 13, further comprising 1-3 additional antivirals selected from the group consisting of AZT, ddI, ddC, D4T, 3TC, DAPD, alovudine, abacavir, adefovir, adefovir dipivoxil, bis-POC-PMPA, foscarnet, efavirenz, trovirdine, capravirine, nevirapine, delaviridine, tipranavir, emtricitabine, omaciclovir, valomaciclovir stearate, TMC-126, TMC-125, TMC-120, efavirenz, loviride, ritonavir, kaletra, lopinavir, saquinavir, lasinavir, indinavir, amprenavir, amprenavir phosphate, and nelfinavir.

* * * * *